US009066930B2

(12) United States Patent
Yan et al.

(10) Patent No.: US 9,066,930 B2
(45) Date of Patent: Jun. 30, 2015

(54) ACTIVIN RECEPTOR-LIKE KINASE-1 COMPOSITIONS AND METHODS OF USE

(75) Inventors: Minhong Yan, Foster City, CA (US); Gu Zhang, Millbrae, CA (US)

(73) Assignee: Genentech, Inc., South San Francisco, CA (US)

( * ) Notice: Subject to any disclaimer, the term of this patent is extended or adjusted under 35 U.S.C. 154(b) by 892 days.

(21) Appl. No.: 13/112,954

(22) Filed: May 20, 2011

(65) Prior Publication Data

US 2012/0171203 A1    Jul. 5, 2012

Related U.S. Application Data

(63) Continuation of application No. 12/265,154, filed on Nov. 5, 2008, now abandoned.

(60) Provisional application No. 60/986,876, filed on Nov. 9, 2007, provisional application No. 61/098,557, filed on Sep. 19, 2008.

(51) Int. Cl.
*A61K 39/00* (2006.01)
*A61K 39/395* (2006.01)

(52) U.S. Cl.
CPC ....... *A61K 39/39558* (2013.01); *C07K 2319/30* (2013.01)

(58) Field of Classification Search
CPC .......................... C07K 2319/30; A61K 39/00
See application file for complete search history.

(56) References Cited

U.S. PATENT DOCUMENTS

| | | | |
|---|---|---|---|
| 5,116,964 A | 5/1992 | Capon et al. | |
| 5,428,130 A | 6/1995 | Capon et al. | |
| 6,582,959 B2 | 6/2003 | Kim | |
| 6,703,020 B1 | 3/2004 | Thorpe et al. | |
| 6,884,879 B1 | 4/2005 | Baca et al. | |
| 2003/0055006 A1 | 3/2003 | Siemeister et al. | |
| 2003/0190317 A1 | 10/2003 | Baca et al. | |
| 2003/0203409 A1 | 10/2003 | Kim | |
| 2003/0206899 A1 | 11/2003 | Ferrara et al. | |
| 2005/0005314 A1* | 1/2005 | Inghirami et al. | 800/14 |
| 2005/0112126 A1 | 5/2005 | Baca et al. | |
| 2005/0186208 A1 | 8/2005 | Fyfe et al. | |
| 2007/0065444 A1* | 3/2007 | North et al. | 424/146.1 |
| 2008/0175844 A1* | 7/2008 | Grinberg et al. | 424/139.1 |

FOREIGN PATENT DOCUMENTS

| | | | |
|---|---|---|---|
| EP | 0 666 868 B1 | 4/2002 | |
| TW | 200817435 A | 4/2008 | |
| TW | 200950806 A | 12/2009 | |
| WO | WO-91/08298 A2 | 6/1991 | |
| WO | WO-94/10202 A1 | 5/1994 | |
| WO | WO-96/30046 A1 | 10/1996 | |
| WO | WO-98/45332 A2 | 10/1998 | |
| WO | WO-2004/113304 A1 | 12/2004 | |
| WO | WO-2005/012359 A2 | 2/2005 | |
| WO | WO-2005/044853 A2 | 5/2005 | |
| WO | WO-2005/077981 A2 | 8/2005 | |
| WO | WO-2007/040912 A2 | 4/2007 | |
| WO | WO-2007/143689 A2 | 12/2007 | |
| WO | WO-2007/143689 A3 | 12/2007 | |
| WO | WO-2007/143689 A8 | 12/2007 | |
| WO | WO-2008/057461 A2 | 5/2008 | |
| WO | WO-2009/134428 A2 | 11/2009 | |
| WO | WO-2009/134428 A3 | 11/2009 | |

OTHER PUBLICATIONS

Achen et al . (May 22, 2006). "Minireview: Targeting Lymphangiogenesis to Prevent Tumour Metastasis" *Br J Cancer* 94(10) :1355-1360.

Ashkenazi et al. (1993). "Immunoadhesins" *Intern. Rev. Immune .* 10:219 227.

Ashkenazi et al. (Dec 1991). "Protection Against Enaotoxic Shock: by a Tumor Necrosis Factor Receptor Immunoadhesin," *Proc. Natl. Acad. Sci.* 88:10535-10539.

Bergers et al. (May 2003). "Benefits of Targeting Both Pericytes and Endothelial Cells in the Tumor Vasculature With Kinase Inhibitors," *The Journal of Clinical Investigation* 111(9):1287-1295.

Carmeliet et al. (Sep. 14, 2000). "Angiogenesis in Cancer and Other Diseases," *Nature* 407(6801):249-257.

Chang et al. (Dec. 2002). "Lymphangiogenesis New Mechanisms" *Ann N Y Acad Sci.* 979:111-119.

David et al. (Mar. 2007). "Identification of BMP9 and BMP10 as Functional Activators of the Orphan Activin Receptor-like Kinase 1 (ALK1) in Endothelial Cells" *Blood* 109(5) :1953-1961.

Dietsch et al. (1993). "Bispecific Receptor Globulins, Novel Tools for the Study or Cellular Interactions" *Journal of Immunological Methods* 162:123-132.

Ferrara et al. (Dec. 1999). "Clinical Applications of Anglogenic Growth Factors and Their 1nhibtors" *Nat Med.* 5(12):1359-1364.

Ferrara et al. (May 2004). "Discovery and Development of Bevacizuman, An Anti-VEGF Antibody for Treating Cancer" *Nature Reviews—Drug Discovery* 3:391-400.

Folkman et al. (1989). "Induction of Angiogenesis During the Transition From Hyperplasia to Neoplasia," *Nature* 339(6219):58-61.

Folkman et al. (Jun. 5, 1992). "Angiogenesis" *J Bio Chem.* 267 (16J: 10931-10934).

Folkman. (1995). "Angiogenesis in Cancer, Vascular, Rheumatoid and Other Disease" *Nature Medicine* 1(1) :27-31.

Garner, A. (1994). "Chapter 52 Vascular Diseases" Pathobiology of Ocular Disease. A Dynamic Approach, Garner, A., Klintworth GK Eds., 2nd edition, NY: Marcel Dekker pp. 1625-1710.

Gupta et al. (Nov. 2006). "Cancer Metastasis: Building a Framework" *Cell* 127(4):679-695.

(Continued)

*Primary Examiner* — Lei Yao

(74) *Attorney, Agent, or Firm* — Morrison & Foerster LLP

(57) ABSTRACT

Disclosed herein are methods and compositions for treating disorders associated with angiogenesis or lymphangiogenesis using ALK-1 antagonists.

12 Claims, 13 Drawing Sheets

(56) References Cited

OTHER PUBLICATIONS

Hanahan, D. (1997). "Signaling Vascular Morphogenesis and Maintenance" *Science* 277:48-50.
Hogan et al. (Jul. 2002). "Organogenesis: Molecular Mechanisms or Tubulogenesis" *Nature Reviews Genetics* 3(7):513-523.
Horak et al. (1992). "Angiogenesis, Assessed by Platelet/Endothelial Cell Adhesion Molecule Antibodies, as Indicator of Node Metastases and Survival in Breast Cancer" *Lancet* 340(8828) :1120-1124.
Houck et al. (1991). "The Vascular Endothelial Growth Factor Family: Identification of a Fourth Molecular Species and Characterization of Alternative Splicing of RNA" *Mol. Endocrinol.* 5(12):1806-1814.
Klagsnrun et al. (1991). "Regulators of Angiogenesis" *Ann. Rev. Physiol* 53:217-239.
Leung et al. (Dec. 8, 1989). "Vascular Enaothelial Growth Factor is a Secreted Angiogenic Mitogen" *Science* 246:1306-1309.
Lovell et al. (Mar. 2000). "Etanercept in Children With Polyarticular Juvenile Rheumatoid Arthritis Pediatric Rheumatology Collaborative Study Group" *N Engl J Med.* 342 (11): 763-769.
Luoarsky et al. (Jan. 10, 2003). "Tube Morphogenesis: Making and Shaping Biological Tubes" *Cell* 112(1):19-28.
Macchiarini et al. (Jul. 18, 1992). "Relation of Neovascularisation to Metastasis of Non-small-cell Lung Cancer" *Lancet* 340:145-146.
Maini et al. (2000). "Anti-cytokine Therapy for Rheumatoid Arthritis," *Annu Rev Med* 51:207-229.
Mallet et al. (Nov. 2006). "TGFbeta1 Induces Vasculogenesis and Inhibits Angiogenic Sprouting in an Embryonic Stem Cell Differentiation Model: Respective Contribution of ALK1 and ALK5" *Stem Cells* 24 (11): 2420-2427.
Nakatsu et al. (Sep. 2003). "Angiogenic Sprouting and Capillary Lumen Formation Modeled by Human Umbilical Vein Endothelial Cells (UVEC) in Fibrin Gels: The Role of Fibroblasts and Angiopietin-1," *Microvasc Res.* 66(2):102-112.
Nathanson. (2003). "Insights Into the Mechanisms of Lymph Node Metastasis," *Cancer* 98:413-423.
Pisetsky. (Mar. 2003). "Tumor Necrosis Factor Blockers in Rheumatoid Arthritis," *N Eng J Med.* 342(11) :910-911.
Popkov et al. (May 2004). "Human/Mouse Cross-Reactive Anti-VEGF Receptor 2 Recombiant Antibodies Selected From an Immune 'b9 Allotype Rabbit Antibody Library" *J Immunol Methods* 299(1-2):149-164.
Presta et al. (Oct. 15, 1997). "Humanization of an Anti-Vascular Endothelial Growth Factor Monoclonal Antibody for the Therapy of Solid Tumors and Other Disorders" *Cancer Research* 57(20) :4593-4599.
Robinson et al. (Mar. 2001). "The Splice Variants of Vascular Endothelial Growth Factor (VEGFJ and Their Receptors" *J Cell Sci.* 114 (5):953-965.
Sato. (Aug. 2003). "Molecular Diagnosis of Tumor Angiogenesis and Anti-Angiogenic Cancer Therapy" *Int J Clin Oncol.* 8( 4):200-206.
Scharpfeneckcer et al. (Mar. 2007). "BMP-9 Signals via ALKI and Inhibits bFGF-Induced Endothelial Cell Proliferation and VEGF-Stimulated Angiogenesis" *J Cell Sci.* 120 (Pt 6):964-972.
Streit et al. (May 19, 2003). "Angiogenesis, Lympnangiogenesis, and Melanoma Metastasis" *Oncogene* 22(20):3172-3179.
Tonini et al. (Sep. 2003). "Molecular Basis of Anglogenesis and Cancer" *Oncogene* 22(42):6549-6556.
Ungefroren et al. (Apr. 2007). "Antitumor Activity of ALKI in Pancreatic Carcinoma Cells" *Int J Cancer* 120(8):1641-1651.
Weidner et al. (1991) "Tumor Angiogenesis and Metastasis—Correlation in Invasive Breast Carcinoma" *New England J. of Medicine* 324(1):1-9.
Weinblatt et al. (1999). "A Trial of Etanercept, a Recombinant Tumor Necrosis Factor Receptor: Fc Fusion Protein, in Patients with Rheumatoid Arthritis Receiving Methotrexate," *New England J. of Medicine* 340(4):253-259.

\* cited by examiner

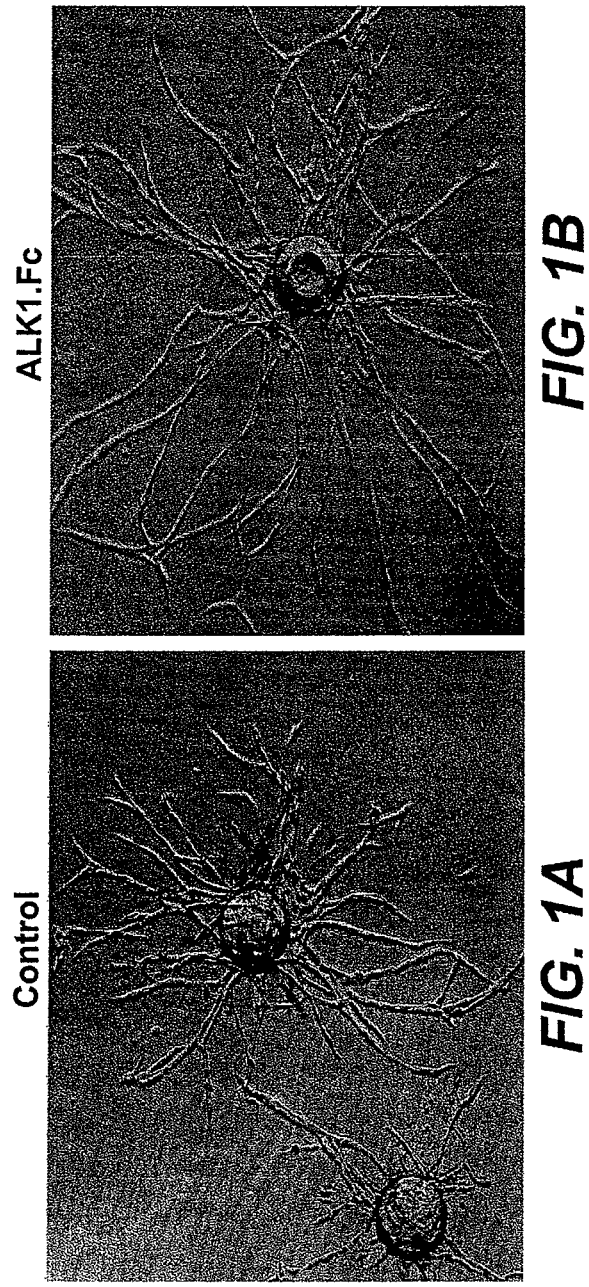

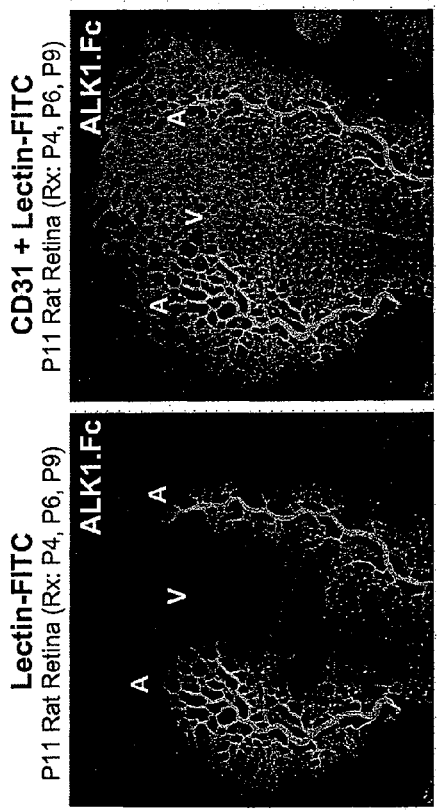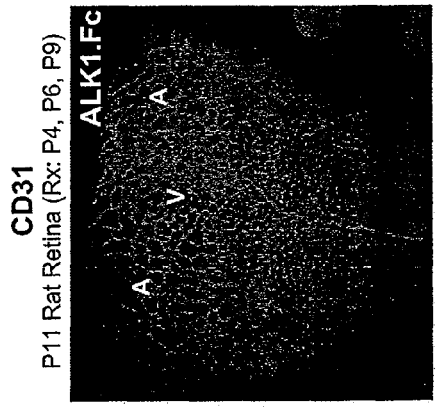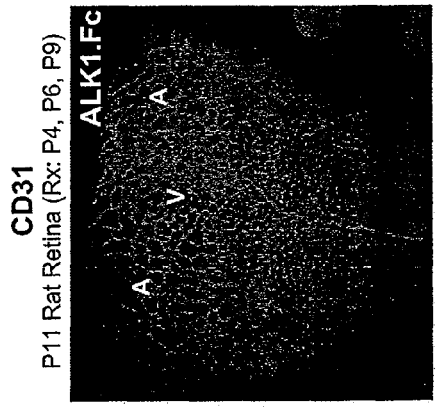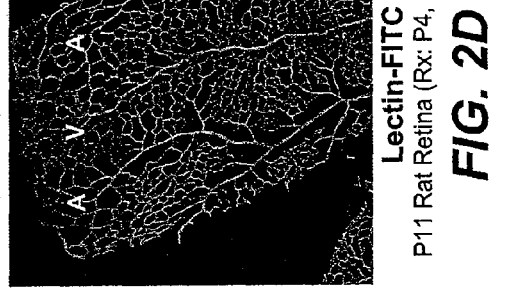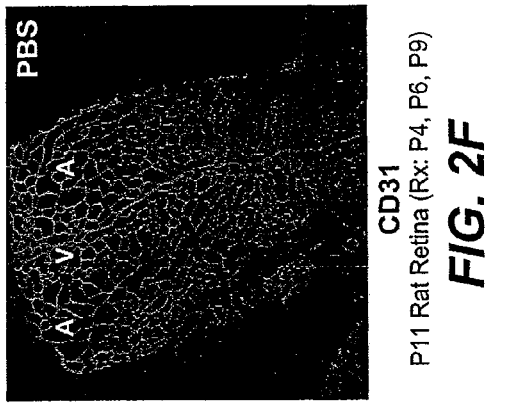

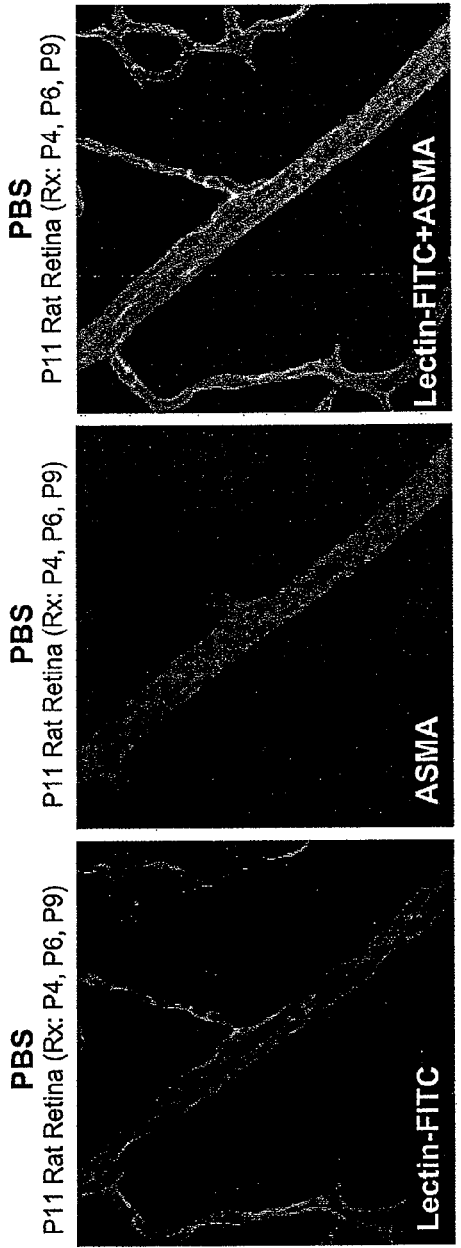

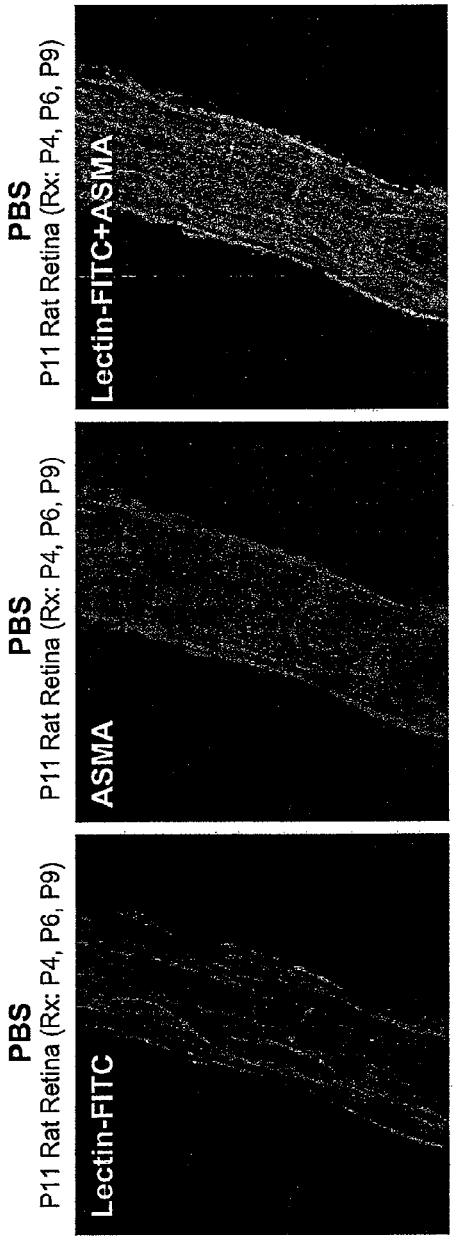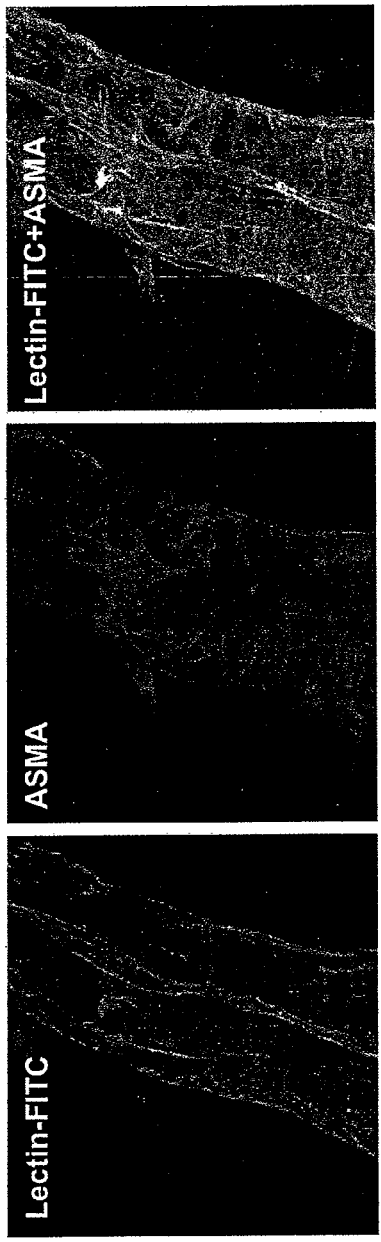

Combination of ALK1.Fc with Anti-VEGF Causes
Dramatic Reduction of Tumor Vascular Density

LL2

LL2

LL2

LL2

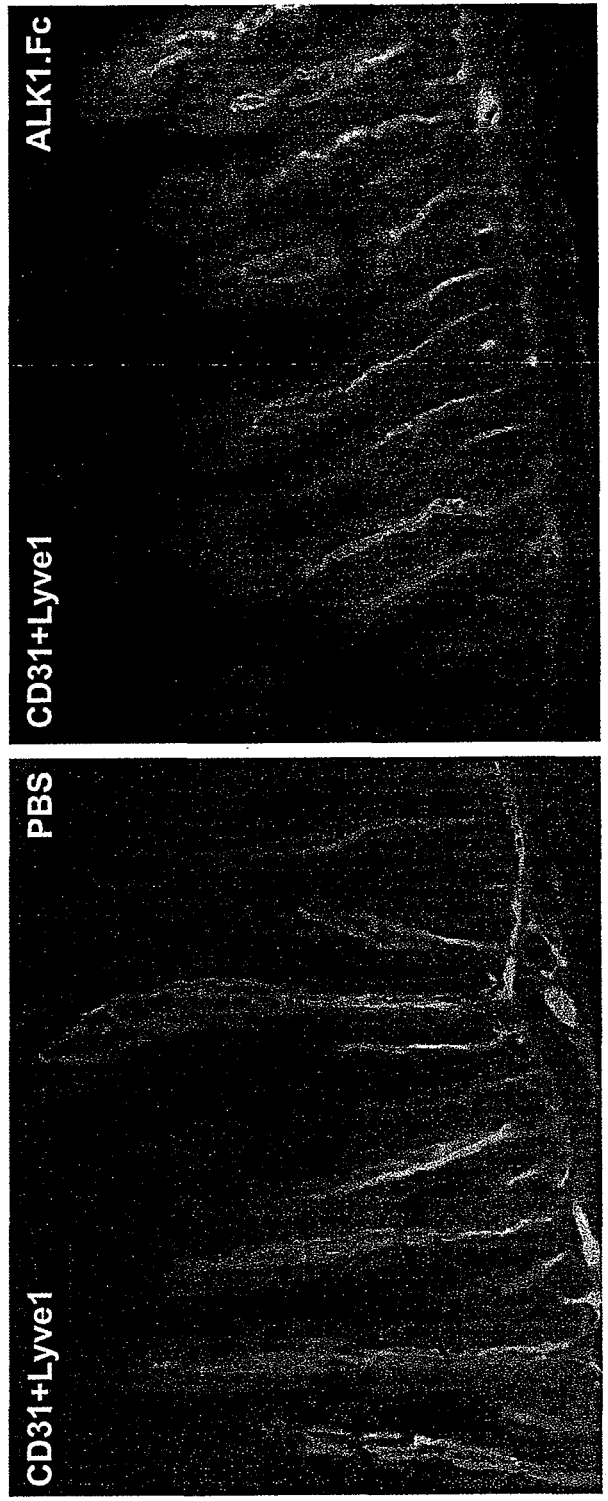

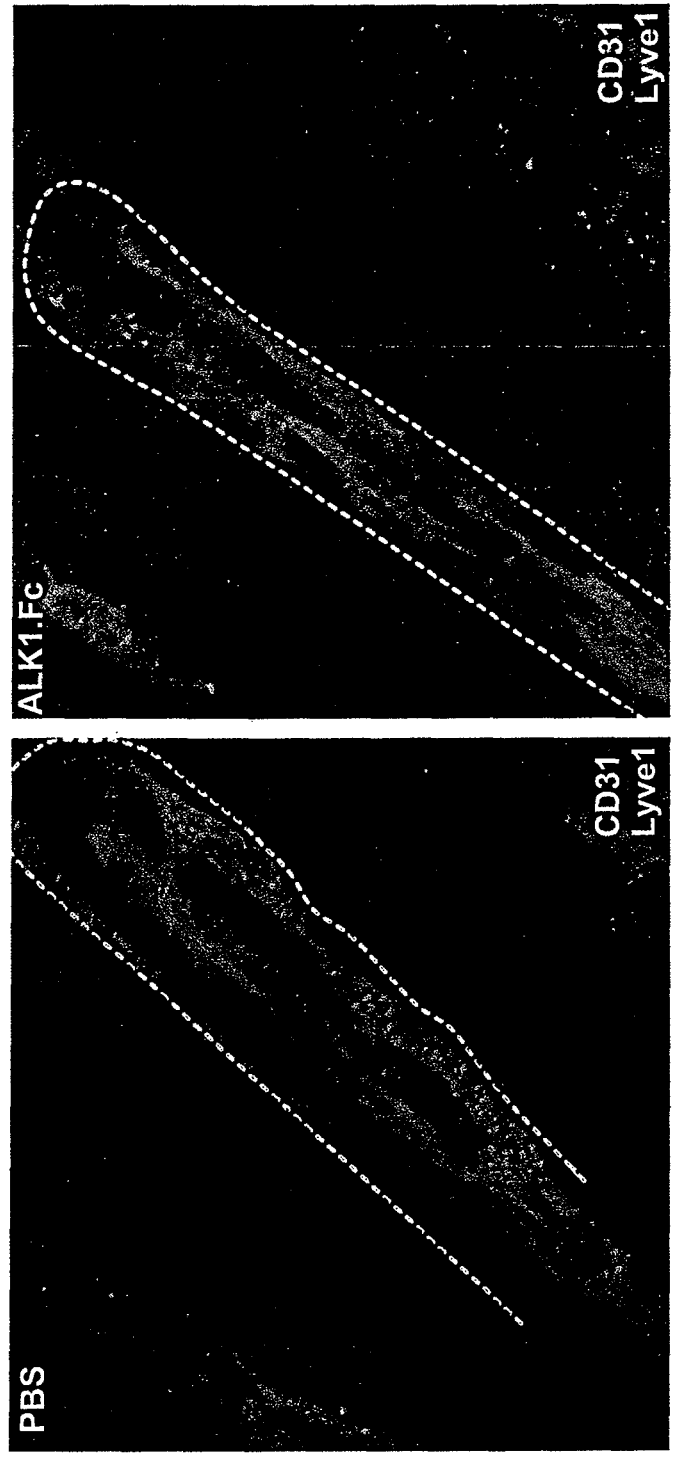

ALK1.Fc Affects the Early Postnatal Development of Lymphatic Vasculature in Mouse Tail Skin
FIG. 12A
P9 Mouse Tail Skin
Rx: P1, P3 & P6 (10mg/ml)
PBS
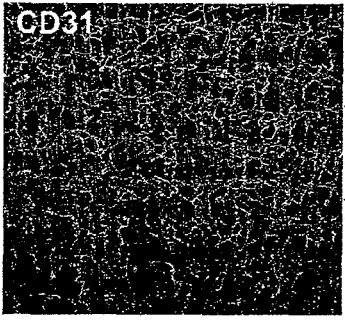
FIG. 12B
P9 Mouse Tail Skin
Rx: P1, P3 & P6 (10mg/ml)
PBS
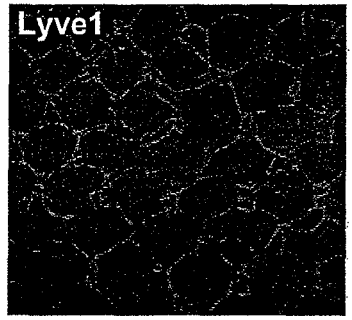
FIG. 12C
P9 Mouse Tail Skin
Rx: P1, P3 & P6 (10mg/ml)
PBS
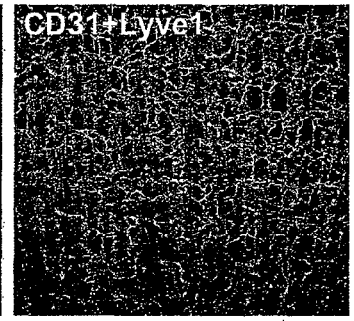
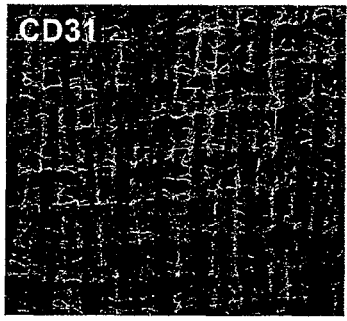
ALK1.Fc
P9 Mouse Tail Skin
Rx: P1, P3 & P6 (10mg/ml)
FIG. 12D
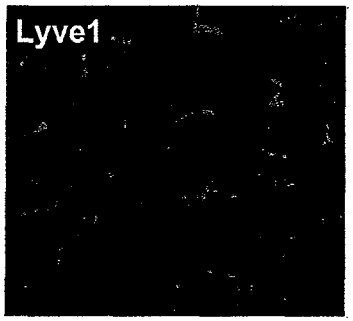
ALK1.Fc
P9 Mouse Tail Skin
Rx: P1, P3 & P6 (10mg/ml)
FIG. 12E
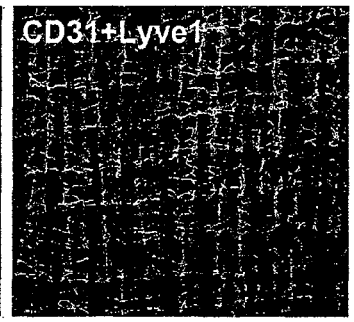
ALK1.Fc
P9 Mouse Tail Skin
Rx: P1, P3 & P6 (10mg/ml)
FIG. 12F

SEQUENCE LISTING

<160> NUMBER OF SEQ ID NOS: 10

<210> SEQ ID NO 1
<211> LENGTH: 1059
<212> TYPE: DNA
<213> ORGANISM: Artificial sequence
<220> FEATURE:
<223> OTHER INFORMATION: sequence is synthesized

<400> SEQUENCE: 1
atgaccttgg gctcccccag gaaaggcctt ctgatgctgc tgatggcctt         50
ggtgacccag ggagaccctg tgaagccgtc tcggggcccg ctggtgacct        100

| | |
|---|---|
| gcacgtgtga gagcccacat tgcaaggggc ctacctgccg gggggcctgg | 150 |
| tgcacagtag tgctggtgcg ggaggagggg aggcacccc aggaacatcg | 200 |
| gggctgcggg aacttgcaca gggagctctg caggggcgc cccaccgagt | 250 |
| tcgtcaacca ctactgctgc gacagccacc tctgcaacca caacgtgtcc | 300 |
| ctggtgctgg aggccaccca acctccttcg gagcagccgg aacagatgg | 350 |
| ccagaccggt gtcaccgaca aagctgcgca ctatactctg tgcccaccgt | 400 |
| gcccagcacc tgaactcctg gggggaccgt cagtcttcct cttccccca | 450 |
| aaacccaagg acaccctcat gatctcccgg accctgagg tcacatgcgt | 500 |
| ggtggtggcc gtgagccacg aagaccctga ggtcaagttc aactggtacg | 550 |
| tggacggcgt ggaggtgcat aatgccaaga caaagccgcg ggaggagcag | 600 |
| tacaacagca cgtaccgtgt ggtcagcgtc ctcaccgtcc tgcaccagga | 650 |
| ctggctgaat ggcaaggagt acaagtgcaa ggtctccaac aaagccctcc | 700 |
| cagcccccat cgagaaaacc atctccaaag ccaaagggca gccccgagaa | 750 |
| ccacaggtgt acaccctgcc cccatcccgg gaagagatga ccaagaacca | 800 |
| ggtcagcctg acctgcctgg tcaaaggctt ctatcccagc gacatcgccg | 850 |
| tggagtggga gagcaatggg cagccggaga caactacaa gaccacgcct | 900 |
| cccgtgctgg actccgacgg ctccttcttc ctctacagca agctcaccgt | 950 |
| ggacaagagc aggtggcagc aggggaacgt cttctcatgc tccgtgatgc | 1000 |
| atgaggctct gcacaaccac tacacgcaga agagcctctc cctgtctccg | 1050 |
| ggtaaatga | 1059 |

<210> SEQ ID NO 2
<211> LENGTH: 352
<212> TYPE: PRT
<213> ORGANISM: Artificial sequence
<220> FEATURE:
<223> OTHER INFORMATION: sequence is synthesized

<400> SEQUENCE: 2

Met Thr Leu Gly Ser Pro Arg Lys Gly Leu Leu Met Leu Leu Met
1               5                   10                  15

Ala Leu Val Thr Gln Gly Asp Pro Val Lys Pro Ser Arg Gly Pro
                20                  25                  30

Leu Val Thr Cys Thr Cys Glu Ser Pro His Cys Lys Gly Pro Thr
                35                  40                  45

Cys Arg Gly Ala Trp Cys Thr Val Val Leu Val Arg Glu Glu Gly
                50                  55                  60

Arg His Pro Gln Glu His Arg Gly Cys Gly Asn Leu His Arg Glu
                65                  70                  75

Leu Cys Arg Gly Arg Pro Thr Glu Phe Val Asn His Tyr Cys Cys
                80                  85                  90

Asp Ser His Leu Cys Asn His Asn Val Ser Leu Val Leu Glu Ala
                95                  100                 105

Thr Gln Pro Pro Ser Glu Gln Pro Gly Thr Asp Gly Gln Thr Gly
                110                 115                 120

Val Thr Asp Lys Ala Ala His Tyr Thr Leu Cys Pro Pro Cys Pro
                125                 130                 135

Ala Pro Glu Leu Leu Gly Gly Pro Ser Val Phe Leu Phe Pro Pro
                140                 145                 150

```
Lys Pro Lys Asp Thr Leu Met Ile Ser Arg Thr Pro Glu Val Thr
            155                 160                 165
Cys Val Val Ala Val Ser His Glu Asp Pro Glu Val Lys Phe
            170                 175                 180
Asn Trp Tyr Val Asp Gly Val Glu Val His Asn Ala Lys Thr Lys
            185                 190                 195
Pro Arg Glu Glu Gln Tyr Asn Ser Thr Tyr Arg Val Val Ser Val
            200                 205                 210
Leu Thr Val Leu His Gln Asp Trp Leu Asn Gly Lys Glu Tyr Lys
            215                 220                 225
Cys Lys Val Ser Asn Lys Ala Leu Pro Ala Pro Ile Glu Lys Thr
            230                 235                 240
Ile Ser Lys Ala Lys Gly Gln Pro Arg Glu Pro Gln Val Tyr Thr
            245                 250                 255
Leu Pro Pro Ser Arg Glu Glu Met Thr Lys Asn Gln Val Ser Leu
            260                 265                 270
Thr Cys Leu Val Lys Gly Phe Tyr Pro Ser Asp Ile Ala Val Glu
            275                 280                 285
Trp Glu Ser Asn Gly Gln Pro Glu Asn Asn Tyr Lys Thr Thr Pro
            290                 295                 300
Pro Val Leu Asp Ser Asp Gly Ser Phe Phe Leu Tyr Ser Lys Leu
            305                 310                 315
Thr Val Asp Lys Ser Arg Trp Gln Gln Gly Asn Val Phe Ser Cys
            320                 325                 330
Ser Val Met His Glu Ala Leu His Asn His Tyr Thr Gln Lys Ser
            335                 340                 345
Leu Ser Leu Ser Pro Gly Lys
            350

<210> SEQ ID NO 3
<211> LENGTH: 1051
<212> TYPE: DNA
<213> ORGANISM: Artificial sequence
<220> FEATURE:
<223> OTHER INFORMATION: sequence is synthesized

<400> SEQUENCE: 3
atgaccttgg gctcccccag gaaaggcctt ctgatgctgc tgatggcctt         50
ggtgacccag ggagaccctg tgaagccgtc tcggggcccg ctggtgacct        100
gcacgtgtga gagcccacat tgcaagggc ctacctgccg ggggcctgg          150 tgcacagtag tgctggtgcg ggaggagggg aggcacccc aggaacatcg         200 gggctgcggg aacttgcaca gggagctctg caggggcgc cccaccgagt         250 tcgtcaacca ctactgctgc gacagccacc tctgcaacca caacgtgtcc        300
ctggtgctgg aggccaccca acctccttcg gagcagccgg aacagatggg        350
ccagaccggt gtcaccgaca aaactcacac atgcccaccg tgcccagcac        400
ctgaactcct gggggaccg tcagtcttcc tcttcccccc aaaacccaag         450 gacacccctca tgatctcccg gacccctgag gtcacatgcg tggtggtgga       500
cgtgagccac gaagaccctg aggtcaagtt caactggtac gtggacggcg       550
tggaggtgca taatgccaag acaaagccgc gggaggagca gtacaacagc       600
acgtaccgtg tggtcagcgt cctcaccgtc ctgcaccagg actggctgaa       650
tggcaaggag tacaagtgca aggtctccaa caaagccctc ccagccccca       700
```

```
tcgagaaaac catctccaaa gccaagggc agccccgaga accacaggtg         750
tacaccctgc cccatcccg ggaagagatg accaagaacc aggtcagcct         800
gacctgcctg gtcaaaggct tctatcccag cgacatcgcc gtggagtggg        850
agagcaatgg gcagccggag aacaactaca gaccacgcc tcccgtgctg         900 gactccgacg gctccttctt cctctacagc aagctcaccg tggacaagag        950
caggtggcag caggggaacg tcttctcatg ctccgtgatg catgaggctc        1000
tgcacaacca ctacacgcag aagagcctct ccctgtctcc gggtaaatga       1050
g                                                             1051
```

```
<210> SEQ ID NO 4
<211> LENGTH: 349
<212> TYPE: PRT
<213> ORGANISM: Artificial sequence
<220> FEATURE:
<223> OTHER INFORMATION: sequence is synthesized

<400> SEQUENCE: 4

Met Thr Leu Gly Ser Pro Arg Lys Gly Leu Leu Met Leu Leu Met
 1               5                  10                  15

Ala Leu Val Thr Gln Gly Asp Pro Val Lys Pro Ser Arg Gly Pro
                20                  25                  30

Leu Val Thr Cys Thr Cys Glu Ser Pro His Cys Lys Gly Pro Thr
                35                  40                  45

Cys Arg Gly Ala Trp Cys Thr Val Val Leu Val Arg Glu Glu Gly
                50                  55                  60

Arg His Pro Gln Glu His Arg Gly Cys Gly Asn Leu His Arg Glu
                65                  70                  75

Leu Cys Arg Gly Arg Pro Thr Glu Phe Val Asn His Tyr Cys Cys
                80                  85                  90

Asp Ser His Leu Cys Asn His Asn Val Ser Leu Val Leu Glu Ala
                95                  100                 105

Thr Gln Pro Pro Ser Glu Gln Pro Gly Thr Asp Gly Gln Thr Gly
                110                 115                 120

Val Thr Asp Lys Thr His Thr Cys Pro Pro Cys Pro Ala Pro Glu
                125                 130                 135

Leu Leu Gly Gly Pro Ser Val Phe Leu Phe Pro Pro Lys Pro Lys
                140                 145                 150

Asp Thr Leu Met Ile Ser Arg Thr Pro Glu Val Thr Cys Val Val
                155                 160                 165

Val Asp Val Ser His Glu Asp Pro Glu Val Lys Phe Asn Trp Tyr
                170                 175                 180

Val Asp Gly Val Glu Val His Asn Ala Lys Thr Lys Pro Arg Glu
                185                 190                 195

Glu Gln Tyr Asn Ser Thr Tyr Arg Val Val Ser Val Leu Thr Val
                200                 205                 210

Leu His Gln Asp Trp Leu Asn Gly Lys Glu Tyr Lys Cys Lys Val
                215                 220                 225

Ser Asn Lys Ala Leu Pro Ala Pro Ile Glu Lys Thr Ile Ser Lys
                230                 235                 240

Ala Lys Gly Gln Pro Arg Glu Pro Gln Val Tyr Thr Leu Pro Pro
                245                 250                 255

Ser Arg Glu Glu Met Thr Lys Asn Gln Val Ser Leu Thr Cys Leu
                260                 265                 270
```

Val Lys Gly Phe Tyr Pro Ser Asp Ile Ala Val Glu Trp Glu Ser
            275                 280                 285

Asn Gly Gln Pro Glu Asn Asn Tyr Lys Thr Thr Pro Pro Val Leu
        290                 295                 300

Asp Ser Asp Gly Ser Phe Phe Leu Tyr Ser Lys Leu Thr Val Asp
    305                 310                 315

Lys Ser Arg Trp Gln Gln Gly Asn Val Phe Ser Cys Ser Val Met
320                 325                 330

His Glu Ala Leu His Asn His Tyr Thr Gln Lys Ser Leu Ser Leu
            335                 340                 345

Ser Pro Gly Lys

<210> SEQ ID NO 5
<211> LENGTH: 1044
<212> TYPE: DNA
<213> ORGANISM: Artificial sequence
<220> FEATURE:
<223> OTHER INFORMATION: sequence is synthesized

<400> SEQUENCE: 5

| | |
|---|---|
| atgaccttgg gctcccccag gaaaggcctt ctgatgctgc tgatggcctt | 50 |
| ggtgacccag ggagaccctg tgaagccgtc tcggggcccg ctggtgacct | 100 |
| gcacgtgtga gagcccacat tgcaaggggc tacctgccg gggggcctgg | 150 |
| tgcacagtag tgctggtgcg ggaggagggg aggcaccccc aggaacatcg | 200 |
| gggctgcggg aacttgcaca gggagctctg caggggcgc cccaccgagt | 250 |
| tcgtcaacca ctactgctgc gacagccacc tctgcaacca caacgtgtcc | 300 |
| ctggtgctgg aggccaccca acctccttcg gagcagccgg aacagatgg | 350 |
| ccagaccggt gacaaaactc acacatgccc accgtgccca gcacctgaac | 400 |
| tcctgggggg accgtcagtc ttcctcttcc ccccaaaacc caaggacacc | 450 |
| ctcatgatct cccggacccc tgaggtcaca tgcgtggtgg tggccgtgag | 500 |
| ccacgaagac cctgaggtca agttcaactg gtacgtggac ggcgtggagg | 550 |
| tgcataatgc caagacaaag ccgcgggagg agcagtacaa cagcacgtac | 600 |
| cgtgtggtca gcgtcctcac cgtcctgcac caggactggc tgaatggcaa | 650 |
| ggagtacaag tgcaaggtct ccaacaaagc cctcccagcc cccatcgaga | 700 |
| aaaccatctc caaagccaaa gggcagcccc gagaaccaca ggtgtacacc | 750 |
| ctgcccccat cccgggaaga gatgaccaag aaccaggtca gcctgacctg | 800 |
| cctggtcaaa ggcttctatc ccagcgacat cgccgtggag tgggagagca | 850 |
| atgggcagcc ggagaacaac tacaagacca cgcctcccgt gctggactcc | 900 |
| gacggctcct tcttcctcta cagcaagctc accgtggaca gagcaggtg | 950 |
| gcagcagggg aacgtcttct catgctccgt gatgcatgag gctctgcaca | 1000 |
| accactacac gcagaagagc ctctccctgt ctccgggtaa atga | 1044 |

<210> SEQ ID NO 6
<211> LENGTH: 347
<212> TYPE: PRT
<213> ORGANISM: Artificial sequence
<220> FEATURE:
<223> OTHER INFORMATION: sequence is synthesized

<400> SEQUENCE: 6

```
Met Thr Leu Gly Ser Pro Arg Lys Gly Leu Leu Met Leu Leu Met
 1               5                  10                  15
Ala Leu Val Thr Gln Gly Asp Pro Val Lys Pro Ser Arg Gly Pro
                20                  25                  30
Leu Val Thr Cys Thr Cys Glu Ser Pro His Cys Lys Gly Pro Thr
                35                  40                  45
Cys Arg Gly Ala Trp Cys Thr Val Val Leu Val Arg Glu Glu Gly
                50                  55                  60
Arg His Pro Gln Glu His Arg Gly Cys Gly Asn Leu His Arg Glu
                65                  70                  75
Leu Cys Arg Gly Arg Pro Thr Glu Phe Val Asn His Tyr Cys Cys
                80                  85                  90
Asp Ser His Leu Cys Asn His Asn Val Ser Leu Val Leu Glu Ala
                95                  100                 105
Thr Gln Pro Pro Ser Glu Gln Pro Gly Thr Asp Gly Gln Thr Gly
                110                 115                 120
Asp Lys Thr His Thr Cys Pro Pro Cys Pro Ala Pro Glu Leu Leu
                125                 130                 135
Gly Gly Pro Ser Val Phe Leu Phe Pro Pro Lys Pro Lys Asp Thr
                140                 145                 150
Leu Met Ile Ser Arg Thr Pro Glu Val Thr Cys Val Val Val Ala
                155                 160                 165
Val Ser His Glu Asp Pro Glu Val Lys Phe Asn Trp Tyr Val Asp
                170                 175                 180
Gly Val Glu Val His Asn Ala Lys Thr Lys Pro Arg Glu Glu Gln
                185                 190                 195
Tyr Asn Ser Thr Tyr Arg Val Val Ser Val Leu Thr Val Leu His
                200                 205                 210
Gln Asp Trp Leu Asn Gly Lys Glu Tyr Lys Cys Lys Val Ser Asn
                215                 220                 225
Lys Ala Leu Pro Ala Pro Ile Glu Lys Thr Ile Ser Lys Ala Lys
                230                 235                 240
Gly Gln Pro Arg Glu Pro Gln Val Tyr Thr Leu Pro Pro Ser Arg
                245                 250                 255
Glu Glu Met Thr Lys Asn Gln Val Ser Leu Thr Cys Leu Val Lys
                260                 265                 270
Gly Phe Tyr Pro Ser Asp Ile Ala Val Glu Trp Glu Ser Asn Gly
                275                 280                 285
Gln Pro Glu Asn Asn Tyr Lys Thr Thr Pro Pro Val Leu Asp Ser
                290                 295                 300
Asp Gly Ser Phe Phe Leu Tyr Ser Lys Leu Thr Val Asp Lys Ser
                305                 310                 315
Arg Trp Gln Gln Gly Asn Val Phe Ser Cys Ser Val Met His Glu
                320                 325                 330
Ala Leu His Asn His Tyr Thr Gln Lys Ser Leu Ser Leu Ser Pro
                335                 340                 345
Gly Lys
```

<210> SEQ ID NO 7
<211> LENGTH: 1053
<212> TYPE: DNA
<213> ORGANISM: Artificial sequence
<220> FEATURE:
<223> OTHER INFORMATION: sequence is synthesized

<400> SEQUENCE: 7

| | | | | | |
|---|---|---|---|---|---|
| atgaccttgg | gctccccag | gaaaggcctt | ctgatgctgc | tgatggcctt | 50 |
| ggtgacccag | ggagaccctg | tgaagccgtc | tcggggcccg | ctggtgacct | 100 |
| gcacgtgtga | gagcccacat | tgcaaggggc | ctacctgccg | ggggggcctgg | 150 |
| tgcacagtag | tgctggtgcg | ggaggagggg | aggcacccc | aggaacatcg | 200 |
| gggctgcggg | aacttgcaca | gggagctctg | caggggcgc | ccaccgagt | 250 |
| tcgtcaacca | ctactgctgc | gacagccacc | tctgcaacca | caacgtgtcc | 300 |
| ctggtgctgg | aggccaccca | acctccttcg | gagcagccgg | aacagatgg | 350 |
| ccaggagccc | aaatcttgtg | acaaaactca | cacatgccca | ccgtgcccag | 400 |
| cacctgaact | cctgggggga | ccgtcagtct | tcctcttccc | cccaaaaccc | 450 |
| aaggacaccc | tcatgatctc | ccggacccct | gaggtcacat | gcgtggtggt | 500 |
| ggacgtgagc | cacgaagacc | ctgaggtcaa | gttcaactgg | tacgtggacg | 550 |
| gcgtggaggt | gcataatgcc | aagacaaagc | cgcgggagga | gcagtacaac | 600 |
| agcacgtacc | gtgtggtcag | cgtcctcacc | gtcctgcacc | aggactggct | 650 |
| gaatggcaag | gagtacaagt | gcaaggtctc | caacaaagcc | ctcccagccc | 700 |
| ccatcgagaa | aaccatctcc | aaagccaaag | ggcagccccg | agaaccacag | 750 |
| gtgtacaccc | tgcccccatc | ccgggaagag | atgaccaaga | accaggtcag | 800 |
| cctgacctgc | ctggtcaaag | gcttctatcc | cagcgacatc | gccgtggagt | 850 |
| gggagagcaa | tgggcagccg | gagaacaact | acaagaccac | gcctcccgtg | 900 |
| ctggactccg | acggctcctt | cttcctctac | agcaagctca | ccgtggacaa | 950 |
| gagcaggtgg | cagcagggga | acgtcttctc | atgctccgtg | atgcatgagg | 1000 |
| ctctgcacaa | ccactacacg | cagaagagcc | tctccctgtc | tccgggtaaa | 1050 | tga  1053

<210> SEQ ID NO 8
<211> LENGTH: 350
<212> TYPE: PRT
<213> ORGANISM: Artificial sequence
<220> FEATURE:
<223> OTHER INFORMATION: sequence is synthesized

<400> SEQUENCE: 8

Met Thr Leu Gly Ser Pro Arg Lys Gly Leu Leu Met Leu Leu Met
 1               5                  10                  15

Ala Leu Val Thr Gln Gly Asp Pro Val Lys Pro Ser Arg Gly Pro
                20                  25                  30

Leu Val Thr Cys Thr Cys Glu Ser Pro His Cys Lys Gly Pro Thr
                35                  40                  45

Cys Arg Gly Ala Trp Cys Thr Val Val Leu Val Arg Glu Glu Gly
                50                  55                  60

Arg His Pro Gln Glu His Arg Gly Cys Gly Asn Leu His Arg Glu
                65                  70                  75

Leu Cys Arg Gly Arg Pro Thr Glu Phe Val Asn His Tyr Cys Cys
                80                  85                  90

Asp Ser His Leu Cys Asn His Asn Val Ser Leu Val Leu Glu Ala
                95                 100                 105

```
Thr Gln Pro Pro Ser Glu Gln Pro Gly Thr Asp Gly Gln Glu Pro
            110                 115                 120

Lys Ser Cys Asp Lys Thr His Thr Cys Pro Pro Cys Pro Ala Pro
            125                 130                 135

Glu Leu Leu Gly Gly Pro Ser Val Phe Leu Phe Pro Pro Lys Pro
            140                 145                 150

Lys Asp Thr Leu Met Ile Ser Arg Thr Pro Glu Val Thr Cys Val
            155                 160                 165

Val Val Asp Val Ser His Glu Asp Pro Glu Val Lys Phe Asn Trp
            170                 175                 180

Tyr Val Asp Gly Val Glu Val His Asn Ala Lys Thr Lys Pro Arg
            185                 190                 195

Glu Glu Gln Tyr Asn Ser Thr Tyr Arg Val Val Ser Val Leu Thr
            200                 205                 210

Val Leu His Gln Asp Trp Leu Asn Gly Lys Glu Tyr Lys Cys Lys
            215                 220                 225

Val Ser Asn Lys Ala Leu Pro Ala Pro Ile Glu Lys Thr Ile Ser
            230                 235                 240

Lys Ala Lys Gly Gln Pro Arg Glu Pro Gln Val Tyr Thr Leu Pro
            245                 250                 255

Pro Ser Arg Glu Glu Met Thr Lys Asn Gln Val Ser Leu Thr Cys
            260                 265                 270

Leu Val Lys Gly Phe Tyr Pro Ser Asp Ile Ala Val Glu Trp Glu
            275                 280                 285

Ser Asn Gly Gln Pro Glu Asn Asn Tyr Lys Thr Thr Pro Pro Val
            290                 295                 300

Leu Asp Ser Asp Gly Ser Phe Phe Leu Tyr Ser Lys Leu Thr Val
            305                 310                 315

Asp Lys Ser Arg Trp Gln Gln Gly Asn Val Phe Ser Cys Ser Val
            320                 325                 330

Met His Glu Ala Leu His Asn His Tyr Thr Gln Lys Ser Leu Ser
            335                 340                 345

Leu Ser Pro Gly Lys
            350

<210> SEQ ID NO 9
<211> LENGTH: 1054
<212> TYPE: DNA
<213> ORGANISM: Artificial sequence
<220> FEATURE:
<223> OTHER INFORMATION: sequence is synthesized

<400> SEQUENCE: 9
atgaccttgg gctcccccag gaaaggcctt ctgatgctgc tgatggcctt         50
ggtgacccag ggagaccctg tgaagccgtc tcggggcccg ctggtgacct        100
gcacgtgtga gagcccacat tgcaaggggc tacctgccgg ggggcctgg         150 tgcacagtag tgctggtgcg ggaggagggg aggcaccccc aggaacatcg        200
gggctgcggg aacttgcaca gggagctctg caggggcgc cccaccgagt         250 tcgtcaacca ctactgctgc gacagccacc tctgcaacca caacgtgtcc        300
ctggtgctgg aggccaccca acctccttcg gagcagccgg aacagatgg         350 ccaggagccc aaatcttctg acaaaactca cacatgccca ccgtgcccag        400
cacctgaact cctgggggga ccgtcagtct tcctcttccc cccaaaaccc        450
```

```
aaggacaccc tcatgatctc ccggacccct gaggtcacat gcgtggtggt        500
ggacgtgagc cacgaagacc ctgaggtcaa gttcaactgg tacgtggacg        550
gcgtggaggt gcataatgcc aagacaaagc cgcgggagga gcagtacaac        600
agcacgtacc gtgtggtcag cgtcctcacc gtcctgcacc aggactggct        650
gaatggcaag gagtacaagt gcaaggtctc caacaaagcc ctcccagccc        700
ccatcgagaa aaccatctcc aaagccaaag ggcagccccg agaaccacag        750
gtgtacaccc tgcccccatc ccgggaagag atgaccaaga accaggtcag        800
cctgacctgc ctggtcaaag gcttctatcc cagcgacatc gccgtggagt        850
gggagagcaa tgggcagccg gagaacaact acaagaccac gcctcccgtg        900
ctggactccg acggctcctt cttcctctac agcaagctca ccgtggacaa        950
gagcaggtgg cagcagggga acgtcttctc atgctccgtg atgcatgagg       1000
ctctgcacaa ccactacacg cagaagagcc tctccctgtc tccgggtaaa       1050
tgag                                                        1054
```

<210> SEQ ID NO 10
<211> LENGTH: 350
<212> TYPE: PRT
<213> ORGANISM: Artificial sequence
<220> FEATURE:
<223> OTHER INFORMATION: sequence is synthesized

<400> SEQUENCE: 10

```
Met Thr Leu Gly Ser Pro Arg Lys Gly Leu Leu Met Leu Leu Met
  1               5                  10                  15

Ala Leu Val Thr Gln Gly Asp Pro Val Lys Pro Ser Arg Gly Pro
                 20                  25                  30

Leu Val Thr Cys Thr Cys Glu Ser Pro His Cys Lys Gly Pro Thr
             35                  40                  45

Cys Arg Gly Ala Trp Cys Thr Val Val Leu Val Arg Glu Glu Gly
         50                  55                  60

Arg His Pro Gln Glu His Arg Gly Cys Gly Asn Leu His Arg Glu
     65                  70                  75

Leu Cys Arg Gly Arg Pro Thr Glu Phe Val Asn His Tyr Cys Cys
         80                  85                  90

Asp Ser His Leu Cys Asn His Asn Val Ser Leu Val Leu Glu Ala
             95                 100                 105

Thr Gln Pro Pro Ser Glu Gln Pro Gly Thr Asp Gly Gln Glu Pro
            110                 115                 120

Lys Ser Ser Asp Lys Thr His Thr Cys Pro Pro Cys Pro Ala Pro
            125                 130                 135

Glu Leu Leu Gly Gly Pro Ser Val Phe Leu Phe Pro Pro Lys Pro
            140                 145                 150

Lys Asp Thr Leu Met Ile Ser Arg Thr Pro Glu Val Thr Cys Val
            155                 160                 165

Val Val Asp Val Ser His Glu Asp Pro Glu Val Lys Phe Asn Trp
            170                 175                 180

Tyr Val Asp Gly Val Glu Val His Asn Ala Lys Thr Lys Pro Arg
            185                 190                 195

Glu Glu Gln Tyr Asn Ser Thr Tyr Arg Val Val Ser Val Leu Thr
            200                 205                 210
```

```
Val Leu His Gln Asp Trp Leu Asn Gly Lys Glu Tyr Lys Cys Lys
            215                 220                 225

Val Ser Asn Lys Ala Leu Pro Ala Pro Ile Glu Lys Thr Ile Ser
            230                 235                 240

Lys Ala Lys Gly Gln Pro Arg Glu Pro Gln Val Tyr Thr Leu Pro
            245                 250                 255

Pro Ser Arg Glu Glu Met Thr Lys Asn Gln Val Ser Leu Thr Cys
            260                 265                 270

Leu Val Lys Gly Phe Tyr Pro Ser Asp Ile Ala Val Glu Trp Glu
            275                 280                 285

Ser Asn Gly Gln Pro Glu Asn Asn Tyr Lys Thr Thr Pro Pro Val
            290                 295                 300

Leu Asp Ser Asp Gly Ser Phe Phe Leu Tyr Ser Lys Leu Thr Val
            305                 310                 315

Asp Lys Ser Arg Trp Gln Gln Gly Asn Val Phe Ser Cys Ser Val
            320                 325                 330

Met His Glu Ala Leu His Asn His Tyr Thr Gln Lys Ser Leu Ser
            335                 340                 345

Leu Ser Pro Gly Lys
            350
```

ACTIVIN RECEPTOR-LIKE KINASE-1 COMPOSITIONS AND METHODS OF USE

RELATED APPLICATION

This application is a continuation application of U.S. application Ser. No. 12/265,154, filed Nov. 5, 2008, which claims priority to United States Provisional Application Ser. Nos. 60/986,876 filed on Nov. 9, 2007 and 61/098,557 filed on Sep. 19, 2008, the entire contents of each of which are incorporated herein by reference in their entirety.

FIELD OF THE INVENTION

The present invention concerns methods and compositions relating to the use of activin receptor-like kinase-1 (ALK-1) antagonists for the treatment of disorders associated with angiogenesis and/or lymphangiogenesis.

BACKGROUND OF THE INVENTION

Development of a vascular supply is a fundamental requirement for many physiological and pathological processes. Actively growing tissues such as embryos and tumors require adequate blood supply. They satisfy this need by producing pro-angiogenic factors, which promote new blood vessel formation via a process called angiogenesis. Vascular tube formation is a complex but orderly biological event involving all or many of the following steps: a) Endothelial cells (ECs) proliferate from existing ECs or differentiate from progenitor cells; b) ECs migrate and coalesce to form cord-like structures; c) vascular cords then undergo tubulogenesis to form vessels with a central lumen; d) existing cords or vessels send out sprouts to form secondary vessels; e) primitive vascular plexus undergo further remodeling and reshaping; and f) peri-endothelial cells are recruited to encase the endothelial tubes, providing maintenance and modulatory functions to the vessels; such cells including pericytes for small capillaries, smooth muscle cells for larger vessels, and myocardial cells in the heart. Hanahan, D. *Science* 277:48-50 (1997); Hogan, B. L. & Kolodziej, P. A. *Nature Reviews Genetics.* 3:513-23 (2002); Lubarsky, B. & Krasnow, M. A. *Cell.* 112:19-28 (2003).

It is now well established that angiogenesis is implicated in the pathogenesis of a variety of disorders. These include solid tumors and metastasis, atherosclerosis, retrolental fibroplasia, hemangiomas, chronic inflammation, intraocular neovascular diseases such as proliferative retinopathies, e.g., diabetic retinopathy, age-related macular degeneration (AMD), neovascular glaucoma, immune rejection of transplanted corneal tissue and other tissues, rheumatoid arthritis, and psoriasis. Folkman et al., *J. Biol. Chem.,* 267:10931-10934 (1992); Klagsbrun et al., *Annu. Rev. Physiol.* 53:217-239 (1991); and Garner A., "Vascular diseases", In: Pathobiology of Ocular Disease. A Dynamic Approach, Garner A., Klintworth G K, eds., 2nd Edition (Marcel Dekker, NY, 1994), pp 1625-1710.

In the case of tumor growth, angiogenesis appears to be crucial for the transition from hyperplasia to neoplasia, and for providing nourishment for the growth and metastasis of the tumor. Folkman et al., *Nature* 339:58 (1989). The neovascularization allows the tumor cells to acquire a growth advantage and proliferative autonomy compared to the normal cells. A tumor usually begins as a single aberrant cell which can proliferate only to a size of a few cubic millimeters due to the distance from available capillary beds, and it can stay 'dormant' without further growth and dissemination for a long period of time. Some tumor cells then switch to the angiogenic phenotype to activate endothelial cells, which proliferate and mature into new capillary blood vessels. These newly formed blood vessels not only allow for continued growth of the primary tumor, but also for the dissemination and recolonization of metastatic tumor cells. Accordingly, a correlation has been observed between density of microvessels in tumor sections and patient survival in breast cancer as well as in several other tumors. Weidner et al., *N. Engl. J. Med* 324:1-6 (1991); Horak et al., *Lancet* 340:1120-1124 (1992); Macchiarini et al., *Lancet* 340:145-146 (1992). The precise mechanisms that control the angiogenic switch is not well understood, but it is believed that neovascularization of tumor mass results from the net balance of a multitude of angiogenesis stimulators and inhibitors (Folkman *Nat Med* 1(1):27-31 (1995)).

It is currently accepted that metastases are responsible for the vast majority, estimated at 90%, of deaths from solid tumors (Gupta and Massague, *Cell* 127, 679-695 (2006)). The complex process of metastasis involves a series of distinct steps including detachment, of tumor cells from the primary tumor, intravasation of tumor cells into lymphatic or blood vessels, and extravasation and growth of tumor cells in secondary sites. Analysis of regional lymph nodes in many tumor types suggests that the lymphatic vasculature is an important route for the dissemination of human cancers. Furthermore, in almost all carcinomas, the presence of tumor cells in lymph nodes is the most important adverse prognostic factor. While it was previously thought that such metastases exclusively involved passage of malignant cells along pre-existing lymphatic vessels near tumors, recent experimental studies and clinicopathological reports (reviewed in Achen et al., *Br J Cancer* 94 (2006), 1355-1360 and Nathanson, *Cancer* 98, 413-423 (2003)) suggest that lymphangiogenesis can be induced by solid tumors and can promote tumor spread. These and other recent studies suggest targeting lymphatics and lymphangiogenesis may be a useful therapeutic strategy to restrict the development of cancer metastasis, which would have a significant benefit for many patients.

SUMMARY OF THE INVENTION

The present invention is based in part on the discovery that agents that modulate the ALK-1 pathway are capable of impairing both angiogenesis and lymphangiogenesis. Treatment with an ALK-1 antagonist resulted in enhanced endothelial cell sprouting, disorganized pericytes, and improper vascular development including tumor and lymphatic vasculature. Tumor models treated with an ALK-1 antagonist resulted in inhibition of tumor growth in several types of cancer. Accordingly, the invention provides methods, compositions, kits and articles of manufacture for disrupting pericytes organization, inhibiting angiogenesis and/or lymphangiogenesis and for use in targeting pathological conditions associated with angiogenesis and/or lymphangiogenesis.

In one aspect the invention provides a method of inhibiting lymphangiogenesis comprising administering to a subject in need of inhibition of lymphangiogenesis an effective amount of an ALK-1 antagonist, whereby the lymphangiogensis is inhibited. In some embodiments the subject suffers from, e.g., a tumor, cancer, cell proliferative disorder, macular degeneration, inflammatory mediated disease, rheumatoid arthritis, diabetic retinopathy or psoriasis. In some embodiments the tumor, cancer or cell proliferative disorder is carcinoma, lymphoma, blastoma, sarcoma, or leukemia.

In another aspect, the invention provides a method for treating a pathological condition associated with lymphangiogenesis in a subject comprising administering to the subject an effective amount of an ALK-1 antagonist, whereby the pathological condition associated with lymphangiogenesis is treated. The pathological condition associated with lymphangiogenesis may be, e.g., a tumor, cancer, cell proliferative disorder, macular degeneration, inflammatory mediated disease, rheumatoid arthritis, diabetic retinopathy or psoriasis. In some embodiments the tumor, cancer or cell proliferative disorder is carcinoma, lymphoma, blastoma, sarcoma, or leukemia.

The invention also provides use of an ALK-1 antagonist in the preparation of a medicament for the therapeutic and/or prophylactic treatment of a disorder, such as a pathological condition associated with angiogenesis or lymphangiogenesis. Such conditions include, for example, a tumor, cancer, cell proliferative disorder, macular degeneration, inflammatory mediated disease, rheumatoid arthritis, diabetic retinopathy or psoriasis. Also provided is the use of an ALK-1 antagonist in the preparation of a medicament for the therapeutic and/or prophylactic treatment of tumor metastasis.

In a further aspect the invention provides a method of inhibiting tumoral lymphangiogenesis in a subject comprising administering to the subject an effective amount of an ALK-1 antagonist, whereby the tumoral lymphangiogensis is inhibited. Also provided is a method of inhibiting or preventing tumor metastasis in a subject comprising administering to the subject an effective amount of an ALK-1 antagonist, whereby the tumor metastasis is inhibited or prevented. In some embodiments the subject has developed or is at risk for developing tumor metastasis. The tumor metastasis may be, for example, in the lymphatic system or in a distant organ.

In another aspect the invention provides a method of disrupting pericyte organization in a subject comprising administering to the subject an effective amount of an ALK-1 antagonist, whereby the pericyte organization is disrupted. In some embodiments the subject suffers from, e.g., a tumor, cancer, cell proliferative disorder, macular degeneration, inflammatory mediated disease, rheumatoid arthritis, diabetic retinopathy or psoriasis. In some embodiments the tumor, cancer or cell proliferative disorder is carcinoma, lymphoma, blastoma, sarcoma, or leukemia.

In yet another aspect, the invention provides a method of inhibiting tumor growth in a subject comprising administering to the subject an effective amount of an ALK-1 antagonist, whereby the tumor growth is inhibited. The invention also provides a method of treating a tumor, cancer or cell proliferative disorder in a subject comprising administering to the subject an effective amount of an ALK-1 antagonist, whereby the tumor, cancer or cell proliferative disorder is treated. In some embodiments, the tumor, cancer or cell proliferative disorder is, e.g., carcinoma, lymphoma, blastoma, sarcoma, or leukemia.

In some embodiments, the methods of the invention further comprise administering to the subject an effective amount of an anti-angiogenesis agent. In some embodiments the anti-angiogenesis agent is an antagonist of vascular endothelial growth factor (VEGF), for example, an anti-VEGF antibody. In some embodiments the anti-VEGF antibody is bevacizumab. In some embodiments, the methods of the invention further comprise administering one or more chemotherapeutic agents.

The invention also provides a method of enhancing efficacy of an anti-angiogenesis agent in a subject having a pathological condition associated with angiogenesis, comprising administering to the subject an effective amount of an ALK-1 antagonist in combination with the anti-angiogenesis agent, thereby enhancing said anti-angiogenesis agent's inhibitory activity. In some embodiments the pathological condition associated with angiogenesis is a tumor, cancer or cell proliferative disorder.

In some embodiments the ALK-1 antagonist is an ALK-1 immunoadhesin. In some embodiments the ALK-1 immunoadhesin comprises amino acid residues 22-352 of SEQ ID NO: 2, residues 22-349 of SEQ ID NO: 4, residues 22-347 of SEQ ID NO: 6, residues 22-350 of SEQ ID NO: 8 or residues 22-350 of SEQ ID NO: 10. In other embodiments the ALK-1 antagonist is an anti-ALK-1 antibody or antigen-binding fragment thereof.

Also provided are ALK-1 antagonists for use in the prevention, inhibition or treatment of tumor metastasis or treatment of tumor, cancer or cell proliferative disorder. The ALK-1 antagonist may be, for example, an ALK-1 immunoadhesin or an anti-ALK-1 antibody or antigen binding fragment thereof. In some embodiments the ALK-1 immunoadhesin comprises amino acid residues 22-352 of SEQ ID NO: 2, residues 22-349 of SEQ ID NO: 4, residues 22-347 of SEQ ID NO: 6, residues 22-350 of SEQ ID NO: 8 or residues 22-350 of SEQ ID NO: 10. The invention also provides a composition for use in treating a tumor, cancer or cell proliferative disorder comprising an effective amount of an ALK-1 antagonist and a pharmaceutically acceptable carrier. In some embodiments the ALK-1 antagonist is an ALK-1 immunoadhesin. In some embodiments the ALK-1 immunoadhesin comprises amino acid residues 22-352 of SEQ ID NO: 2, residues 22-349 of SEQ ID NO: 4, residues 22-347 of SEQ ID NO: 6, residues 22-350 of SEQ ID NO: 8 or residues 22-350 of SEQ ID NO: 10. In some embodiments the ALK-1 antagonist is an anti-ALK-1 antibody:

In one aspect the invention provides an article of manufacture comprising a container and a composition contained within the container, wherein the composition comprises an ALK-1 antagonist. In another aspect the invention provides a kit comprising an ALK-1 antagonist and instructions for using the ALK-1 antagonist. Also provided is a method for preparing a composition comprising admixing a therapeutically effective amount of an ALK-1 antagonist with a pharmaceutically acceptable carrier.

BRIEF DESCRIPTION OF THE DRAWINGS

FIGS. 1A-1B are phase contract microscopy images taken on day 9 of HUVEC sprouting assays in 3-D fibrin gels in the absence (FIG. 1A) or presence. (FIG. 1B) of ALK1.Fc (5 m/ml).

FIGS. 2A-2F are confocal images from rat retinas collected on P11 and stained with anti-CD31 and Lectin-FITC. Neonatal rats were injected i.p. with 10 mg/kg ALK1.Fc or PBS on postnatal day 4 (P4), P6 and P9.

FIGS. 3A-3F are confocal images from rat retinas collected on P11 and stained with Cy3-conjugated anti-alpha smooth muscle actin (ASMA) and Lectin-FITC. Neonatal rats were injected i.p. with 10 mg/kg ALK1.Fc or PBS on P4, P6 and P9.

FIGS. 4A-4F are confocal images from rat retinas collected on P11 and stained with Cy3-conjugated anti-alpha smooth muscle actin (ASMA) and Lectin-FITC. Neonatal rats were injected i.p. with 10 mg/kg ALK1.Fc or PBS on P4, P6 and P9.

FIGS. 10A-10B are confocal images of intestinal villi from neonatal mice treated with PBS (FIG. 10A) or ALK1.Fc (FIG. 10B). The tissues were stained with anti-CD31 to show capillary blood vessels and anti-LYVE-1 to show lymphatic capillaries.

FIGS. 11A-11B are confocal images of a single intestinal villi from neonatal mice treated with PBS (FIG. 11A) or ALK1.Fc (FIG. 11B). The tissues were stained with anti-CD31 to show capillary blood vessels and anti-LYVE-1 to show lymphatic capillaries.

FIGS. 12A-12F are confocal images of mouse tail skin from neonatal mice treated with PBS (FIG. 12A-C) or ALK1.Fc (FIG. 12D-F). The tissues were stained with anti-CD31 to show capillary blood vessels and anti-LYVE-1 to show lymphatic capillaries.

DETAILED DESCRIPTION OF THE INVENTION

Figure 5A:
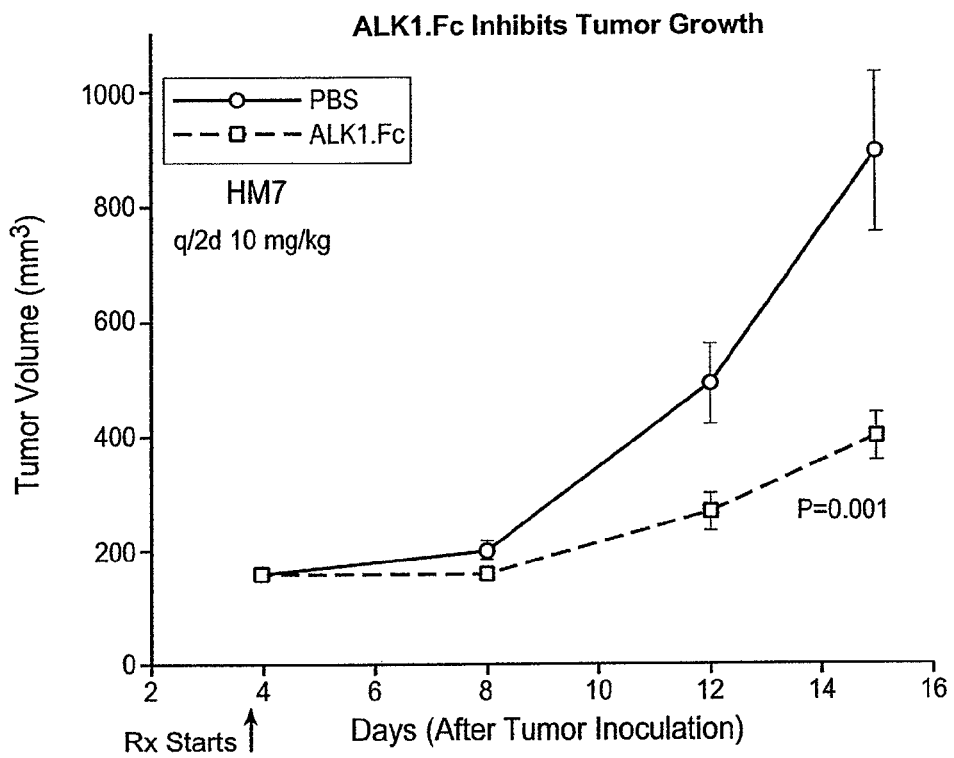
FIGS. 5A-5B are graphs showing that ALK1.Fc (10 mg/kg) inhibits tumor growth in HM7 (FIG. 5A) and MV522 (FIG. 5B) xenografts. Mean tumor volumes with SEs are presented.

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., eds., 1994).

Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (New York, N.Y. 1994), and March, Advanced Organic Chemistry Reactions, Mechanisms and Structure 4th ed., John Wiley & Sons (New York, N.Y. 1992), provide one skilled in the art with a general guide to many of the terms used in the present application.

All references cited herein, including patent applications and publications, are incorporated by reference in their entirety.

DEFINITIONS

The term "ALK-1" (interchangeably termed "activin receptor-like kinase-1"), as used herein, refers, unless specifically or contextually indicated otherwise, to any native or variant (whether native or synthetic) ALK-1 polypeptide. The term "native sequence" specifically encompasses naturally occurring truncated or secreted forms (e.g., an extracellular domain sequence), naturally occurring variant forms (e.g., alternatively spliced forms) and naturally-occurring allelic variants. The term "wild type ALK-1" generally refers to a polypeptide comprising the amino acid sequence of a naturally occurring ALK-1 protein. The term "wild type ALK-1 sequence" generally refers to an amino acid sequence found in a naturally occurring ALK-1.

A "chimeric ALK-1" molecule is a polypeptide comprising full-length ALK-1 or one or more domains thereof fused or bonded to heterologous polypeptide. The chimeric ALK-1 molecule will generally share at least one biological property in common with naturally occurring ALK-1. An example of a chimeric ALK-1 molecule is one that is epitope tagged for purification purposes. Another chimeric ALK-1 molecule is an ALK-1 immunoadhesin.

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence-comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

The term "ALK-1 immunoadhesin" is used interchangeably with the term "ALK-1-immunoglobulin chimera", and refers to a chimeric molecule that combines at least a portion of an ALK-1 molecule (native or variant) with an immunoglobulin sequence. In some instances the ALK-1 immunoadhesin comprises the extracellular domain (ECD) of ALK-1 or a portion thereof sufficient to bind to ALK-1 ligand. In some embodiments the N-terminus of the ALK-1 portion of the ALK-1 immunoadhesin may begin at any amino acid residue from Asp 22 to Ser 27 (inclusive) of SEQ ID NO:2 and the C-terminus of the ALK-1 portion of the ALK-1 immunoadhesin may end at any amino acid residue from Ser 110 to Glu 118 of SEQ DI NO: 2 (inclusive). In some embodiments, the ALK-1 immunoadhesin comprises amino acid residues 1-118 of SEQ ID NO:2. In some embodiments the ALK-1 immunoadhesin comprises amino acid residues 22-118 of SEQ ID NO:2, residues 23-118 of SEQ ID NO: 2, residues 24-118 of SEQ ID NO: 2, residues 25-118 of SEQ ID NO: 2, residues 26-118 of SEQ ID NO: 2, or residues 27-118 of SEQ ID NO: 2. In some embodiments the unprocessed ALK-1 immunoadhesin is ALK1.Fc (SEQ ID NO: 2), ALK1.Fc.2 (SEQ ID NO: 4), ALK1.Fc.3 (SEQ ID NO: 6), ALK1.Fc.4 (SEQ ID NO: 8) or ALK1.Fc.5 (SEQ ID NO: 10). In some embodiments the ALK-1 immunoadhesin comprises amino acid residues 22-352 of SEQ ID NO: 2, residues 22-349 of SEQ ID NO: 4, residues 22-347 of SEQ ID NO: 6, residues 22-350 of SEQ ID NO: 8 or residues 22-350 of SEQ ID NO: 10. The immunoglobulin sequence preferably, but not necessarily, is an immunoglobulin constant domain (Fc region). Immunoadhesins can possess many of the valuable chemical and biological properties of human antibodies. Since immunoadhesins can be constructed from a human protein sequence with a desired specificity linked to an appropriate human immunoglobulin hinge and constant domain (Fc) sequence, the binding specificity of interest can be achieved using entirely human components. Such immunoadhesins are minimally immunogenic to the patient, and are safe for chronic or repeated use. In some embodiments, the Fc region is a native sequence Fc region. In some embodiments, the Fc region is a variant Fc region. In some embodiments, the Fc region is a functional Fc region. The ALK-1 portion and the immunoglobulin sequence portion of the ALK-1 immunoadhesin may be linked by a minimal linker.

Examples of homomultimeric immunoadhesins which have been described for therapeutic use include the CD4-IgG immunoadhesin for blocking the binding of HIV to cell-surface CD4. Data obtained from Phase I clinical trials, in which CD4-IgG was administered to pregnant women just before delivery, suggests that this immunoadhesin may be useful in the prevention of maternal-fetal transfer of HIV (Ashkenazi et al., *Intern. Rev. Immunol.* 10:219-227 (1993)). An immunoadhesin which binds tumor necrosis factor (TNF) has also been developed. TNF is a proinflammatory cytokine which has been shown to be a major mediator of septic shock. Based on a mouse model of septic shock, a TNF receptor immunoadhesin has shown promise as a candidate for clinical use in treating septic shock (Ashkenazi, A. et al. *PNAS USA* 88:10535-10539 (1991)). ENBREL® (etanercept), an immunoadhesin comprising a TNF receptor sequence fused to an IgG Fc region, was approved by the U.S. Food and Drug Administration (FDA), on Nov. 2, 1998, for the treatment of rheumatoid arthritis. The new expanded use of ENBREL® in the treatment of rheumatoid arthritis was approved by FDA on Jun. 6, 2000. For recent information on TNF blockers, including ENBREL®, see Lovell et al., *N. Engl. J. Med.* 342:763-169 (2000), and accompanying editorial on p 810-811; and Weinblatt et al., *N. Engl. J. Med.* 340:253-259 (1999); reviewed in Maini and Taylor, *Annu. Rev. Med.* 51:207-229 (2000).

If the two arms of the immunoadhesin structure have different specificities, the immunoadhesin is called a "bispecific immunoadhesin" by analogy to bispecific antibodies. Dietsch et al., *J. Immunol. Methods* 162:123 (1993) describe such a bispecific immunoadhesin combining the extracellular domains of the adhesion molecules, E-selectin and P-selectin, each of which selectins is expressed in a different cell type in nature. Binding studies indicated that the bispecific immunoglobulin fusion protein so formed had an enhanced ability to bind to a myeloid cell line compared to the monospecific immunoadhesins from which it was derived.

The term "heteroadhesin" is used interchangeably with the expression "chimeric heteromultimer adhesin" and refers to a complex of chimeric molecules (amino acid sequences) in which each chimeric molecule combines a biologically active portion, such as the extracellular domain of each of the heteromultimeric receptor monomers, with a multimerization domain. The "multimerization domain" promotes stable interaction of the chimeric molecules within the heteromultimer complex. The multimerization domains may interact via an immunoglobulin sequence, leucine zipper, a hydrophobic region, a hydrophilic region, or a free thiol that forms an intermolecular disulfide bond between the chimeric molecules of the chimeric heteromultimer. The multimerization domain may comprise an immunoglobulin constant region. In addition a multimerization region may be engineered such that steric interactions not only promote stable interaction, but further promote the formation of heterodimers over homodimers from a mixture of monomers. "Protuberances" are constructed by replacing small amino acid side chains from the interface of the first polypeptide with larger side chains (e.g. tyrosine or tryptophan). Compensatory "cavities" of identical or similar size to the protuberances are optionally created on the interface of the second polypeptide by replacing large amino acid side chains with smaller ones (e.g. alanine or threonine). The immunoglobulin sequence preferably, but not necessarily, is an immunoglobulin constant domain. The immunoglobulin moiety in the chimeras of the present invention may be obtained from $IgG_1$, $IgG_2$, $IgG_3$ or $IgG_4$ subtypes, IgA, IgE, IgD or IgM, but preferably $IgG_1$ or $IgG_3$.

The term "Fc region" herein is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue.

Unless indicated otherwise, herein the numbering of the residues in an immunoglobulin heavy chain is that of the EU index as in Kabat et al., Sequences of Proteins of Immunological Interest, 5th Ed. Public Health Service, National Institutes of Health, Bethesda, Md. (1991), expressly incorporated herein by reference. The "EU index as in Kabat" refers to the residue numbering of the human IgG1 EU antibody.

A "functional Fc region" possesses an "effector function" of a native sequence Fc region. Exemplary "effector functions" include C1q binding; complement dependent cytotoxicity; Fc receptor binding; antibody-dependent cell-mediated cytotoxicity (ADCC); phagocytosis; down regulation of cell surface receptors (e.g. B cell receptor; BCR), etc. Such effector functions generally require the Fc region to be combined with a binding domain (e.g. an antibody variable domain) and can be assessed using various assays as herein disclosed, for example.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and most preferably at least about 90% homology therewith, more preferably at least about 95% homology therewith.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The terms "antibody" and "immunoglobulin" are used interchangeably in the broadest sense and include monoclonal antibodies (for e.g., full length or intact monoclonal antibodies), polyclonal antibodies, multivalent antibodies, multispecific antibodies (e.g., bispecific antibodies so long as they exhibit the desired biological activity) and may also include certain antibody fragments (as described in greater detail herein). An antibody can be human, humanized and/or affinity matured.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-combining sites and is still capable of cross-linking antigen.

"Fv" is the minimum antibody fragment which contains a complete antigen-recognition and -binding site. In a two-chain Fv species, this region consists of a dimer of one heavy- and one light-chain variable domain in tight, non-covalent association. In a single-chain Fv species, one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these can be further divided into subclasses (isotypes), e.g., IgG1, IgG2, IgG3, IgG4, IgA1, and IgA2. The heavy-chain constant domains that correspond to the different classes of immunoglobulins are called α, δ, ε, δ, and μ, respectively. The subunit structures and three-dimensional configurations of different classes of immunoglobulins are well known.

"Antibody fragments" comprise only a portion of an intact antibody, wherein the portion preferably retains at least one, preferably most or all, of the functions normally associated with that portion when present in an intact antibody. Examples of antibody fragments include Fab, Fab', F(ab')2, and Fv fragments; diabodies; linear antibodies; single-chain antibody molecules; and multispecific antibodies formed from antibody fragments. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half life modulation, ADCC function and complement binding. In one embodiment, an antibody fragment is a monovalent antibody that has an in vivo half life substantially similar to an intact antibody. For e.g., such an antibody fragment may comprise on antigen binding arm linked to an Fc sequence capable of conferring in vivo stability to the fragment.

The term "hypervariable region", "HVR", or "HV", when used herein refers to the regions of an antibody variable domain which are hypervariable in sequence and/or form structurally defined loops. Generally, antibodies comprise six hypervariable regions; three in the VH (H1, H2, H3), and three in the VL (L1, L2, L3). A number of hypervariable region delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991)). Chothia refers instead to the location of the structural loops (Chothia and Lesk J. Mol. Biol. 196:901-917 (1987)). The AbM hypervariable regions represent a compromise between the Kabat CDRs and Chothia structural loops, and are used by Oxford Molecular's AbM antibody modeling software. The "contact" hypervariable regions are based on an analysis of the available complex crystal structures. The residues from each of these hypervariable regions are noted below.

| Loop | Kabat | AbM | Chothia | Contact |
|------|-------|-----|---------|---------|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B |
| | | (Kabat Numbering) | | |
| H1 | H31-H35 | H26-H35 | H26-H32 | H30-H35 |
| | | (Chothia Numbering) | | |
| H2 | H50-H65 | H50-H58 | H53-H55 | H47-H58 |
| H3 | H95-H102 | H95-H102 | H96-H101 | H93-H101 |

Hypervariable regions may comprise "extended hypervariable regions" as follows: 24-36 or 24-34 (L1), 46-56 or 50-56 (L2) and 89-97 (L3) in the VL and 26-35 (H1), 50-65 or 49-65 (H2) and 93-102, 94-102 or 95-102 (H3) in the VH. The variable domain residues are numbered according to Kabat et al., supra for each of these definitions.

"Framework" or "FR" residues are those variable domain residues other than the hypervariable region residues as herein defined.

The term "monoclonal antibody" as used herein refers to an antibody from a population of substantially homogeneous antibodies, i.e., the individual antibodies comprising the population are identical and/or bind the same epitope(s), except for possible variants that may arise during production of the monoclonal antibody, such variants generally being present in minor amounts. Such monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones or recombinant DNA clones. It should be understood that the selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations which typically include different antibodies directed against different determinants (epitopes), each monoclonal antibody of a monoclonal antibody preparation is directed against a single determinant on an antigen. In addition to their specificity, the monoclonal antibody preparations are advantageous in that they are typically uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler et al., Nature, 256:495 (1975); Harlow et al., Antibodies: A Laboratory Manual, (Cold Spring Harbor Laboratory Press, 2nd ed. 1988); Hammerling et al., in: Monoclonal Antibodies and T-Cell Hybridomas 563-681, (Elsevier, N.Y., 1981)), recombinant DNA methods (see, e.g., U.S. Pat. No. 4,816,567), phage display technologies (see, e.g., Clackson et al., Nature, 352:624-628 (1991); Marks et al., J. Mol. Biol., 222: 581-597 (1991); Sidhu et al., J. Mol. Biol. 338(2):299-310 (2004); Lee et al., J. Mol. Biol. 340(5):1073-1093 (2004); Fellouse, Proc. Nat. Acad. Sci. USA 101(34):12467-12472 (2004); and Lee et al. J. Immunol. Methods 284(1-2):119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., Proc. Natl. Acad. Sci. USA, 90:2551 (1993); Jakobovits et al., Nature, 362:255-258 (1993); Bruggemann et al., Year in Immuno., 7:33 (1993); U.S. Pat. Nos. 5,545,806; 5,569,825; 5,591,669 (all of GenPharm); 5,545,807; WO 1997/17852; U.S. Pat. Nos. 5,545,807; 5,545,806; 5,569,825; 5,625,126; 5,633,425; and 5,661,016; Marks et al., Bio/Technology, 10: 779-783 (1992); Lonberg et al., Nature, 368: 856-859 (1994); Morrison, Nature, 368: 812-813 (1994); Fishwild et al., Nature Biotechnology, 14: 845-851 (1996); Neuberger, Nature Biotechnology, 14: 826 (1996); and Lonberg and Huszar, Intern. Rev. Immunol., 13: 65-93 (1995).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally will also comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992). See also the following review articles and references cited therein: Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994).

"Chimeric" antibodies (immunoglobulins) have a portion of the heavy and/or light chain identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)). Humanized antibody as used herein is a subset of chimeric antibodies.

"Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv see Pluckthun, in The Pharmacology of Monoclonal Antibodies, vol. 113, Rosenburg and Moore eds., Springer-Verlag, New York, pp. 269-315 (1994).

An "antigen" is a predetermined antigen to which an antibody can selectively bind. The target antigen may be polypeptide, carbohydrate, nucleic acid, lipid, hapten or other naturally occurring or synthetic compound. Preferably, the target antigen is a polypeptide.

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90:6444-6448 (1993).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues.

An "affinity matured" antibody is one with one or more alterations in one or more CDRs thereof which result in an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al. Bio/Technology 10:779-783 (1992) describes affinity maturation by VH and VL domain shuffling. Random mutagenesis of CDR and/or framework residues is described by: Barbas et al. Proc Nat. Acad. Sci, USA 91:3809-3813 (1994); Schier et al. Gene 169:147-155 (1995); Yelton et al. J. Immunol. 155:1994-2004 (1995); Jackson et al., J. Immunol. 154(7):3310-9 (1995); and Hawkins et al, J. Mol. Biol. 226:889-896 (1992).

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g. B cell receptor); and B cell activation.

Antibody-dependent cell-mediated cytotoxicity" or "ADCC" refers to a form of cytotoxicity in which secreted Ig bound onto Fc receptors (FcRs) present on certain cytotoxic cells (e.g. Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol 9:457-92 (1991). To assess ADCC activity of a molecule of interest, an in vitro ADCC assay, such as that described in U.S. Pat. No. 5,500,362 or 5,821,337 or Presta U.S. Pat. No. 6,737,056 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. PNAS (USA) 95:652-656 (1998).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source, e.g. from blood.

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see review M. in Daëron, Annu. Rev. Immunol. 15:203-234 (1997)). FcRs are reviewed in Ravetch and Kinet, Annu. Rev. Immunol 9:457-92 (1991); Capel et al., Immunomethods 4:25-34 (1994); and de Haas et al., J. Lab. Clin. Med. 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., J. Immunol. 117:587 (1976) and Kim et al., J. Immunol. 24:249 (1994)) and regulates homeostasis of immunoglobulins.

WO00/42072 (Presta) describes antibody variants with improved or diminished binding to FcRs. The content of that patent publication is specifically incorporated herein by reference. See, also, Shields et al. J. Biol. Chem. 9(2): 6591-6604 (2001).

Methods of measuring binding to FcRn are known (see, e.g., Ghetie 1997, Hinton 2004). Binding to human FcRn in vivo and serum half life of human FcRn high affinity binding polypeptides can be assayed, e.g., in transgenic mice or transfected human cell lines expressing human FcRn, or in primates administered with the Fc variant polypeptides.

"Complement dependent cytotoxicity" or "CDC" refers to the lysis of a target cell in the presence of complement. Activation of the classical complement pathway is initiated by the binding of the first component of the complement system (C1) to antibodies (of the appropriate subclass) which are bound to their cognate antigen. To assess complement activation, a CDC assay, e.g. as described in Gazzano-Santoro et al., J. 1 mmol. Methods 202:163 (1996), may be performed.

Polypeptide variants with altered Fc region amino acid sequences and increased or decreased C1q binding capability are described in U.S. Pat. No. 6,194,551B1 and WO99/51642. The contents of those patent publications are specifically incorporated herein by reference. See, also, Idusogie et al. J. Immunol. 164: 4178-4184 (2000).

The term "Fc region-comprising polypeptide" refers to a polypeptide, such as an antibody or immunoadhesin, which comprises an Fc region. The C-terminal lysine (residue 447 according to the EU numbering system) of the Fc region may be removed, for example, during purification of the polypeptide or by recombinant engineering the nucleic acid encoding the polypeptide. Accordingly, a composition comprising a polypeptide having an Fc region according to this invention can comprise polypeptides with K447, with all K447 removed, or a mixture of polypeptides with and without the K447 residue.

A "blocking" antibody or an "antagonist" antibody is one which inhibits or reduces biological activity of the antigen it binds. Preferred blocking antibodies or antagonist antibodies substantially or completely inhibit the biological activity of the antigen.

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

A "disorder" or "disease" is any condition that would benefit from treatment with a substance/molecule or method of the invention. This includes chronic and acute disorders or diseases including those pathological conditions which predispose the mammal to the disorder in question. Non-limiting examples of disorders to be treated herein include malignant and benign tumors, carcinoma, blastoma, and sarcoma. Conditions associated with abnormal or excessive lymphangiogenesis include, without limitation, tumors, cancer, cell proliferative disorders, macular degeneration, inflammatory mediated disease, rheumatoid arthritis, diabetic retinopathy and psoriasis.

The terms "cell proliferative disorder" and "proliferative disorder" refer to disorders that are associated with some degree of abnormal cell proliferation. In one embodiment, the cell proliferative disorder is cancer.

"Tumor", as used herein, refers to all neoplastic cell growth and proliferation, whether malignant or benign, and all precancerous and cancerous cells and tissues. The terms "cancer", "cancerous", "cell proliferative disorder", "proliferative disorder" and "tumor" are not mutually exclusive as referred to herein.

The terms "cancer" and "cancerous" refer to or describe the physiological condition in mammals that is typically characterized by unregulated cell growth/proliferation. Examples of cancer include but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, gastric cancer, melanoma, and various types of head and neck cancer. Dysregulation of angiogenesis can lead to many disorders that can be treated by compositions and methods of the invention. These disorders include both non-neoplastic and neoplastic conditions. Neoplastic disorders include but are not limited those described above.

Non-neoplastic disorders include but are not limited to undesired or aberrant hypertrophy, arthritis, rheumatoid arthritis (RA), psoriasis, psoriatic plaques, sarcoidosis, atherosclerosis, atherosclerotic plaques, diabetic and other proliferative retinopathies including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, chronic inflammation, lung inflammation, acute lung injury/ARDS, sepsis, primary pulmonary hypertension, malignant pulmonary effusions, cerebral edema (e.g., associated with acute stroke/closed head injury/trauma), synovial inflammation, pannus formation in RA, myositis ossificans, hypertropic bone formation, osteoarthritis (OA), refractory ascites, polycystic ovarian disease, endometriosis, 3rd spacing of fluid diseases (pancreatitis, compartment syndrome, burns, bowel disease), uterine fibroids, premature labor, chronic inflammation such as IBD (Crohn's disease and ulcerative colitis), renal allograft rejection, inflammatory bowel disease, nephrotic syndrome, undesired or aberrant tissue mass growth (non-cancer), hemophilic joints, hypertrophic scars, inhibition of hair growth, Osler-Weber syndrome, pyogenic granuloma retrolental fibroplasias, scleroderma, trachoma, vascular adhesions, synovitis, dermatitis, preeclampsia, ascites, pericardial effusion (such as that associated with pericarditis), and pleural effusion.

As used herein, "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies are used to delay development of a disease or disorder.

A "subject" is a vertebrate, preferably a mammal, more preferably a human. Mammals include, but are not limited to, farm animals (such as cows and sheep), sport animals, pets (such as cats, dogs and horses), primates, mice and rats.

"Mammal" for purposes of treatment refers to any animal classified as a mammal, including humans, domestic and farm animals, and zoo, sports, or pet animals, such as dogs, horses, cats, cows, etc. Preferably, the mammal is human.

An "effective amount" refers to an amount effective, at dosages and for periods of time necessary, to achieve the desired therapeutic or prophylactic result.

A "therapeutically effective amount" of a substance/molecule may vary according to factors such as the disease state, age, sex, and weight of the individual, and the ability of the substance/molecule, agonist or antagonist to elicit a desired response in the individual. A therapeutically effective amount is also one in which any toxic or detrimental effects of the substance/molecule, agonist or antagonist are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{88}$, $Sm^{153}$, $Bi^{212}$, $P^{32}$ and radioactive isotopes of Lu), chemotherapeutic agents e.g. methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

A "chemotherapeutic agent" is a chemical compound useful in the treatment of cancer. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, Chem. Intl. Ed. Engl., 33: 183-186 (1994)); dynemicin, including dynemicin A; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromethylornithine (DMFO); retinoids such as retinoic acid; capecitabine (XELODA®); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Also included in this definition are anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), EVISTA® raloxifene, droloxifene, 4-hydroxytamoxifen, trioxifene, keoxifene, LY117018, onapristone, and FARESTON® toremifene; anti-progesterones; estrogen receptor down-regulators (ERDs); agents that function to suppress or shut down the ovaries, for example, leutinizing hormone-releasing hormone (LHRH) agonists such as LUPRON® and ELIGARD® leuprolide acetate, goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and AIUMIDEX® anastrozole. In addition, such definition of chemotherapeutic agents includes bisphosphonates such as clodronate (for example, BONEFOS® or OSTAC®), DIDROCAL® etidronate, NE-58095, ZOMETA® zoledronic acid/zoledronate, FOSAMAX® alendronate, AREDIA® pamidronate, SKELID® tiludronate, or ACTONEL® risedronate; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; LURTOTECAN® topoisomerase 1 inhibitor; ABARELIX® rmRH; lapatinib ditosylate (an ErbB-2 and EGFR dual tyrosine kinase small-molecule inhibitor also known as GW572016); and pharmaceutically acceptable salts, acids or derivatives of any of the above.

A "growth inhibitory agent" when used herein refers to a compound or composition which inhibits growth of a cell either in vitro or in vivo. Thus, the growth inhibitory agent may be one which significantly reduces the percentage of cells (such as a cell expressing ALK-1) in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in The Molecular Basis of Cancer, Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

The "pathology" of a disease includes all phenomena that compromise the well-being of the patient. For cancer, this includes, without limitation, abnormal or uncontrollable cell growth, metastasis, interference with the normal functioning of neighboring cells, release of cytokines or other secretory products at abnormal levels, suppression or aggravation of inflammatory or immunological response, etc.

Administration "in combination with" one or more further therapeutic agents includes simultaneous (concurrent) and consecutive administration in any order.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sotbitol; salt-forming counterions such as sodium; and/or nonionic surfactants such as TWEEN™, polyethylene glycol (PEG), and PLURONICS™.

A "liposome" is a small vesicle composed of various types of lipids, phospholipids and/or surfactant which is useful for delivery of a drug (such as a ALK-1 polypeptide or antibody thereto) to a mammal. The components of the liposome are commonly arranged in a bilayer formation, similar to the lipid arrangement of biological membranes.

The terms "VEGF" and "VEGF-A" are used interchangeably to refer to the 165-amino acid vascular endothelial cell growth factor and related 121-, 145-, 183-, 189-, and 206-amino acid vascular endothelial cell growth factors, as described by Leung et al. Science, 246:1306 (1989), Houck et al. Mol. Endocrin., 5:1806 (1991), and, Robinson & Stringer, Journal of Cell Science, 144(5):853-865 (2001), together with the naturally occurring allelic and processed forms thereof.

A "VEGF antagonist" refers to a molecule capable of neutralizing, blocking, inhibiting, abrogating, reducing or interfering with VEGF activities including its binding to one or more VEGF receptors. VEGF antagonists include anti-VEGF antibodies and antigen-binding fragments thereof, receptor molecules and derivatives which bind specifically to VEGF thereby sequestering its binding to one or more receptors, anti-VEGF receptor antibodies and VEGF receptor antagonists such as small molecule inhibitors of the VEGFR tyrosine kinases, and fusions proteins, e.g., VEGF-Trap (Regeneron), VEGF121-gelonin (Peregrine). VEGF antagonists also include antagonist variants of VEGF, antisense molecules directed to VEGF, RNA aptamers, and ribozymes against VEGF or VEGF receptors.

An "anti-VEGF antibody" is an antibody that binds to VEGF with sufficient affinity and specificity. The anti-VEGF antibody can be used as a therapeutic agent in targeting and interfering with diseases or conditions wherein the VEGF activity is involved. See, e.g., U.S. Pat. Nos. 6,582,959, 6,703,020; WO98/45332; WO 96/30046; WO94/10202, WO2005/044853;; EP 0666868B1; US Patent Applications 20030206899, 20030190317, 20030203409, 20050112126, 20050186208, and 20050112126; Popkov et al., Journal of Immunological Methods 288:149-164 (2004); and WO2005012359. An anti-VEGF antibody will usually not bind to other VEGF homologues such as VEGF-B or VEGF-C, nor other growth factors such as P1GF, PDGF or bFGF. The anti-VEGF antibody "Bevacizumab (BV)", also known as "rhuMAb VEGF" or "Avastin®", is a recombinant humanized anti-VEGF monoclonal antibody generated according to Presta et al. Cancer Res. 57:4593-4599 (1997). It comprises mutated human IgG1 framework regions and antigen-binding complementarity-determining regions from the murine anti-hVEGF monoclonal antibody A.4.6.1 that blocks binding of human VEGF to its receptors. Approximately 93% of the amino acid sequence of Bevacizumab, including most of the framework regions, is derived from human IgG1, and about 7% of the sequence is derived from the murine antibody A4.6.1. Bevacizumab has a molecular mass of about 149,000 daltons and is glycosylated. Bevacizumab and other humanized anti-VEGF antibodies, including the anti-VEGF antibody fragment "ranibizumab", also known as "Lucentis®", are further described in U.S. Pat. No. 6,884,879 issued Feb. 26, 2005.

The term "biological activity" and "biologically active" with regard to an ALK-1 polypeptide refer to physical/chemical properties and biological functions associated with ALK-1. In some embodiments, ALK-1 "biological activity" includes one or more of binding to an ALK-1 ligand, e.g., BMP9 and/or BMP10 or activating ALK-1 downstream molecular signaling, e.g., phosphorylation of Smad 1, Smad5 and/or Smad8.

A "ALK-1 antagonist" refers to a molecule capable of neutralizing, blocking, inhibiting, abrogating, reducing or interfering with the activities of a ALK-1 including, for example, reduction or blocking of ALK-1 receptor activation, reduction or blocking of ALK-1 downstream molecular signaling, e.g., phosphorylation of Smad1, Smad5 and/or Smad8, disruption or blocking of ALK-1 ligand (e.g., BMP9 or BMP10) binding to ALK1. ALK-1 antagonists include antibodies and antigen-binding fragments thereof, proteins, peptides, glycoproteins, glycopeptides, glycolipids, polysaccharides, oligosaccharides, nucleic acids, bioorganic molecules, peptidomimetics, pharmacological agents and their metabolites, transcriptional and translation control sequences, and the like. Antagonists also include small molecule inhibitors of a protein, and fusions proteins (including immunoadhesins), receptor molecules and derivatives which bind specifically to protein thereby sequestering its binding to its target, antagonist variants of the protein, siRNA molecules directed to a protein, antisense molecules directed to a protein, RNA aptamers, and ribozymes against a protein. In some embodiments, the ALK-1 antagonist is a molecule which binds to ALK-1 and neutralizes, blocks, inhibits, abrogates, reduces or interferes with a biological activity of ALK-1.

The term "anti-neoplastic composition" refers to a composition useful in treating cancer comprising at least one active therapeutic agent, e.g., "anti-cancer agent". Examples of therapeutic agents (anti-cancer agents, also termed "anti-neoplastic agent" herein) include, but are limited to, e.g., chemotherapeutic agents, growth inhibitory agents, cytotoxic agents, agents used in radiation therapy, anti-angiogenesis agents, apoptotic agents, anti-tubulin agents, toxins, and other-agents to treat cancer, e.g., anti-VEGF neutralizing antibody, VEGF antagonist, anti-HER-2, anti-CD20, an epidermal growth factor receptor (EGFR) antagonist (e.g., a tyrosine kinase inhibitor), HER1/EGFR inhibitor, erlotinib, a COX-2 inhibitor (e.g., celecoxib), interferons, cytokines, antagonists (e.g., neutralizing antibodies) that bind to one or more of the ErbB2, ErbB3, ErbB4, or VEGF receptor(s), inhibitors for receptor tyrosine kinases for platet-derived growth factor (PDGF) and/or stem cell factor (SCF) (e.g., imatinib mesylate (Gleevec Novartis)), TRAIL/Apo2L, and other bioactive and organic chemical agents, etc.

The term "prodrug" as used in this application refers to a precursor or derivative form of a pharmaceutically active substance that is less cytotoxic to tumor cells compared to the parent drug and is capable of being enzymatically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," Directed Drug Delivery, Borchardt et al., (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, beta-lactam-containing prodrugs, optionally substituted phenoxyabetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

An "angiogenic factor or agent" is a growth factor which stimulates the development of blood vessels, e.g., promotes angiogenesis, endothelial cell growth, stability of blood vessels, and/or vasculogenesis, etc. For example, angiogenic factors, include, but are not limited to, e.g., VEGF and members of the VEGF family, PlGF, PDGF family, fibroblast growth factor family (FGFs), TIE ligands (Angiopoietins), ephrins, ANGPTL3, ALK-1, etc. It would also include factors that accelerate wound healing, such as growth hormone, insulin-like growth factor-I (IGF-I), VIGF, epidermal growth factor (EGF), CTGF and members of its family, and TGF-α and TGF-β. See, e.g., Klagsbrun and D'Amore, Annu. Rev. Physiol., 53:217-39 (1991); Streit and Detmar, Oncogene, 22:3172-3179 (2003); Ferrara & Alitalo, Nature Medicine 5(12):1359-1364 (1999); Tonini et al., Oncogene, 22:6549-6556 (2003) (e.g., Table 1 listing angiogenic factors); and, Sato Int. J. Clin. Oncol., 8:200-206 (2003).

An "anti-angiogenesis agent" or "angiogenesis inhibitor" refers to a small molecular weight substance, a polynucleotide (including, e.g., an inhibitory RNA (RNAi or siRNA)), a polypeptide, an isolated protein, a recombinant protein, an antibody, or conjugates or fusion proteins thereof, that inhibits angiogenesis, vasculogenesis, or undesirable vascular permeability, either directly or indirectly. For example, an anti-angiogenesis agent is an antibody or other antagonist to an angiogenic agent as defined above, e.g., antibodies to VEGF, antibodies to VEGF receptors, small molecules that block VEGF receptor signaling (e.g., PTK787/ZK2284, SU6668, SUTENT®/SU11248 (sunitinib malate), AMG706, or those described in, e.g., international patent application WO 2004/113304). Anti-angiogensis agents also include native angiogenesis inhibitors, e.g., angiostatin, endostatin, etc. See, e.g., Klagsbrun and D'Amore, Annu. Rev. Physiol., 53:217-39 (1991); Streit and Detmar, Oncogene, 22:3172-3179 (2003) (e.g., Table 3 listing anti-angiogenic therapy in malignant melanoma); Ferrara & Alitalo, Nature Medicine 5(12):1359-1364 (1999); Tonini et al., Oncogene, 22:6549-6556 (2003) (e.g., Table 2 listing antiangiogenic factors); and, Sato hit. J. Clin. Oncol., 8:200-206 (2003) (e.g., Table 1 lists Anti-angiogenesis agents used in clinical trials).

Methods and Compositions of the Invention

The present invention is based in part on the discovery that agents that modulate the ALK-1 pathway (e.g., an ALK-1 immunoadhesin or anti-ALK-1 antibody) are capable of affecting both angiogenesis as well a lymphangiogenesis. In one aspect the invention provides a method of preventing differentiation of endothelial cells into a more mature stage of differentiation comprising contacting the endothelial cells with an ALK-1 antagonist. The endothelial cells may be any type of endothelial cells, e.g., blood or lymphatic endothelial cells. In another aspect the invention provides a method of disrupting pericyte organization comprising contacting the pericytes with an ALK-1 antagonist. In addition, such agents were found to be able to inhibit tumor growth both as a single agent and in combination with a VEGF antagonist. Accordingly ALK-1 antagonists are useful for pathological conditions and disorders associated with angiogenesis as well as lymphangiogenesis.

It is contemplated that ALK-1 antagonists can be used to treat or prevent various pathological conditions or disorders. The invention encompasses a method of inhibiting lymphangiogenesis using an effective amount of an ALK-1 antagonist such as, without limitation, an ALK-1 immunoadhesin or anti-ALK-1 antibody, to inhibit activation of the ALK-1 receptor pathway. In another aspect the invention provides a method of inhibiting lymphangiogenesis comprising administering an effective amount of an ALK-1 antagonist to a subject in need of such treatment.

Examples of pathological conditions or disorders associated with abnormal lymphangiogenesis include, without limitation, tumor, cancer, tumor or cancer metastasis, cell proliferative disorder, macular degeneration, inflammatory mediated disease, rheumatoid arthritis, diabetic retinopathy and psoriasis. In one aspect the invention provides a method of inhibiting or preventing tumoral lymphangiogenesis in a subject comprising administering to the subject an effective amount of an ALK-1 antagonist. Also provided is a method of inhibiting or preventing tumor metastasis in a subject comprising administering to the subject an effective amount of an ALK-1 antagonist. In some embodiments, the subject may have developed or be at risk for developing tumor metastasis. Such metastasis may be in the lymphatic system or in a distant organ.

The invention provides a method of disrupting pericyte organization in a subject comprising administering to the subject an effective amount of an ALK-1 antagonist. In some embodiments the subject suffers from tumor, cancer, tumor or cancer metastasis, cell proliferative disorder, macular degeneration, inflammatory mediated disease, rheumatoid arthritis, diabetic retinopathy and psoriasis. In some embodiments the disruption of pericyte organization occurs in the tumor vessels of a subject afflicted with neoplastic disease such as a tumor or cancer.

The invention contemplates a method of treating tumor, cancer, cell proliferative disorder and/or neoplastic disorder in a subject comprising administering to the subject an effective amount of an ALK-1 antagonist. In one aspect the invention provides a method of inhibiting tumor growth in a subject comprising administering an effective amount of an ALK-1 antagonist. Examples of neoplastic disorders to be treated with an ALK-1 antagonist include, but are not limited to, those described herein under the terms "cancer" and "cancerous."

Non-neoplastic conditions that are amenable to treatment with ALK-1 antagonists useful in the invention, include but are not limited to, e.g., undesired or aberrant hypertrophy, arthritis, rheumatoid arthritis (RA), psoriasis, psoriatic plaques, sarcoidosis, atherosclerosis, atherosclerotic plaques, edema from myocardial infarction, diabetic and other proliferative retinopathies including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, chronic inflammation, lung inflammation, acute lung injury/ARDS, sepsis, primary pulmonary hypertension, malignant pulmonary effusions, cerebral edema (e.g., associated with acute stroke/closed head injury/trauma), synovial inflammation, pannus formation in RA, myositis ossificans, hypertropic bone formation, osteoarthritis (OA), refractory ascites, polycystic ovarian disease, endometriosis, 3rd spacing of fluid diseases (pancreatitis, compartment syndrome, burns, bowel disease), uterine fibroids, premature labor, chronic inflammation such as IBD (Crohn's disease and ulcerative colitis), renal allograft rejection, inflammatory bowel disease, nephrotic syndrome, undesired or aberrant tissue mass growth (non-cancer), obesity, adipose tissue mass growth, hemophilic joints, hypertrophic scars, inhibition of hair growth, Osler-Weber syndrome, pyogenic granuloma retrolental fibroplasias, scleroderma, trachoma, vascular adhesions, synovitis, dermatitis, preeclampsia, ascites, pericardial effusion (such as that associated with pericarditis), and pleural effusion. Further examples of disorders include an epithelial or cardiac disorder.

Combination Therapies

As indicated above, the invention provides combined therapies in which a ALK-1 antagonist (such as an ALK-1 immunoadhesin or anti-ALK-1 antibody) is administered with another therapy. For example, ALK-1 antagonists are used in combinations with anti-cancer agent or an anti-angiogenesis agent to treat various neoplastic or non-neoplastic conditions. In another example, ALK-1 antagonists are used in combination with anti-lymphangiogenic agents (e.g., a VEGFC antagonist such as an anti-VEGFC antibody). In one embodiment, the neoplastic or non-neoplastic condition is characterized by pathological disorder associated with aberrant or undesired angiogenesis or lymphangiogenesis. The ALK-1 antagonist can be administered serially or in combination with another agent that is effective for those purposes, either in the same composition or as separate compositions. Alternatively, or additionally, multiple inhibitors of ALK-1 can be administered.

The administration of the ALK-1 antagonist and the other therapeutic agent (e.g., anti-cancer agent, anti-angiogenesis agent) can be carried out simultaneously, e.g., as a single composition or as two or more distinct compositions using the same or different administration routes. Alternatively, or additionally, the administration can be done sequentially, in any order. Alternatively, or additionally, the steps can be performed as a combination of both sequentially and simultaneously, in any order.

In certain embodiments, intervals ranging from minutes to days, to weeks to months, can be present between the administrations of the two or more compositions. For example, the anti-cancer agent may be administered first, followed by the ALK-1 antagonist. However, simultaneous administration or administration of the ALK-1 antagonist first is also contemplated. Accordingly, in one aspect, the invention provides methods comprising administration of an ALK-1 antagonist (such as an ALK-1 immunoadhesin or anti-ALK-1 antibody), followed by administration of an anti-angiogenesis agent (such as a VEGF antagonist, e.g., an anti-VEGF antibody). In one embodiment, the anti-angiogenesis agent is an anti-VEGF neutralizing antibody or fragment (e.g., humanized A4.6.1, AVASTIN® (Genentech, South San Francisco, Calif.), Y0317, M4, G6, B20, 2C3, etc.). See, e.g., U.S. Pat. Nos. 6,582,959, 6,884,879, 6,703,020; WO98/45332; WO 96/30046; WO94/10202; EP 0666868B1; US Patent Applications 20030206899, 20030190317, 20030203409, and 20050112126; Popkov et al., Journal of Immunological Methods 288:149-164 (2004); and, WO2005012359.

The effective amounts of therapeutic agents administered in combination with an ALK-1 antagonist will be at the physician's or veterinarian's discretion. Dosage administration and adjustment is done to achieve maximal management of the conditions to be treated. The dose will additionally depend on such factors as the type of therapeutic agent to be used and the specific patient being treated. Suitable dosages for the anti-cancer agent are those presently used and can be lowered due to the combined action (synergy) of the anti-cancer agent and the ALK-1 antagonist. In certain embodiments, the combination of the inhibitors potentiates the efficacy of a single inhibitor. The term "potentiate" refers to an improvement in the efficacy of a therapeutic agent at its common or approved dose. See also the section entitled *Pharmaceutical Compositions* herein.

Typically, the ALK-1 antagonists and anti-cancer agents are suitable for the same or similar diseases to block or reduce a pathological disorder such as a tumor, a cancer or a cell proliferative disorder. In one embodiment the anti-cancer agent is an anti-angiogenesis agent.

Antiangiogenic therapy in relationship to cancer is a cancer treatment strategy aimed at inhibiting the development of tumor blood vessels required for providing nutrients to support tumor growth. Because angiogenesis is involved in both primary tumor growth and metastasis, the antiangiogenic treatment provided by the invention is capable of inhibiting the neoplastic growth of tumor at the primary site as well as preventing metastasis of tumors at the secondary sites, therefore allowing attack of the tumors by other therapeutics.

Many anti-angiogenesis agents have been identified and are known in the arts, including those listed herein, e.g., listed under the Definitions section, and by, e.g., Carmeliet and Jain, Nature 407:249-257 (2000); Ferrara et al., Nature Reviews: Drug Discovery, 3:391-400 (2004); (2004); and Sato Int. J. Clin. Oncol., 8:200-206 (2003). See also, US Patent Application US20030055006. In one embodiment, an ALK-1 antagonist is used in combination with an anti-VEGF neutralizing antibody (or fragment) and/or another VEGF antagonist or a VEGF receptor antagonist including, but not limited to, for example, soluble VEGF receptor (e.g., VEGFR-1, VEGFR-2, VEGFR-3, neuropillins (e.g., NRP1, NRP2)) fragments, aptamers capable of blocking VEGF or VEGFR, neutralizing anti-VEGFR antibodies, low molecule weight inhibitors of VEGFR tyrosine kinases (RTK), antisense strategies for VEGF, ribozymes against VEGF or VEGF receptors, antagonist variants of VEGF; and any combinations thereof. Alternatively, or additionally, two or more angiogenesis inhibitors may optionally be co-administered to the patient in addition to VEGF antagonist and other agent. In certain embodiment, one or more additional therapeutic agents, e.g., anti-cancer agents, can be administered in combination with ALK-1 antagonist, the VEGF antagonist, and an anti-angiogenesis agent.

In certain aspects of the invention, other therapeutic agents useful for combination tumor therapy with an ALK-1 antagonist include other cancer therapies, (e.g., surgery, radiological treatments (e.g., involving irradiation or administration of radioactive substances), chemotherapy, treatment with anticancer agents listed herein and known in the art, or combinations thereof). Alternatively, or additionally, two or more antibodies binding the same or two or more different antigens disclosed herein can be co-administered to the patient. Sometimes, it may be beneficial to also administer one or more cytokines to the patient.

Chemotherapeutic Agents

In one aspect, the invention provides a method of treating a disorder (such as a tumor, a cancer, or a cell proliferative disorder) by administering effective amounts of an ALK-1 antagonist (and/or an angiogenesis inhibitor(s)) and one or more chemotherapeutic agents. A variety of chemotherapeutic agents may be used in the combined treatment methods of the invention. An exemplary and non-limiting list of chemotherapeutic agents contemplated is provided herein under "Definitions." The administration of the ALK-1 antagonist and the chemotherapeutic agent can be done simultaneously, e.g., as a single composition or as two or more distinct compositions, using the same or different administration routes. Alternatively, or additionally, the administration can be done sequentially, in any order. Alternatively, or additionally, the steps can be performed as a combination of both sequentially and simultaneously, in any order. In certain embodiments, intervals ranging from minutes to days, to weeks to months, can be present between the administrations of the two or more compositions. For example, the chemotherapeutic agent may be administered first, followed by the ALK-1 antagonist. However, simultaneous administration or administration of the ALK-1 antagonist prior to administration of the chemotherapeutic agent is also contemplated. Accordingly, in one aspect, the invention provides methods comprising administration of a ALK-1 antagonist (such as an ALK-1 immunoadhesin or anti-ALK-1 antibody), followed by administration of a chemotherapeutic agent.

As will be understood by those of ordinary skill in the art, the appropriate doses of chemotherapeutic agents will be generally around those already employed in clinical therapies wherein the chemotherapeutics are administered alone or in combination with other chemotherapeutics. Variation in dosage will likely occur depending on the condition being treated. The physician administering treatment will be able to determine the appropriate dose for the individual subject.

ALK-1

ALK-1 is an endothelial-specific type I receptor of the TGFβ receptor family. The ALK-1 gene encodes a 503 amino acid polypeptide and includes a hydrophilic cysteine-rich ligand-binding domain, a single hydrophobic transmembrane region and a C-terminal intracellular portion that consists mainly of serine/threonine kinase domains. The accession number of human ALK-1 is CAA80255 and the accession number of mouse ALK-1 is CAA83484.

Mutations in ALK-1 have been associated with hereditary hemorrhagic telangiectasia type 2. For many years ALK-1 was an orphan receptor. Although TGFβ1 and TGFβ3 were previously speculated to be ALK-1 ligands, recently BMP9 and BMP10 have been identified as the physiological ligands of ALK-1 (David, L. et al., Blood 109:1953-1961 (2007)). Activation of ALK-1 has been shown to induce phosphrylation of Smad1, Smad5 and Smad8.

ALK-1 Antagonists

An exemplary and non-limiting list of ALK-1 antagonists (such as an anti-ALK-1 antibody and an ALK-1 immunoadhesin) contemplated is provided herein under "Definitions."

The ALK-1 antagonists useful in the present invention can be characterized for their physical/chemical properties and biological functions by various assays known in the art. In some embodiments, ALK-1 antagonists are characterized for any one or more of: binding to ALK-1, binding to one or more ALK-1 ligands, eg., BMP9 or BMP10, reduction or blocking of ALK-1 receptor activation, reduction or blocking of ALK-1 downstream molecular signaling (e.g., phospharylation of Smad 1, Smad 5 and/or Smad 8), disruption or blocking of BMP9 or BMP10 binding to ALK-1, inhibition of angiogenesis, inhibition of lymphangiogenesis, treatment and/or prevention of a tumor, cell proliferative disorder or a cancer; treatment or prevention of a disorder associated with ALK-1 expression. Methods for characterizing ALK-1 antagonists are known in the art, and some are described and exemplified herein.

ALK-1 Immunoadhesins

Immunoadhesins, including their structure and preparation, are described, e.g. in WO 91/08298; and in U.S. Pat. Nos. 5,428,130 and 5,116,964, the disclosures of which are hereby expressly incorporated by reference.

Production of an Immunoadhesin or Chimeric Heteromultimer Adhesin

The description below relates primarily to production of immunoadhesin by culturing cells transformed or transfected with a vector containing immunoadhesin nucleic acid. It is, of course, contemplated that alternative methods, which are well known in the art, may be employed to prepare immunoadhesins. For instance, the immunoadhesin sequence, or portions thereof, may be produced by direct peptide synthesis using solid-phase techniques (see, e.g., Stewart et al., *Solid-Phase Peptide Synthesis*, W.H. Freeman Co., San Francisco, Calif. (1969); Merrifield, *J. Am. Chem. Soc.*, 85:2149-2154 (1963)). In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the immunoadhesin may be chemically synthesized separately and combined using chemical or enzymatic methods to produce the full-length immunoadhesin.

Nucleic acid encoding a native sequence ALK-1 receptor can, for example, be isolated from cells known to express the ALK-1 receptor. The accession number for human ALK-1 cDNA is Z22533 and the number for mouse ALK-1 cDNA is Z31664.1.

DNA encoding immunoglobulin light or heavy chain constant regions is known or readily available from cDNA libraries or is synthesized. See for example, Adams et al., Biochemistry 19:2711-2719 (1980); Gough et al., Biochemistry 19:2702-2710 (1980); Dolby et al; P.N.A.S. USA, 77:6027-6031 (1980); Rice et al P.N.A.S USA 79:7862-7865 (1982); Falkner et al; Nature 298:286-288 (1982); and Morrison et al; Ann. Rev. Immunol. 2:239-256 (1984).

An immunoadhesin or a chimeric heteroadhesin of the invention is preferably produced by expression in a host cell and isolated therefrom. A host cell is generally transformed with the nucleic acid of the invention. Preferably the nucleic acid is incorporated into an expression vector. Suitable host cells for cloning or expressing the vectors herein include prokaryotic host cells (such as *E. coli*, strains of *Bacillus, Pseudomonas* and other bacteria), yeast and other eukaryotic microbes, and higher eukaryote cells (such as Chinese hamster ovary (CHO) cells and other mammalian cells). The cells may also be present in live animals (for example, in cows, goats or sheep). Insect cells may also be used. Cloning and expression methodologies are well known in the art.

To obtain expression of an immunoadhesin such as the ALK1.Fc molecule (described in detail in Example 1), one or more expression vector(s) is/are introduced into host cells by transformation or transfection and the resulting recombinant host cells are cultured in conventional nutrient media, modified as appropriate for inducing promoters, selecting recombinant cells, or amplifying the ALK1.Fc DNA. In general, principles, protocols, and practical techniques for maximizing the productivity of in vitro mammalian cell cultures can be found in *Mammalian Cell Biotechnology: a Practical Approach*, M. Butler, ed. (IRL Press, 1991).

Construction of Nucleic Acid Encoding Immunoadhesin

When preparing the immunoadhesins of the present invention, preferably nucleic acid encoding an extracellular domain of a natural receptor is fused C-terminally to nucleic acid encoding the N-terminus of an immunoglobulin constant domain sequence, however N-terminal fusions are also possible. Typically, in such fusions the encoded chimeric polypeptide will retain at least functionally active hinge, CH2 and CH3 domains of the constant region of an immunoglobulin heavy chain. Fusions are also made to the C-terminus of the Fc portion of a constant domain, or immediately N-terminal to the CH1 of the heavy chain or the corresponding region of the light chain. The resultant DNA fusion construct is expressed in appropriate host cells.

Nucleic acid molecules encoding amino acid sequence variants of native sequence extracellular domains (such as the extracellular domain from ALK-1) and/or the antibody sequences used to prepare the desired immunoadhesin, are prepared by a variety of methods known in the art. These methods include, but are not limited to, isolation from a natural source or preparation by oligonucleotide-mediated (or site-directed) mutagenesis, PCR mutagenesis, and cassette mutagenesis of an earlier prepared variant or a non-variant version of native sequence ALK-1.

Amino acid sequence variants of native sequence extracellular domain included in the chimeric heteroadhesin are prepared by introducing appropriate nucleotide changes into the native extracellular domain DNA sequence, or by in vitro synthesis of the desired chimeric heteroadhesin monomer polypeptide. Such variants include, for example, deletions from, or insertions or substitutions of, residues in the amino acid sequence of the immunoadhesin or chimeric heteroadhesin.

Variations in the native sequence as described above can be made using any of the techniques and guidelines for conservative and non-conservative mutations.

In one embodiment, the nucleic acid encodes a chimeric molecule in which the ALK-1 receptor extracellular domain sequence is fused to the N-terminus of the C-terminal portion of an antibody (in particular the Fc domain), containing the effector functions of an immunoglobulin, e.g. IgG1. It is possible to fuse the entire heavy chain constant region to the ALK-1 receptor extracellular domain sequence. However, more preferably, a sequence beginning in the hinge region just upstream of the papain cleavage site (which defines IgG Fc chemically; residue 216, taking the first residue of heavy chain constant region to be 114 (Kobet et al., supra), or analogous sites of other immunoglobulins) is used in the fusion. In one embodiment, the ALK-1 receptor extracellular domain sequence is fused to the hinge region and CH2 and CH3 or CH1, hinge, CH2 and CH3 domains of an $IgG_1$, $IgG_2$, or $IgG_3$ heavy chain. The precise site at which the fusion is made is not critical, and the optimal site can be determined by routine experimentation.

For human immunoadhesins, the use of human $IgG_1$ and $IgG_3$ immunoglobulin sequences is preferred. A major advantage of using $IgG_1$ is that $IgG_1$ immunoadhesins can be purified efficiently on immobilized protein A. In contrast, purification of $IgG_3$ requires protein G, a significantly less versatile medium. However, other structural and functional properties of immunoglobulins should be considered when choosing the Ig fusion partner for a particular immunoadhesin construction. For example, the $IgG_3$ hinge is longer and more flexible, so it can accommodate larger "adhesin" domains that may not fold or function properly when fused to $IgG_1$. Another consideration may be valency; IgG immunoadhesins are bivalent homodimers, whereas Ig subtypes like IgA and IgM may give rise to dimeric or pentameric structures, respectively, of the basic Ig homodimer unit.

For ALK-1 immunoadhesins designed for in vivo application, the pharmacokinetic properties and the effector functions specified by the Fc region are important as well. Although $IgG_1$, $IgG_2$ and $IgG_4$ all have in vivo half-lives of 21 days, their relative potencies at activating the complement system are different. $IgG_4$ does not activate complement, and $IgG_2$ is significantly weaker at complement activation than $IgG_1$. Moreover, unlike $IgG_1$, $IgG_2$ does not bind to Fc receptors on mononuclear cells or neutrophils. While $IgG_3$ is optimal for complement activation, its in vivo half-life in approximately one third of the other IgG isotypes.

Another important consideration for immunoadhesins designed to be used as human therapeutics is the number of allotypic variants of the particular isotype. In general, IgG isotypes with fewer serologically-defined allotypes are preferred. For example, $IgG_1$ has only four serologically-defined allotypic sites, two of which (G1m and 2) are located in the Fc region; and one of these sites G1m1, is non-immunogenic. In contrast, there are 0.12 serologically-defined allotypes in $IgG_3$, all of which are in the Fc region; only three of these sites (G3 m5, 11 and 21) have one allotype which is nonimmunogenic. Thus, the potential immunogenicity of an $IgG_3$ immunoadhesin is greater than that of an $IgG_1$ immunoadhesin.

The cDNAs encoding the AKL-1 receptor sequence (e.g. an extracellular domain sequence) and the Ig parts of the immunoadhesin are inserted in tandem into a plasmid vector that directs efficient expression in the chosen host cells. For expression in mammalian cells pRK5-based vectors (Schall et al., Cell 61, 361-370 (1990)) and CDM8-based vectors (Seed, Nature 329, 840 (1989)) may, for example, be used. The exact junction can be created by removing the extra sequences between the designed junction codons using oligonucleotide-directed deletional mutagenesis (Zoller and Smith, Nucleic Acids Res. 10, 6487 (1982); Capon et al., Nature 337, 525-531 (1989)). Synthetic oligonucleotides can be used, in which each half is complementary to the sequence on either side of the desired junction; ideally, these are 36 to 48-mers. Alternatively, PCR techniques can be used to join the two parts of the molecule in-frame with an appropriate vector.

In one embodiment, a chimeric heteroadhesin polypeptide comprises a fusion of a monomer of the chimeric heteroadhesin with a tag polypeptide which provides an epitope to which an anti-tag antibody can selectively bind. Such epitope tagged forms of the chimeric heteroadhesin are useful, as the presence thereof can be detected using a labeled antibody against the tag polypeptide. Also, provision of the epitope tag enables the chimeric heteroadhesin to be readily purified by affinity purification using the anti-tag antibody. Tag polypeptides and their respective antibodies are well known in the art. Examples include the flu HA tag polypeptide and its antibody 12CA5, (Field et al., Mol. Cell. Biol. 8:2159-2165 (1988)); the c-myc tag and the 8F9, 3C7, 6E10, G4, B7 and 9E10 antibodies thereto (Evan et al., Molecular and Cellular Biology 5(12):3610-3616 (1985)); and the Herpes Simplex virus glycoprotein D (gD) tag and its antibody (Paborsky et al., Protein Engineering 3(6):547-553 (1990)).

Another type of covalent modification of a chimeric heteromultimer comprises linking a monomer polypeptide of the heteromultimer to one of a variety of nonproteinaceous polymers, e.g., polyethylene glycol, polypropylene glycol, polyoxyalkylenes, or copolymers of polyethylene glycol and polypropylene glycol. A chimeric heteromultimer also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules), or in macroemulsions. Such techniques are disclosed in *Remington's Pharmaceutical Sciences*, 16th edition, Oslo, A., Ed., (1980).

Selection and Transformation of Host Cells

Host cells are transfected or transformed with expression or cloning vectors described herein for immunoadhesin production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: a Practical Approach*, M. Butler, ed. (IRL Press, 1991) and Sambrook et al., supra.

Following transformation or transfection, the nucleic acid of the invention may integrate into the host cell genome, or may exist as an extrachromosomal element. Methods of eukaryotic cell transfection and prokaryotic cell transformation are known to the ordinarily skilled artisan, for example, $CaCl_2$, $CaPO_4$, liposome-mediated and electroporation. Depending on the host cell used, transformation is performed using standard techniques appropriate to such cells. The calcium treatment employing calcium chloride, as described in Sambrook et al., supra, or electroporation is generally used for prokaryotes. Infection with *Agrobacterium tumefaciens* is used for transformation of certain plant cells, as described by Shaw et al., *Gene*, 23:315 (1983) and WO 89/05859 published 29 Jun. 1989. For mammalian cells without such cell walls, the calcium phosphate precipitation method of Graham and van der Eb, *Virology*, 52:456-457 (1978) can be employed. General aspects of mammalian cell host system transfections have been described in U.S. Pat. No. 4,399,216. Transformations into yeast are typically carried out according to the method of Van Solingen et al., *J. Bact.*, 130:946 (1977) and Hsiao et al., *Proc. Natl. Acad. Sci.* (*USA*), 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., *Methods in Enzymology*, 185:527-537 (1990) and Mansour et al., *Nature*, 336:348-352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635). Other suitable prokaryotic host cells include Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. These examples are illustrative rather than limiting. Strain W3110 is a common host strain for recombinant DNA product fermentation. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonA; *E. coli* W3110 strain 9E4, which has the complete genotype tonA ptr3; *E. coli* W3110 strain 27C7 (ATCC 55,244), which has the complete genotype tonA ptr3 phoA E15 (argF-lac)169 degP ompT $kan^r$; *E. coli* W3110 strain 37D6, which has the complete genotype tonA ptr3 phoA E15 (argF-lac)169 degP ompT rbs7 ilvG $kan^r$; *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued 7 Aug. 1990. Alternatively, in vitro methods of cloning, e.g., PCR or other nucleic acid polymerase reactions, are suitable.

In addition to prokaryotes, eukaryotic microbes such as filamentous fungi or yeast are suitable cloning or expression hosts for immunoadhesin-encoding vectors. *Saccharomyces cerevisiae* is a commonly used lower eukaryotic host microorganism. Others include *Schizosaccharomyces pombe* (Beach and Nurse, *Nature* 290: 140 [1981]; EP 139,383 published 2 May 1985); *Kluyveromyces* hosts (U.S. Pat. No. 4,943,529; Fleer et al., *Bio/Technology*, 9:968-975 (1991))

such as, e.g., *K. lactis* (MW98-8C, CBS683, CBS4574; Louvencourt et al., *J. Bacteriol.*, 154(2): 737-1742 [1983]), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., *Bio/Technology*, 8:135 (1990)), *K. thermotolerans*, and *K. marxianus*; *yarrowia* (EP 402,226); *Pichia pastoris* (EP 183,070; Sreekrishna et al., *J. Basic Microbiol.*, 28:265-278 [1998]); *Candida*; *Trichoderma reesia* (EP 244,234); *Neurospora crassa* (Case et al., *Proc. Natl. Acad. Sci. USA*, 76:5259-5263 [1979]); *Schwanniomyces* such as *Schwanniomyces occidentalis* (EP 394,538 published 31 Oct. 1990); and filamentous fungi such as, e.g., *Neurospora*, *Penicillium*, *Tolypocladium* (WO 91/00357 published 10 Jan. 1991), and *Aspergillus* hosts such as *A. nidulans* (Ballance et al., *Biochem. Biophys. Res. Commun.*, 112:284-289 [1983]; Tilburn et al., *Gene*, 26:205-221 [1983]; Yelton et al., *Proc. Natl. Acad. Sci. USA*, 81: 1470-1474 [1984]) and *A. niger* (Kelly and Hynes, *EMBO J.*, 4:475-479 [1985]). Methylotropic yeasts are, suitable herein and include, but are not limited to, yeast capable of growth on methanol selected from the genera consisting of *Hansenula, Candida, Kloeckera, Pichia, Saccharomyces, Torulopsis*, and *Rhodotorula*. A list of specific species that are exemplary of this class of yeasts may be found in C. Anthony, *The Biochemistry of Methylotrophs*, 269 (1982).

Suitable host cells for the expression of glycosylated immunoadhesin are derived from multicellular organisms. Examples of invertebrate cells include insect cells such as *Drosophila* S2 and *Spodoptera* Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., *J. Gen Virol.*, 36:59 (1977)); Chinese hamster ovary cells/-DHFR (CHO, Urlaub and Chasin, *Proc. Natl. Acad. Sci. USA*, 77:4216 (1980)); mouse sertoli cells (TM4, Mather, *Biol. Reprod.*, 23:243-251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

In general, the choice of a mammalian host cell line for the expression of ALK-1 immunoadhesins depends mainly on the expression vector. Another consideration is the amount of protein that is required. Milligram quantities often can be produced by transient transfections. For example, the adenovirus EIA-transformed 293 human embryonic kidney cell line can be transfected transiently with pRK5-based vectors by a modification of the calcium phosphate method to allow efficient immunoadhesin expression. CDM8-based vectors can be used to transfect COS cells by the DEAE-dextran method (Aruffo et al., Cell 61, 1303-1313 (1990); Zettmeissl et al., DNA Cell Biol. (US) 9, 347-353 (1990)). If larger amounts of protein are desired, the immunoadhesin can be expressed after stable transfection of a host cell line. For example, a pRK5-based vector can be introduced into Chinese hamster ovary (CHO) cells in the presence of an additional plasmid encoding dihydrofolate reductase (DHFR), and conferring resistance to G418. Clones resistant to G418 can be selected in culture; these clones are grown in the presence of increasing levels of DHFR inhibitor methotrexate; clones are selected, in which the number of gene copies encoding the DHFR and immunoadhesin sequences is co-amplified. If the immunoadhesin contains a hydrophobic leader sequence at its N-terminus, it is likely to be processed and secreted by the transfected cells. The expression of immunoadhesins with more complex structures may require uniquely suited host cells; for example, components such as light chain or J chain may be provided by certain myeloma or hybridoma cell hosts (Gascoigne et al., 1987, supra; Martin et al., J. Virol. 67, 3561-3568 (1993)).

Selection and Use of a Replicable Vector

The nucleic acid encoding immunoadhesin may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The immunoadhesin may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the immunoadhesin-encoding DNA that is inserted into the vector. The signal sequence may be a prokaryotic signal sequence selected, for example, from the group of the alkaline phosphatase, penicillinase, 1 pp, or heat-stable enterotoxin II leaders. For yeast secretion the signal sequence may be, e.g., the yeast invertase leader, alpha factor leader (including *Saccharomyces* and *Kluyveromyces* α-factor leaders, the latter described in U.S. Pat. No. 5,010,182), or acid phosphatase leader, the *C. albicans* glucoamylase leader (EP 362,179 published 4 Apr. 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

An example of suitable selectable markers for mammalian cells are those that enable the identification of cells competent to take up the immunoadhesin-encoding nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA*, 77:4216 (1980), A suitable selection gene for use in yeast is the trp1 gene present in the yeast plasmid YR p7 (Stinchcomb et al., *Nature*, 282:39

(1979); Kingsman et al., *Gene,* 7:141 (1979); Tschemper et al., *Gene,* 10:157 (1980)). The trp1 gene provides a selection marker for a mutant strain of yeast lacking the ability to grow in tryptophan, for example, ATCC No. 44076 or PEP4-1 (Jones, *Genetics,* 85:12 (1977)).

Expression and cloning vectors usually contain a promoter operably linked to the immunoadhesin-encoding nucleic acid sequence to direct mRNA synthesis. Promoters recognized by a variety of potential host cells are well known. Promoters suitable for use with prokaryotic hosts include the β-lactamase and lactose promoter systems (Chang et al., *Nature,* 275:615 (1978); Goeddel et al., *Nature,* 281:544 (1979)), alkaline phosphatase, a tryptophan (tip) promoter system (Goeddel, *Nucleic Acids Res.,* 8:4057 (1980); EP 36,776), and hybrid promoters such as the tac promoter (deBoer et al., *Proc. Natl. Acad. Sci. USA,* 80:21-25 (1983)). Promoters for use in bacterial systems also will contain a Shine-Dalgarno sequence operably linked to the DNA encoding immunoadhesin.

Examples of suitable promoter sequences for use with yeast hosts include the promoters for 3-phosphoglycerate kinase (Hitzeman et al., *J. Biol. Chem.,* 255:2073 (1980)) or other glycolytic enzymes (Hess et al., *J. Adv. Enzyme Reg.,* 7:149 (1968); Holland, *Biochemistry,* 17:4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

The transcription of immunoadhesin from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, retrovirus (such as avian sarcoma virus), cytomegalovirus, hepatitis-B virus and Simian Virus 40 (SV40); from heterologous mammalian promoters, e.g., the actin promoter or an immunoglobulin promoter, or from heat-shock promoters, provided such promoters are compatible with the host cell systems.

Transcription of a DNA encoding the immunoadhesin by higher eukaryotes may be increased by inserting an enhancer sequence into the vector. Enhancers are cis-acting elements of DNA, usually about from 10 to 300 bp, which act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (by 100-270), the cytomegalovirus early promoter enhancer, the polyoma enhancer on the late side of the replication origin, and adenovirus enhancers. The enhancer may be spliced into the vector at a position 5' or 3' to the immunoadhesin coding sequence, but is preferably located at a site 5' from the promoter. Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 3' untranslated regions of eukaryotic or viral DNAs or cDNAs. These regions contain nucleotide segments transcribed as polyadenylated fragments in the untranslated portion of the mRNA encoding immunoadhesin.

Still other methods, vectors, and host cells suitable for adaptation to the synthesis of immunoadhesin in recombinant vertebrate cell culture are described in Gething et al., *Nature,* 293:620-625 (1981); Mantei et al., *Nature,* 281:40-46 (1979); EP 117,060; and EP 117,058.

Purification and Characterization of Immunoadhesin

An immunoadhesin or a chimeric heteroadhesin preferably is recovered from the culture medium as a secreted polypeptide, although it also may be recovered from host cell lysates. As a first step, the particulate debris, either host cells or lysed fragments, is removed, for example, by centrifugation or ultrafiltration; optionally, the protein may be concentrated with a commercially available protein concentration filter, followed by separating the chimeric heteroadhesin from other impurities by one or more purification procedures selected from: fractionation on an immunoaffinity column; fractionation on an ion-exchange column; ammonium sulphate or ethanol precipitation; reverse phase HPLC; chromatography on silica; chromatography on heparin Sepharose; chromatography on a cation exchange resin; chromatofocusing; SDS-PAGE; and gel filtration.

A particularly advantageous method of purifying immunoadhesins is affinity chromatography. The choice of affinity ligand depends on the species and isotype of the immunoglobulin Fc domain that is used in the chimera. Protein A can be used to purify immunoadhesins that are based on human $IgG_1$, $IgG_2$, or $IgG_4$ heavy chains (Lindmark et al., J. Immunol. Meth. 62, 1-13 (1983)). Protein G is recommended for all mouse isotypes and for human IgG3 (Guss et al., EMBO J. 5, 15671575 (1986)). The matrix to which the affinity ligand is attached is most often agarose, but other matrices are also available. Mechanically stable matrices such as controlled pore glass or poly(styrenedivinyl)benzene allow for faster flow rates and shorter processing times than can be achieved with agarose. The conditions for binding an immunoadhesin to the protein A or G affinity column are dictated entirely by the characteristics of the Fc domain; that is, its species and isotype. Generally, when the proper ligand is chosen, efficient binding occurs directly from unconditioned culture fluid. One distinguishing feature of immunoadhesins is that, for human $IgG_1$ molecules, the binding capacity for protein A is somewhat diminished relative to an antibody of the same Fc type. Bound immunoadhesin can be efficiently eluted either at acidic pH (at or above 3.0), or in a neutral pH buffer containing a mildly chaotropic salt. This affinity chromatography step can result in an immunoadhesin preparation that is >95% pure.

Other methods known in the art can be used in place of, or in addition to, affinity chromatography on protein A or G to purify immunoadhesins. Immunoadhesins behave similarly to antibodies in thiophilic gel chromatography (Hutchens and Porath, *Anal. Biochem.* 159, 217-226 (1986)) and immobilized metal chelate chromatography (Al-Mashikhi and Makai, *J. Dairy Sci.* 71, 1756-1763 (1988)). In contrast to antibodies, however, their behavior on ion exchange columns is dictated not only by their isoelectric points, but also by a charge dipole that may exist in the molecules due to their chimeric nature.

Preparation of epitope tagged immunoadhesin facilitates purification using an immunoaffinity column containing antibody to the epitope to adsorb the fusion polypeptide.

In some embodiments, the ALK-1 immunoadhesins are assembled as monomers, or hetero-orhomo-multimers, dimers or tetramers, essentially as illustrated in WO 91/08298. Generally, these assembled immunoglobulins will have known unit structures. A basic four chain structural unit is the form in which IgG, IgD, and IgE exist. A four-unit structure is repeated in the higher molecular weight immunoglobulins; IgM generally exists as a pentamer of basic four units held together by disulfide bonds. IgA globulin, and occasionally IgG globulin, may also exist in multimeric form in serum. In the case of multimer, each four unit may be the same or different.

Generally, the ALK-1 immunoadhesins of the invention will have any one or more of the following properties: capable of neutralizing, blocking, inhibiting, abrogating, reducing or interfering with the activities of ALK-1 including, for example, reduction or blocking of ALK-1 receptor activation, reduction or blocking of ALK-1 downstream molecular signaling, e.g., phosphorylation of Smad1, Smad5 and/or Smad8, disruption or blocking of ALK-1 ligand (e.g., BMP9 or BMP10) binding to ALK-1.

Antibodies

In one embodiment the anti-ALK-1 antibodies are monoclonal. Also encompassed within the scope of the invention are Fab, Fab', Fab'-SH and $F(ab')_2$ fragments of the anti-ALK-1 antibodies provided herein. These antibody fragments can be created by traditional means, such as enzymatic digestion, or may be generated by recombinant techniques. Such antibody fragments may be chimeric or humanized. These fragments are useful for the diagnostic and therapeutic purposes set forth below.

Monoclonal antibodies are obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

The anti-ALK-1 monoclonal antibodies can be made using the hybridoma method first described by Kohler et al., Nature, 256:495 (1975), or may be made by recombinant DNA methods (U.S. Pat. No. 4,816,567).

In the hybridoma method, a mouse or other appropriate host animal, such as a hamster, is immunized to elicit lymphocytes that produce or are capable of producing antibodies that will specifically bind to the protein used for immunization. Antibodies to ALK-1 generally are raised in animals by multiple subcutaneous (sc) or intraperitoneal (ip) injections of ALK-1 and an adjuvant. ALK-1 may be prepared using methods well-known in the art, some of which are further described herein. For example, recombinant production of ALK-1 is described below. In one embodiment, animals are immunized with a derivative of ALK-1 that contains the extracellular domain (ECD) of ALK-1 fused to the Fc portion of an immunoglobulin heavy chain. In a another embodiment, animals are immunized with an ALK-1-$IgG_1$ fusion protein. Animals ordinarily are immunized against immunogenic conjugates or derivatives of ALK-1 with monophosphoryl lipid A (MPL)/trehalose dicrynomycolate (TDM) (Ribi Immunochem. Research, Inc., Hamilton, Mont.) and the solution is injected intradermally at multiple sites. Two weeks later the animals are boosted. 7 to 14 days later animals are bled and the serum is assayed for anti-ALK-1 titer. Animals are boosted until titer plateaus.

Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, J. Immunol., 133:3001 (1984); Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against ALK-1. Preferably, the binding specificity of monoclonal antibodies produced by hybridoma cells is determined by immunoprecipitation or by an in vitro binding assay, such as radioimmunoassay (RIA) or enzyme-linked immunoadsorbent assay (ELISA).

The binding affinity of the monoclonal antibody can, for example, be determined by the Scatchard analysis of Munson et al., Anal. Biochem., 107:220 (1980).

After hybridoma cells are identified that produce antibodies of the desired specificity, affinity, and/or activity, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

The anti-ALK-1 antibodies can be made by using combinatorial libraries to screen for synthetic antibody clones with the desired activity or activities. In principle, synthetic antibody clones are selected by screening phage libraries containing phage that display various fragments of antibody variable region (Fv) fused to phage coat protein. Such phage libraries are panned by affinity chromatography against the desired antigen. Clones expressing Fv fragments capable of binding to the desired antigen are adsorbed to the antigen and thus separated from the non-binding clones in the library. The binding clones are then eluted from the antigen, and can be further enriched by additional cycles of antigen adsorption/elution. Any of the anti-ALK-1 antibodies can be obtained by designing a suitable antigen screening procedure to select for the phage clone of interest followed by construction of a full length anti-ALK-1 antibody clone using the Fv sequences from the phage clone of interest and suitable constant region (Fc) sequences described in Kabat et al., Sequences of Proteins of Immunological Interest, Fifth Edition, NIH Publication 91-3242, Bethesda Md. (1991), vols. 1-3.

The antigen-binding domain of an antibody is formed from two variable (V) regions of about 110 amino acids, one each from the light (VL) and heavy (VH) chains, that both present three hypervariable loops or complementarity-determining regions (CDRs). Variable domains can be displayed functionally on phage, either as single-chain Fv (scFv) fragments, in which VH and VL are covalently linked through a short, flexible peptide, or as Fab fragments, in which they are each fused to a constant domain and interact non-covalently, as described in Winter et al., Ann. Rev. Immunol., 12: 433-455 (1994). As used herein, scFv encoding phage clones and Fab encoding phage clones are collectively referred to as "Fv phage clones" or "Fv clones".

Repertoires of VH and VL genes can be separately cloned by polymerase chain reaction (PCR) and recombined randomly in phage libraries, which can then be searched for antigen-binding clones as described in Winter et al., Ann. Rev. Immunol., 12: 433-455 (1994). Libraries from immunized sources provide high-affinity antibodies to the immunogen without the requirement of constructing hybridomas. Alternatively, the naive repertoire can be cloned to provide a single source of human antibodies to a wide range of non-self and also self antigens without any immunization as described by Griffiths et al., EMBO J, 12: 725-734 (1993). Finally, naive libraries can also be made synthetically by cloning the unrearranged V-gene segments from stem cells, and using PCR primers containing random sequence to encode the highly variable CDR3 regions and to accomplish rearrangement in vitro as described by Hoogenboom and Winter, J. Mol. Biol., 227: 381-388 (1992).

Filamentous phage is used to display antibody fragments by fusion to the minor coat protein pIII. The antibody fragments can be displayed as single chain Fv fragments, in which VH and VL domains are connected on the same polypeptide chain by a flexible polypeptide spacer, e.g. as described by Marks et al., J. Mol. Biol., 222: 581-597 (1991), or as Fab fragments, in which one chain is fused to pIII and the other is secreted into the bacterial host cell periplasm where assembly of a Fab-coat protein structure which becomes displayed on the phage surface by displacing some of the wild type coat proteins, e.g. as described in Hoogenboom et al., Nucl. Acids Res., 19: 4133-4137 (1991).

In general, nucleic acids encoding antibody gene fragments are obtained from immune cells harvested from humans or animals. If a library biased in favor of anti-ALK-1 clones is desired, the subject is immunized with ALK-1 to generate an antibody response, and spleen cells and/or circulating B cells other peripheral blood lymphocytes (PBLs) are recovered for library construction. In a preferred embodiment, a human antibody gene fragment library biased in favor of anti-ALK-1 clones is obtained by generating an anti-ALK-1 antibody response in transgenic mice carrying a functional human immunoglobulin gene array (and lacking a functional endogenous antibody production system) such that ALK-1 immunization gives rise to B cells producing human antibodies against ALK-1. The generation of human antibody-producing transgenic mice is described below.

Additional enrichment for anti-ALK-1 reactive cell populations can be obtained, by using a suitable screening procedure to isolate B cells expressing ALK-1-specific membrane bound antibody, e.g., by cell separation with ALK-1 affinity chromatography or adsorption of cells to fluorochrome-labeled ALK-1 followed by flow-activated cell sorting (FACS).

Alternatively, the use of spleen cells and/or B cells or other PBLs from an unimmunized donor provides a better representation of the possible antibody repertoire, and also permits the construction of an antibody library using any animal (human or non-human) species in which ALK-1 is not antigenic. For libraries incorporating in vitro antibody gene construction, stem cells are harvested from the subject to provide nucleic acids encoding unrearranged antibody gene segments. The immune cells of interest can be obtained from a variety of animal species, such as human, mouse, rat, lagomorpha, luprine, canine, feline, porcine, bovine, equine, and avian species, etc.

Nucleic acid encoding antibody variable gene segments (including VH and VL segments) are recovered from the cells of interest and amplified. In the case of rearranged VH and VL gene libraries, the desired DNA can be obtained by isolating genomic DNA or mRNA from lymphocytes followed by polymerase chain reaction (PCR) with primers matching the 5' and 3' ends of rearranged VH and VL genes as described in Orlandi et al., Proc. Natl. Acad. Sci. (USA), 86: 3833-3837 (1989), thereby making diverse V gene repertoires for expression. The V genes can be amplified from cDNA and genomic DNA, with back primers at the 5' end of the exon encoding the mature V-domain and forward primers based within the J-segment as described in Orlandi et al. (1989) and in Ward et al., Nature, 341: 544-546 (1989). However, for amplifying from cDNA, back primers can also be based in the leader exon as described in Jones et al., Biotechnol., 9: 88-89 (1991), and forward primers within the constant region as described in Sastry et al., Proc. Natl. Acad. Sci. (USA), 86: 5728-5732 (1989). To maximize complementarity, degeneracy can be incorporated in the primers as described in Orlandi et al. (1989) or Sastry et al. (1989). Preferably, the library diversity is maximized by using PCR primers targeted to each V-gene family in order to amplify all available VH and VL arrangements present in the immune cell nucleic acid sample, e.g. as described in the method of Marks et al., J. Mol. Biol., 222: 581-597 (1991) or as described in the method of Grum et al., Nucleic Acids Res., 21: 4491-4498 (1993). For cloning of the amplified DNA into expression vectors, rare restriction sites can be introduced within the PCR primer as a tag at one end as described in Orlandi et al. (1989), or by further PCR amplification with a tagged primer as described in Clackson et al., Nature, 352: 624-628 (1991).

Repertoires of synthetically rearranged V genes can be derived in vitro from V gene segments. Most of the human VH-gene segments have been cloned and sequenced (reported in Tomlinson et al., J. Mol. Biol., 227: 776-798 (1992)), and mapped (reported in Matsuda et al., Nature Genet., 3: 88-94 (1993); these cloned segments (including all the major conformations of the H1 and H2 loop) can be used to generate diverse VH gene repertoires with PCR primers encoding H3 loops of diverse sequence and length as described in Hoogenboom and Winter, J. Mol. Biol., 227: 381-388 (1992). VH repertoires can also be made with all the sequence diversity focused in a long H3 loop of a single length as described in Barbas et al., Proc. Natl. Acad. Sci. USA, 89: 4457-4461 (1992). Human Vκ and Vλ segments have been cloned and sequenced (reported in Williams and Winter, Eur. J. Immunol., 23: 1456-1461 (1993)) and can be used to make synthetic light chain repertoires. Synthetic V gene repertoires, based on a range of VH and VL folds, and L3 and H3 lengths, will encode antibodies of considerable structural diversity. Following amplification of V-gene encoding DNAs, germline V-gene segments can be rearranged in vitro according to the methods of Hoogenboom and Winter, J. Mol. Biol., 227: 381-388 (1992).

Repertoires of antibody fragments can be constructed by combining VH and VL gene repertoires together in several ways. Each repertoire can be created in different vectors, and the vectors recombined in vitro, e.g., as described in Hogrefe et al., Gene, 128: 119-126 (1993), or in vivo by combinatorial infection, e.g., the loxP system described in Waterhouse et al., Nucl. Acids Res., 21: 2265-2266 (1993). The in vivo recombination approach exploits the two-chain nature of Fab fragments to overcome the limit on library size imposed by E. coli transformation efficiency. Naive VH and VL repertoires are cloned separately, one into a phagemid and the other into a phage vector. The two libraries are then combined by phage infection of phagemid-containing bacteria so that each cell contains a different combination and the library size is limited only by the number of cells present (about $10^{12}$ clones). Both vectors contain in vivo recombination signals so that the VH and VL genes are recombined onto a single replicon and are co-packaged into phage virions. These huge libraries provide large numbers of diverse antibodies of good affinity ($Kd^{-1}$ of about $10^{-8}$ M).

Alternatively, the repertoires may be cloned sequentially into the same vector, e.g. as described in Barbas et al., Proc. Natl. Acad. Sci. USA, 88: 7978-7982 (1991), or assembled together by PCR and then cloned, e.g. as described in Clackson et al., Nature, 352: 624-628 (1991). PCR assembly can also be used to join VH and VL DNAs with DNA encoding a flexible peptide spacer to form single chain Fv (scFv) repertoires. In yet another technique, "in cell PCR assembly" is used to combine VH and VL genes within lymphocytes by PCR and then clone repertoires of linked genes as described in Embleton et al., Nucl. Acids Res., 20: 3831-3837 (1992).

The antibodies produced by naive libraries (either natural or synthetic) can be of moderate affinity (Kd-1 of about 106 to 107 M-1), but affinity maturation can also be mimicked in vitro by constructing and reselecting from secondary libraries as described in Winter et al. (1994), supra. For example, mutation can be introduced at random in vitro by using error-prone polymerase (reported in Leung et al., Technique, 1: 11-15 (1989)) in the method of Hawkins et al., J. Mol. Biol., 226: 889-896 (1992) or in the method of Gram et al., Proc. Natl. Acad. Sci USA, 89: 3576-3580 (1992). Additionally, affinity maturation can be performed by randomly mutating one or more CDRs, e.g. using PCR with primers carrying random sequence spanning the CDR of interest, in selected individual Fv clones and screening for higher affinity clones. WO 9607754 (published 14 Mar. 1996) described a method for inducing mutagenesis in a complementarity determining region of an immunoglobulin light chain to create a library of light chain genes. Another effective approach is to recombine the VH or VL domains selected by phage display with repertoires of naturally occurring V domain variants obtained from unimmunized donors and screen for higher affinity in several rounds of chain reshuffling as described in Marks et al., Biotechnol., 10: 779-783 (1992). This technique allows the production of antibodies and antibody fragments with affinities in the $10^{-9}$ M range.

ALK-1 nucleic acid and amino acid sequences are known in the art and are further discussed herein. DNAs encoding ALK-1 can be prepared by a variety of methods known in the art. These methods include, but are not limited to, chemical synthesis by any of the methods described in Engels et al., Agnew. Chem. Int. Ed. Engl., 28: 716-734 (1989), such as the triester, phosphite, phosphoramidite and H-phosphonate methods. In one embodiment, codons preferred by the expression host cell are used in the design of the ALK-1 encoding DNA. Alternatively, DNA encoding the ALK-1 can be isolated from a genomic or cDNA library.

Following construction of the DNA molecule encoding the ALK-1, the DNA molecule is operably linked to an expression control sequence in an expression vector, such as a plasmid, wherein the control sequence is recognized by a host cell transformed with the vector. In general, plasmid vectors contain replication and control sequences which are derived from species compatible with the host cell. The vector ordinarily carries a replication site, as well as sequences which encode proteins that are capable of providing phenotypic selection in transformed cells. Suitable vectors for expression in prokaryotic and eukaryotic host cells are known in the art and some are further described herein. Eukaryotic organisms, such as yeasts, or cells derived from multicellular organisms, such as mammals, may be used.

Optionally, the DNA encoding the ALK-1 is operably linked to a secretory leader sequence resulting in secretion of the expression product by the host cell into the culture medium. Examples of secretory leader sequences include stII, ecotin, lamB, herpes GD, 1 pp, alkaline phosphatase, invertase, and alpha factor. Also suitable for use herein is the 36 amino acid leader sequence of protein A (Abrahmsen et al., EMBO J., 4: 3901 (1985)).

Host cells are transfected and preferably transformed with the above-described expression or cloning vectors of this invention and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, $CaPO_4$ precipitation and electroporation. Successful transfection is generally recognized when any indication of the operation of this vector occurs within the host cell. Methods for transfection are well known in the art, and some are further described herein.

Transformation means introducing DNA into an organism so that the DNA is replicable, either as an extrachromosomal element or by chromosomal integrant. Depending on the host cell used, transformation is done using standard techniques appropriate to such cells. Methods for transformation are well known in the art, and some are further described herein.

Prokaryotic host cells used to produce the ALK-1 can be cultured as described generally in Sambrook et al., supra.

The mammalian host cells used to produce the ALK-1 can be cultured in a variety of media, which is well known in the art and some of which is described herein.

The host cells referred to in this disclosure encompass cells in in vitro culture as well as cells that are within a host animal.

Purification of ALK-1 may be accomplished using art-recognized methods, some of which are described herein.

The purified ALK-1 can be attached to a suitable matrix such as agarose beads, acrylamide beads, glass beads, cellulose, various acrylic copolymers, hydroxyl methacrylate gels, polyacrylic and polymethacrylic copolymers, nylon, neutral and ionic carriers, and the like, for use in the affinity chromatographic separation of phage display clones. Attachment of the ALK-1 protein to the matrix can be accomplished by the methods described in Methods in Enzymology, vol. 44 (1976). A commonly employed technique for attaching protein ligands to polysaccharide matrices, e.g. agarose, dextran or cellulose, involves activation of the carrier with cyanogen halides and subsequent coupling of the peptide ligand's primary aliphatic or aromatic amines to the activated matrix.

Alternatively, ALK-1 can be used to coat the wells of adsorption plates, expressed on host cells affixed to adsorption plates or used in cell sorting, or conjugated to biotin for capture with streptavidin-coated beads, or used in any other art-known method for panning phage display libraries.

The phage library samples are contacted with immobilized ALK-1 under conditions suitable for binding of at least a portion of the phage particles with the adsorbent. Normally, the conditions, including pH, ionic strength, temperature and the like are selected to mimic physiological conditions. The phages bound to the solid phase are washed and then eluted by acid, e.g. as described in Barbas et al., Proc. Natl. Acad. Sci. USA, 88: 7978-7982 (1991), or by alkali, e.g. as described in Marks et al., J. Mol. Biol., 222: 581-597 (1991), or by ALK-1 antigen competition, e.g. in a procedure similar to the antigen competition method of Clackson et al., Nature, 352: 624-628 (1991). Phages can be enriched 20-1.000-fold in a single round of selection. Moreover, the enriched phages can be grown in bacterial culture and subjected to further rounds of selection.

The efficiency of selection depends on many factors, including the kinetics of dissociation during washing, and whether multiple antibody fragments on a single phage can simultaneously engage with antigen. Antibodies with fast dissociation kinetics (and weak binding affinities) can be retained by use of short washes, multivalent phage display and high coating density of antigen in solid phase. The high density not only stabilizes the phage through multivalent interactions, but favors rebinding of phage that has dissociated. The selection of antibodies with slow dissociation kinetics (and good binding affinities) can be promoted by use of long washes and monovalent phage display as described in Bass et al., Proteins, 8: 309-314 (1990) and in WO 92/09690, and a low coating density of antigen as described in Marks et al., Biotechnol., 10: 779-783 (1992).

It is possible to select between phage antibodies of different affinities, even with affinities that differ slightly, for ALK-1. However, random mutation of a selected antibody (e.g. as performed in some of the affinity maturation techniques described above) is likely to give rise to many mutants, most binding to antigen, and a few with higher affinity. With limiting ALK-1, rare high affinity phage could be competed out. To retain all the higher affinity mutants, phages can be incubated with excess biotinylated ALK-1, but with the biotinylated ALK-1 at a concentration of lower molarity than the target molar affinity constant for ALK-1. The high affinity-binding phages can then be captured by streptavidin-coated paramagnetic beads. Such "equilibrium capture" allows the antibodies to be selected according to their affinities of binding, with sensitivity that permits isolation of mutant clones with as little as two-fold higher affinity from a great excess of phages with lower affinity. Conditions used in washing phages bound to a solid phase can also be manipulated to discriminate on the basis of dissociation kinetics.

Anti-ALK-1 clones may be activity selected. In one embodiment, the invention provides anti-ALK-1 antibodies that reduce or block ALK-1 receptor activation, reduce or block ALK-1 downstream molecular signaling, e.g., phosphorylation of Smad1, Smad5 and/or Smad8 or disrupt or block ALK-1 ligand (e.g., BMP9 or BMP10) binding to ALK-1.

DNA encoding the hybridoma-derived monoclonal antibodies or phage display Fv clones is readily isolated and sequenced using conventional procedures (e.g. by using oligonucleotide primers designed to specifically amplify the heavy and light chain coding regions of interest from hybridoma or phage DNA template). Once isolated, the DNA can be placed into expression vectors, which are then transfected into host cells such as E. coli cells, simian COS cells, Chinese hamster ovary (CHO) cells, or myeloma cells that do not otherwise produce immunoglobulin protein, to obtain the synthesis of the desired monoclonal antibodies in the recombinant host cells. Review articles on recombinant expression in bacteria of antibody-encoding DNA include Skein et al., Curr. Opinion in Immunol., 5: 256 (1993) and Pluckthun, Immunol. Revs, 130: 151 (1992).

DNA encoding the Fv clones can be combined with known DNA sequences encoding heavy chain and/or light chain constant regions (e.g. the appropriate DNA sequences can be obtained from Kabat et al., supra) to form clones encoding full or partial length heavy and/or light chains. It will be appreciated that constant regions of any isotype can be used for this purpose, including IgG, IgM, IgA, IgD, and IgE constant regions, and that such constant regions can be obtained from any human or animal species. A Fv clone derived from the variable domain DNA of one animal (such as human) species and then fused to constant region DNA of another animal species to form coding sequence(s) for "hybrid", full length heavy chain and/or light chain is included in the definition of "chimeric" and "hybrid" antibody as used herein. In a preferred embodiment, a Fv clone derived from human variable DNA is fused to human constant region DNA to form coding sequence(s) for all human, full or partial length heavy and/or light chains.

DNA encoding anti-ALK-1 antibody derived from a hybridoma can also be modified, for example, by substituting the coding sequence for human heavy- and light-chain constant domains in place of homologous murine sequences derived from the hybridoma clone (e.g. as in the method of Morrison et al., Proc. Natl. Acad. Sci. USA, 81: 6851-6855 (1984)). DNA encoding a hybridoma or Fv clone-derived antibody or fragment can be further modified by covalently joining to the immunoglobulin coding sequence all or part of the coding sequence for a non-immunoglobulin polypeptide. In this manner, "chimeric" or "hybrid" antibodies are prepared that have the binding specificity of the Fv clone or hybridoma clone-derived antibodies.

Antibody Fragments

The present invention encompasses antibody fragments. In certain circumstances there are advantages of using antibody fragments, rather than whole antibodies. The smaller size of the fragments allows for rapid clearance, and may lead to improved access to solid tumors.

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from E. coli, thus allowing the facile production of large amounts of these fragments. Antibody fragments can be isolated from the antibody phage libraries discussed above. Alternatively, Fab'-SH fragments can be directly recovered from E. coli and chemically coupled to form F(ab')$_2$ fragments (Carter et al., Bio/Technology 10:163-167 (1992)). According to another approach, F(ab')$_2$ fragments can be isolated directly from recombinant host cell culture. Fab and F(ab')$_2$ fragment with increased in vivo half-life comprising a salvage receptor binding epitope residues are described in U.S. Pat. No. 5,869,046. Other techniques for the production of antibody fragments will be apparent to the skilled practitioner. In other embodiments, the antibody of choice is a single chain Fv fragment (scFv). See WO 93/16185; U.S. Pat. Nos. 5,571,894; and 5,587,458. Fv and sFv are the only species with intact combining sites that are devoid of constant regions;

thus, they are suitable for reduced nonspecific binding during in vivo use. sFv fusion proteins may be constructed to yield fusion of an effector protein at either the amino or the carboxy terminus of an sFv. See Antibody Engineering, ed. Borrebaeck, supra. The antibody fragment may also be a "linear antibody", e.g., as described in U.S. Pat. No. 5,641,870 for example. Such linear antibody fragments may be monospecific or bispecific.

Humanized Antibodies

The present invention encompasses humanized antibodies. Various methods for humanizing non-human antibodies are known in the art. For example, a humanized antibody can have one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al. (1986) Nature 321:522-525; Riechmann et al. (1988) Nature 332:323-327; Verhoeyen et al. (1988) Science 239:1534-1536), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework for the humanized antibody (Sims et al. (1993) J. Immunol. 151:2296; Chothia et al. (1987) J. Mol. Biol. 196:901. Another method uses a particular framework derived from the consensus sequence of all human antibodies of a particular subgroup of light or heavy chains. The same framework may be used for several different humanized antibodies (Carter et al. (1992) Proc. Natl. Acad. Sci. USA, 89:4285; Presta et al. (1993) J. Immunol., 151:2623.

It is further important that antibodies be humanized with retention of high affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Human Antibodies

Human anti-ALK-1 antibodies can be constructed by combining Fv clone variable domain sequence(s) selected from human-derived phage display libraries with known human constant domain sequences(s) as described above. Alternatively, human monoclonal anti-ALK-1 antibodies can be made by the hybridoma method. Human myeloma and mouse-human heteromyeloma cell lines for the production of human monoclonal antibodies have been described, for example, by Kozbor J. Immunol., 133: 3001 (1984); Brodeur et al., Monoclonal Antibody Production Techniques and Applications, pp. 51-63 (Marcel Dekker, Inc., New York, 1987); and Boerner et al., J. Immunol., 147: 86 (1991).

It is now possible to produce transgenic animals (e.g. mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germline mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., Proc. Natl. Acad. Sci. USA, 90: 2551 (1993); Jakobovits et al., Nature, 362: 255 (1993); Bruggermann et al., Year in Immunol., 7: 33 (1993).

Gene shuffling can also be used to derive human antibodies from non-human, e.g. rodent, antibodies, where the human antibody has similar affinities and specificities to the starting non-human antibody. According to this method, which is also called "epitope imprinting", either the heavy or light chain variable region of a non-human antibody fragment obtained by phage display techniques as described above is replaced with a repertoire of human V domain genes, creating a population of non-human chain/human chain scFv or Fab chimeras. Selection with antigen results in isolation of a non-human chain/human chain chimeric scFv or Fab wherein the human chain restores the antigen binding site destroyed upon removal of the corresponding non-human chain in the primary phage display clone, i.e. the epitope governs (imprints) the choice of the human chain partner. When the process is repeated in order to replace the remaining non-human chain, a human antibody is obtained (see PCT WO 93/06213 published Apr. 1, 1993). Unlike traditional humanization of non-human antibodies by CDR grafting, this technique provides completely human antibodies, which have no FR or CDR residues of non-human origin.

Bispecific Antibodies

Bispecific antibodies are monoclonal, preferably human or humanized, antibodies that have binding specificities for at least two different antigens. In the present case, one of the binding specificities is for ALK-1 and the other is for any other antigen. Exemplary bispecific antibodies may bind to two different epitopes of the ALK-1 protein. Bispecific antibodies may also be used to localize cytotoxic agents to cells which express ALK-1. These antibodies possess an ALK-1-binding arm and an arm which binds the cytotoxic agent (e.g. saporin, anti-interferon-α, vinca alkaloid, ricin A chain, methotrexate or radioactive isotope hapten). Bispecific antibodies can be prepared as full length antibodies or antibody fragments (e.g. F(ab')2 bispecific antibodies).

Methods for making bispecific antibodies are known in the art. Traditionally, the recombinant production of bispecific antibodies is based on the co-expression of two immunoglobulin heavy chain-light chain pairs, where the two heavy chains have different specificities (Milstein and Cuello, Nature, 305: 537 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in WO 93/08829 published May 13, 1993, and in Traunecker et al., EMBO J., 10: 3655 (1991).

According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1), containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology, 121:210 (1986).

According to another approach, the interface between a pair of antibody molecules can be engineered to maximize the percentage of heterodimers which are recovered from recombinant cell culture. The preferred interface comprises at least a part of the CH3 domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676, 980), and for treatment of HIV infection (WO 91/00360, WO 92/00373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science, 229:. 81 (1985) describe a procedure wherein intact antibodies are proteolytically cleaved to generate F(ab')2 fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from E. coli, which can be chemically coupled to form bispecific antibodies. Shalaby et al., J. Exp. Med., 175: 217-225 (1992) describe the production of a fully humanized bispecific antibody F(ab')2 molecule. Each Fab' fragment was separately secreted from E. coli and subjected to directed chemical coupling in vitro to form the bispecific antibody. The bispecific antibody thus formed was able to bind to cells overexpressing the HER2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol., 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA, 90:6444-6448 (1993) has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See Gruber et al., J. Immunol., 152:5368 (1994).

Antibodies with more than two valencies are contemplated. For example, trispecific antibodies can be prepared. Tutt et al. J. Immunol. 147: 60 (1991).

Multivalent Antibodies

A multivalent antibody may be internalized (and/or catabolized) faster than a bivalent antibody by a cell expressing an antigen to which the antibodies bind. The antibodies of the present invention can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1-(X1)n-VD2-(X2)n-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

Antibody Variants

In some embodiments, amino acid sequence modification(s) of the antibodies described herein are contemplated. For example, it may be desirable to improve the binding affinity and/or other biological properties of the antibody. Amino acid sequence variants of the antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics. The amino acid alterations may be introduced in the subject antibody amino acid sequence at the time that sequence is made.

A useful method for identification of certain residues or regions of the antibody that are preferred locations for mutagenesis is called "alanine scanning mutagenesis" as described by Cunningham and Wells (1989) Science, 244: 1081-1085. Here, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed immunoglobulins are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody to an enzyme (e.g. for ADEPT) or a polypeptide which increases the serum half-life of the antibody.

Glycosylation of polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Where the antibody comprises an Fc region, the carbohydrate attached thereto may be altered. For example, antibodies with a mature carbohydrate structure that lacks fucose attached to an Fc region of the antibody are described in US Pat Appl No US 2003/0157108 (Presta, L.). See also US 2004/0093621 (Kyowa Hakko Kogyo Co., Ltd). Antibodies with a bisecting N-acetylglucosamine (GlcNAc) in the carbohydrate attached to an Fc region of the antibody are referenced in WO 2003/011878, Jean-Mairet et al. and U.S. Pat. No. 6,602,684, Umana et al. Antibodies with at least one galactose residue in the oligosaccharide attached to an Fc region of the antibody are reported in WO 1997/30087, Patel et al. See, also, WO 1998/58964 (Raju, S.) and WO 1999/22764 (Raju, S.) concerning antibodies with altered carbohydrate attached to the Fc region thereof. See also US 2005/0123546 (Umana et al.) on antigen-binding molecules with modified glycosylation.

The preferred glycosylation variant herein comprises an Fc region, wherein a carbohydrate structure attached to the Fc region lacks fucose. Such variants have improved ADCC function. Optionally, the Fc region further comprises one or more amino acid substitutions therein which further improve ADCC, for example, substitutions at positions 298, 333, and/or 334 of the Fc region (Eu numbering of residues). Examples of publications related to "defucosylated" or "fucose-deficient" antibodies include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; Okazaki et al. J. Mol. Biol. 336: 1239-1249 (2004); Yamane-Ohnuki et al. Biotech. Bioeng. 87: 614 (2004). Examples of cell lines producing defucosylated antibodies include Lec13 CHO cells deficient in protein fucosylation (Ripka et al. Arch. Biochem. Biophys. 249:533-545 (1986); US Pat Appl No US 2003/0157108A1, Presta, L; and WO 2004/056312 A1, Adams et al., especially at Example 11), and knockout cell lines, such as alpha-1,6-fucosyltransferase gene, FUT8, knockout CHO cells (Yamane-Ohnuki et al. Biotech. Bioeng. 87: 614 (2004)).

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. Conservative substitutions are shown in Table 2 under the heading of "preferred substitutions". If such substitutions result in a change in biological activity, then more substantial changes, denominated "exemplary substitutions" in Table 2, or as further described below in reference to amino acid classes, may be introduced and the products screened.

TABLE 2

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:
(1) hydrophobic: norleucine, met, ala, val, leu, ile;
(2) neutral hydrophilic: Cys, Ser, Thr, Asn, Gln;
(3) acidic: asp, glu;
(4) basic: his, lys, arg;
(5) residues that influence chain orientation: gly, pro; and
(6) aromatic: trp, tyr, phe Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g. 6-7 sites) are mutated to generate all possible amino acid substitutions at each site. The antibodies thus generated are displayed from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to introduce one or more amino acid modifications in an Fc region of the immunoglobulin polypeptides, thereby generating a Fc region variant. The Fc region variant may comprise a human Fc region sequence (e.g., a human $IgG_1$, $IgG_2$, $IgG_3$ or $IgG_4$ Fc region) comprising an amino acid modification (e.g. a substitution) at one or more amino acid positions including that of a hinge cysteine.

In accordance with this description and the teachings of the art, it is contemplated that in some embodiments, an antibody used in methods may comprise one or more alterations as compared to the wild type counterpart antibody, e.g. in the Fc region. These antibodies would nonetheless retain substantially the same characteristics required for therapeutic utility as compared to their wild type counterpart. For example, it is thought that certain alterations can be made in the Fc region that would result in altered (i.e., either improved or diminished) C1q binding and/or Complement Dependent Cytotoxicity (CDC), e.g., as described in WO99/51642. See also Duncan & Winter Nature 322:738-40 (1988); U.S. Pat. No. 5,648,260; U.S. Pat. No. 5,624,821; and WO94/29351 concerning other examples of Fc region variants. WO00/42072 (Presta) and WO 2004/056312 (Lowman) describe antibody variants with improved or diminished binding to FcRs. The content of these patent publications are specifically incorporated herein by reference. See, also, Shields et al. J. Biol. Chem. 9(2): 6591-6604 (2001). Antibodies with increased half lives and improved binding to the neonatal Fc receptor (FcRn), which is responsible for the transfer of maternal IgGs to the fetus (Guyer et al., J. Immunol. 117:587 (1976) and Kim et al., J. Immunol. 24:249 (1994)), are described in US2005/0014934A1 (Hinton et al.). These antibodies comprise an Fc reg on with one or more substitutions therein which improve binding of the Fc region to FcRn. Polypeptide variants with altered Fc region amino acid sequences and increased or decreased C1q binding capability are described in U.S. Pat. No. 6,194,551B1, WO99/51642. The contents of those patent publications are specifically, incorporated herein by reference. See, also, Idusogie et al. J. Immunol. 164: 4178-4184 (2000).

Antibody Derivatives

The antibodies can be further modified to contain additional nonproteinaceous moieties that are known in the art and readily available. Preferably, the moieties suitable for derivatization of the antibody are water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymers are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

Screening for Antibodies with Desired Properties

The antibodies can be characterized for their physical/chemical properties and biological functions by various assays known in the art. In some embodiments, antibodies are characterized for any one or more of binding to ALK-1, reduction or blocking of ALK-1 receptor activation, reduction or blocking of ALK-1 receptor downstream molecular signaling (e.g., phosphorylation of Smad1, Smad5 and/or Samd8), disruption or blocking of ALK-1 ligand binding to ALK-1 (e.g., BMP9 or BMP10), inhibition of angiogenesis, inhibition of lymphangiogenesis, treatment and/or prevention of a tumor, cell proliferative disorder or a cancer, treatment or prevention of a disorder associated with ALK-1 expression and/or activity.

The purified antibodies can be further characterized by a series of assays including, but not limited to, N-terminal sequencing, amino acid analysis, non-denaturing size exclusion high pressure liquid chromatography (HPLC), mass spectrometry, ion exchange chromatography and papain digestion.

In certain embodiments of the invention, the antibodies produced herein are analyzed for their biological activity. In some embodiments, the antibodies of the present invention are tested for their antigen binding activity. The antigen binding assays that are known in the art and can be used herein include without limitation any direct or competitive binding assays using techniques such as western blots, radioimmunoassays, ELISA (enzyme linked immunosorbent assay), "sandwich" immunoassays, immunoprecipitation assays, fluorescent immunoassays, and protein A immunoassays.

In one embodiment, the antibody is an altered antibody that possesses some but not all effector functions, which make it a desired candidate for many applications in which the half life of the antibody in vivo is important yet certain effector functions (such as complement and ADCC) are unnecessary or deleterious. In certain embodiments, the Fc activities of the produced immunoglobulin are measured to ensure that only the desired properties are maintained. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRII only, whereas monocytes express FcγRI, FcγRII and FcγRIII. FcR expression on hematopoietic cells is summarized in Table 3 on page 464 of Ravetch and Kinet, Annu. Rev. Immunol 9:457-92 (1991). An example of an in vitro assay to assess ADCC activity of a molecule of interest is described in U.S. Pat. No. 5,500,362 or 5,821,337. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. PNAS (USA) 95:652-656 (1998). C1q binding assays may also be carried out to confirm that the antibody is unable to bind C1q and hence lacks CDC activity. To assess complement activation, a CDC assay, e.g. as described in Gazzano-Santoro et al., J. Immunol. Methods 202:163 (1996), may be performed. FcRn binding and in vivo clearance/half life determinations can also be performed using methods known in the art, e.g. those described in the Examples section.

Vectors, Host Cells and Recombinant Methods

For recombinant production of an antibody, the nucleic acid encoding it is isolated and inserted into a replicable vector for further cloning (amplification of the DNA) or for expression. DNA encoding the antibody is readily isolated and sequenced using conventional procedures (e.g., by using oligonucleotide probes that are capable of binding specifically to genes encoding the heavy and light chains of the antibody). Many vectors are available. The choice of vector depends in part on the host cell to be used. Generally, preferred host cells are of either prokaryotic or eukaryotic (generally mammalian) origin. It will be appreciated that constant regions of any isotype can be used for this purpose, including IgG, IgM, IgA, IgD, and IgE constant regions, and that such constant regions can be obtained from any human or animal species.

Generating Antibodies Using Prokaryotic Host Cells:

Vector Construction

Polynucleotide sequences encoding polypeptide components of the antibody can be obtained using standard recombinant techniques. Desired polynucleotide sequences may be isolated and sequenced from antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, E. coli is typically transformed using pBR322, a plasmid derived from an E. coli species. pBR322 contains genes encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins. Examples of pBR322 derivatives used for expression of particular antibodies are described in detail in Carter et al., U.S. Pat. No. 5,648,237.

In addition, phage vectors containing replicon and control sequences that are compatible with the host microorganism can be used as transforming vectors in connection with these hosts. For example, bacteriophage such as λGEM™-11 may be utilized in making a recombinant vector which can be used to transform susceptible host cells such as *E. coli* LE392.

The expression vector may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. Inducible promoter is a promoter that initiates increased levels of transcription of the cistron under its control in response to changes in the culture condition, e.g. the presence or absence of a nutrient or a change in temperature.

A large number of promoters recognized by a variety of potential host cells are well known. The selected promoter can be operably linked to cistron DNA encoding the light or heavy chain by removing the promoter from the source DNA via restriction enzyme digestion and inserting the isolated promoter sequence into the vector. Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Promoters suitable for use with prokaryotic hosts include the PhoA promoter, the β-galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleotide sequences have been published, thereby enabling a skilled worker operably to ligate them to cistrons encoding the target light and heavy chains (Siebenlist et al. (1980) Cell 20: 269) using linkers or adaptors to supply any required restriction sites.

In one aspect of the invention, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e. cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, Ipp, or heat-stable enterotoxin II (STII) leaders, LamB, PhoE, PelB, OmpA and MBP. In one embodiment of the invention, the signal sequences used in both cistrons of the expression system are STII signal sequences or variants thereof.

In another aspect, the production of the immunoglobulins according to the invention can occur in the cytoplasm of the host cell, and therefore does not require the presence of secretion signal sequences within each cistron. In that regard, immunoglobulin light and heavy chains are expressed, folded and assembled to form functional immunoglobulins within the cytoplasm. Certain host strains (e.g., the *E. coli* trxB- strains) provide cytoplasm conditions that are favorable for disulfide bond formation, thereby permitting proper folding and assembly of expressed protein subunits. Proba and Pluckthun Gene, 159:203 (1995).

Prokaryotic host cells suitable for expressing antibodies include Archaebacteria and Eubacteria, such as Gram-negative or Gram-positive organisms. Examples of useful bacteria include *Escherichia* (e.g., *E. coli*), Bacilli (e.g., *B. subtilis*), Enterobacteria, *Pseudomonas* species (e.g., *P. aeruginosa*), *Salmonella typhimurium*, *Serratia marcescans*, *Klebsiella*, *Proteus*, *Shigella*, *Rhizobia*, *Vitreoscilla*, or *Paracoccus*. In one embodiment, gram-negative cells are used. In one embodiment, *E. coli* cells are used as hosts for the invention. Examples of *E. coli* strains include strain W3110 (Bachmann, *Cellular and Molecular Biology*, vol. 2 (Washington, D.C.: American Society for Microbiology, 1987), pp. 1190-1219; ATCC Deposit No. 27,325) and derivatives thereof, including strain 33D3 having genotype W3110 ΔfhuA (ΔtonA) ptr3 lac Iq lacL8 ΔompTΔ(nmpc-fepE) degP41 kanR (U.S. Pat. No. 5,639,635). Other strains and derivatives thereof, such as *E. coli* 294 (ATCC 31,446), *E. coli* B, *E. coli*λ 1776 (ATCC 31,537) and *E. coli* RV308(ATCC 31,608) are also suitable. These examples are illustrative rather than limiting. Methods for constructing derivatives of any of the above-mentioned bacteria having defined genotypes are known in the art and described in, for example, Bass et al., Proteins, 8:309-314 (1990). It is generally necessary to select the appropriate bacteria taking into consideration replicability of the replicon in the cells of a bacterium. For example, *E. coli*, *Serratia*, or *Salmonella* species cane be suitably used as the host when well known plasmids such as pBR322, pBR325, pACYC 177, or pKN410 are used to supply the replicon. Typically the host cell should secrete minimal amounts of proteolytic enzymes, and additional protease inhibitors may desirably be incorporated in the cell culture.

Antibody Production

Host cells are transformed with the above-described expression vectors and cultured in conventional nutrient media modified as appropriate for inducing promoters, selecting transformants, or amplifying the genes encoding the desired sequences.

Transformation means introducing DNA into the prokaryotic host so that the DNA is replicable, either as an extrachromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the polypeptides are grown in media known in the art and suitable for culture of the selected host cells. Examples of suitable media include luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol.

The prokaryotic host cells are cultured at suitable temperatures. For *E. coli* growth, for example, the preferred temperature ranges from about 20° C. to about 39° C., more preferably from about 25° C. to about 37° C., even more preferably at about 30° C. The pH of the medium may be any pH ranging from about 5 to about 9, depending mainly on the host organism. For *E. coli*, the pH is preferably from about 6.8 to about 7.4, and more preferably about 7.0.

If an inducible promoter is used in the expression vector, protein expression is induced under conditions suitable for the activation of the promoter. In one aspect of the invention, PhoA promoters are used for controlling transcription of the polypeptides. Accordingly, the transformed host cells are cultured in a phosphate-limiting medium for induction. Preferably, the phosphate-limiting medium is the C.R.A.P medium (see, e.g., Simmons et al., J. Immunol. Methods (2002), 263: 133-147). A variety of other inducers may be used, according to the vector construct employed, as is known in the art.

In one embodiment, the expressed polypeptides of the present invention are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

In one aspect of the invention, antibody production is conducted in large quantity by a fermentation process. Various large-scale fed-batch fermentation procedures are available for production of recombinant proteins. Large-scale fermentations have at least 1000 liters of capacity, preferably about 1,000 to 100,000 liters of capacity. These fermentors use agitator impellers to distribute oxygen and nutrients, especially glucose (the preferred carbon/energy source). Small scale fermentation refers generally to fermentation in a fermentor that is no more than approximately 100 liters in volumetric capacity, and can range from about 1 liter to about 100 liters.

In a fermentation process, induction of protein expression is typically initiated after the cells have been grown under suitable conditions to a desired density, e.g., an OD550 of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time may be used.

To improve the production yield and quality of the polypeptides, various fermentation conditions can be modified. For example, to improve the proper assembly and folding of the secreted antibody polypeptides, additional vectors overexpressing chaperone proteins, such as Dsb proteins (DsbA, DsbB, DsbC, DsbD and or DsbG) or FkpA (a peptidylprolyl cis,trans-isomerase with chaperone activity) can be used to co-transform the host prokaryotic cells. The chaperone proteins have been demonstrated to facilitate the proper folding and solubility of heterologous proteins produced in bacterial host cells. Chen et al. (1999) J Bio Chem 274:19601-19605; Georgiou et al., U.S. Pat. No. 6,083,715; Georgiou et al., U.S. Pat. No. 6,027,888; Bothmann and Pluckthun (2000) J. Biol. Chem. 275:17100-17105; Ramm and Pluckthun (2000) J. Biol. Chem. 275:17106-17113; Arie et al. (2001) Mol. Microbiol. 39:199-210.

To minimize proteolysis of expressed heterologous proteins (especially those that are proteolytically sensitive), certain host strains deficient for proteolytic enzymes can be used for the present invention. For example, host cell strains may be modified to effect genetic mutation(s) in the genes encoding known bacterial proteases such as Protease III, OmpT, DegP, Tsp, Protease I, Protease Mi, Protease V, Protease VI and combinations thereof. Some *E. coli* protease-deficient strains are available and described in, for example, Joly et al. (1998), supra; Georgiou et al., U.S. Pat. No. 5,264,365; Georgiou et al., U.S. Pat. No. 5,508,192; Hara et al., Microbial Drug Resistance, 2:63-72 (1996).

In one embodiment, *E. coli* strains deficient for proteolytic enzymes and transformed with plasmids overexpressing one or more chaperone proteins are used as host cells in the expression system.

Antibody Purification

Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

In one aspect, Protein A immobilized on a solid phase is used for immunoaffinity purification of the full length antibody products. Protein A is a 41 kD cell wall protein from *Staphylococcus aureas* which binds with a high affinity to the Fc region of antibodies. Lindmark et al (1983) J. Immunol. Meth. 62:1-13. The solid phase to which Protein A is immobilized is preferably a column comprising a glass or silica surface, more preferably a controlled pore glass column or a silicic acid column. In some applications, the column has been coated with a reagent, such as glycerol, in an attempt to prevent nonspecific adherence of contaminants.

As the first step of purification, the preparation derived from the cell culture as described above is applied onto the Protein A immobilized solid phase to allow specific binding of the antibody of interest to Protein A. The solid phase is then washed to remove contaminants non-specifically bound to the solid phase. Finally the antibody of interest is recovered from the solid phase by elution.

Generating Antibodies Using Eukaryotic Host Cells:

The vector components generally include, but are not limited to, one or more of the following: a signal sequence, an origin of replication, one or more marker genes, an enhancer element, a promoter, and a transcription termination sequence.

Signal Sequence Component

A vector for use in a eukaryotic host cell may also contain a signal sequence or other polypeptide having a specific cleavage site at the N-terminus of the mature protein or polypeptide of interest. The heterologous signal sequence selected preferably is one that is recognized and processed (i.e., cleaved by a signal peptidase) by the host cell. In mammalian cell expression, mammalian signal sequences as well as viral secretory leaders, for example, the herpes simplex gD signal, are available.

The DNA for such precursor region is ligated in reading frame to DNA encoding the antibody.

Origin of Replication

Generally, an origin of replication component is not needed for mammalian expression vectors. For example, the SV40 origin may typically be used only because it contains the early promoter.

Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, where relevant, or (c) supply critical nutrients not available from complex media.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the antibody nucleic acid, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity (e.g., ATCC CRL-9096).

Alternatively, host cells (particularly wild-type hosts that contain endogenous DHFR) transformed or co-transformed with DNA sequences encoding an antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

Promoter Component

Expression and cloning vectors usually contain a promoter that is recognized by the host organism and is operably linked to the antibody polypeptide nucleic acid. Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Antibody polypeptide transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. Alternatively, the Rous Sarcoma Virus long terminal repeat can be used as the promoter.

Enhancer Element Component

Transcription of DNA encoding the antibody polypeptide of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer may be spliced into the vector at a position 5' or 3' to the antibody polypeptide-encoding sequence, but is preferably located at a site 5' from the promoter.

Transcription Termination Component

Expression vectors used in eukaryotic host cells will typically also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding an antibody. One useful transcription termination component is the bovine growth hormone polyadenylation region. See WO94/11026 and the expression vector disclosed therein.

Selection and Transformation of Host Cells

Suitable host cells for cloning or expressing the DNA in the vectors herein include higher eukaryote cells described herein, including vertebrate host cells. Propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., Annals N.Y. Acad. Sci. 383:44-68 (1982)); MRC 5 cells; FS4 cells; and a human hepatoma line (Hep G2).

Host cells are transformed with the above-described expression or cloning vectors for antibody production and cultured in conventional nutrient media modified as appropriate for inducing promoters, selecting transformants, or amplifying the genes encoding the desired sequences.

Culturing the Host Cells

The host cells used to produce an antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Purification of Antibody

When using recombinant techniques, the antibody can be produced intracellularly, or directly secreted into the medium. If the antibody is produced intracellularly, as a first step, the particulate debris, either host cells or lysed fragments, are removed, for example, by centrifugation or ultrafiltration. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human $\gamma 1$, $\gamma 2$, or $\gamma 4$ heavy chains (Lindmark et al., J. Immunol. Meth. 62:1-13 (1983)). Protein G is recommended for all mouse isotypes and for human $\gamma 3$ (Guss et al., EMBO J. 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

Immunoconjugates

The invention contemplates immunoconjugates (interchangeably termed "antibody-drug conjugates" or "ADC"), comprising an anti-ALK-1 antibody conjugated to a cytotoxic agent such as a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate).

The use of antibody-drug conjugates for the local delivery of cytotoxic or cytostatic agents, i.e. drugs to kill or inhibit tumor cells in the treatment of cancer (Syrigos and Epenetos (1999) Anticancer Research 19:605-614; Niculescu-Duvaz and Springer (1997) Adv. Drg Del. Rev. 26:151-172; U.S. Pat. No. 4,975,278) allows targeted delivery of the drug moiety to tumors, and intracellular accumulation therein, where systemic administration of these unconjugated drug agents may result in unacceptable levels of toxicity to normal cells as well as the tumor cells sought to be eliminated (Baldwin et al., (1986) Lancet pp. (Mar. 15, 1986):603-05; Thorpe, (1985) "Antibody Carriers of Cytotoxic Agents In Cancer Therapy: A Review," in Monoclonal Antibodies '84: Biological And Clinical Applications, A. Pinchera et al. (ed.s), pp. 475-506). Maximal efficacy with minimal toxicity is sought thereby. Both polyclonal antibodies and monoclonal antibodies have been reported as useful in these strategies (Rowland et al., (1986) Cancer Immunol. Immunother., 21:183-87). Drugs used in these methods include datmomycin, doxorubicin, methotrexate, and vindesine (Rowland et al., (1986) supra). Toxins used in antibody-toxin conjugates include bacterial toxins such as diphtheria toxin, plant toxins such as ricin, small molecule toxins such as geldanamycin (Mandler et al (2000) Jour. of the Nat. Cancer Inst. 92(19):1573-1581; Mandler et al (2000) Bioorganic & Med. Chem. Letters 10:1025-1028; Mandler et al (2002) Bioconjugate Chem. 13:786-791), maytansinoids (EP 1391213; Liu et al., (1996) Proc. Natl. Acad. Sci. USA 93:8618-8623), and calicheamicin (Lode et al (1998) Cancer Res. 58:2928; Hinman et al (1993) Cancer Res. 53:3336-3342). The toxins may affect their cytotoxic and cytostatic effects by mechanisms including tubulin binding, DNA binding, or topoisomerase inhibition. Some cytotoxic drugs tend to be inactive or less active when conjugated to large antibodies or protein receptor ligands.

ZEVALIN® (ibritumomab tiuxetan, Biogen/Idec) is an antibody-radioisotope conjugate composed of a murine IgG1 kappa monoclonal antibody directed against the CD20 antigen found on the surface of normal and malignant B lymphocytes and 111In or $^{90}$Y radioisotope bound by a thiourea linker-chelator (Wiseman et al (2000) Eur. Jour. Nucl. Med. 27(7):766-77; Wiseman et al (2002) Blood 99(12):4336-42; Witzig et al (2002) J. Clin. Oncol. 20(10):2453-63; Witzig et al (2002) J. Clin. Oncol. 20(15):3262-69). Although ZEVALIN has activity against B-cell non-Hodgkin's Lymphoma (NHL), administration results in severe and prolonged cytopenias in most patients. MYLOTARG™ (gemtuzumab ozogamicin, Wyeth Pharmaceuticals), an antibody drug conjugate composed of a huCD33 antibody linked to calicheamicin, was approved in 2000 for the treatment of acute myeloid leukemia by injection (Drugs of the Future (2000) 25(7):686; U.S. Pat. Nos. 4,970,198; 5,079,233; 5,585,089; 5,606,040; 5,693,762; 5,739,116; 5,767,285; 5,773,001). Cantuzumab mertansine (Immunogen, Inc.), an antibody drug conjugate composed of the huC242 antibody linked via the disulfide linker SPP to the maytansinoid drug moiety, DM1, is advancing into Phase II trials for the treatment of cancers that express CanAg, such as colon, pancreatic, gastric, and others. MLN-2704 (Millennium Pharm., BZL Biologics, Immunogen Inc.), an antibody drug conjugate composed of the anti-prostate specific membrane antigen (PSMA) monoclonal antibody linked to the maytansinoid drug moiety, DM1, is under development for the potential treatment of prostate tumors. The auristatin peptides, auristatin E (AE) and monomethylauristatin (MMAE), synthetic analogs of dolastatin, were conjugated to chimeric monoclonal antibodies cBR96 (specific to Lewis Y on carcinomas) and cAC10 (specific to CD30 on hematological malignancies) (Doronina et al (2003) Nature Biotechnology 21(7):778-784) and are under therapeutic development.

Chemotherapeutic agents useful in the generation of immunoconjugates are described herein (e.g., see above). Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes. See, e.g., WO 93/21232 published Oct. 28, 1993. A variety of radionuclides are available for the production of radioconjugated antibodies. Examples include $^{212}$Bi, $^{131}$I, $^{131}$In, $^{90}$Y, and $^{186}$Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science, 238: 1098 (1987), Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

Conjugates of an antibody and one or more small molecule toxins, such as a calicheamicin, maytansinoids, dolastatins, aurostatins, a trichothecene, and CC1065, and the derivatives of these toxins that have toxin activity, are also contemplated herein.

Maytansine and Maytansinoids

In some embodiments, the immunoconjugate comprises an antibody (full length or fragments) conjugated to one or more maytansinoid molecules.

Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

Maytansinoid drug moieties are attractive drug moieties in antibody drug conjugates because they are: (i) relatively accessible to prepare by fermentation or chemical modification, derivatization of fermentation products, (ii) amenable to derivatization with functional groups suitable for conjugation through the non-disulfide linkers to antibodies, (iii) stable in plasma, and (iv) effective against a variety of tumor cell lines.

Immunoconjugates containing maytansinoids, methods of making same, and their therapeutic use are disclosed, for example, in U.S. Pat. Nos. 5,208,020, 5,416,064 and European Patent EP 0 425 235 B1, the disclosures of which are hereby expressly incorporated by reference. Liu et al., Proc. Natl. Acad. Sci. USA 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al., Cancer Research 52:127-131 (1992) describe immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansinoid conjugate was tested in vitro on the human breast cancer cell line SK–BR-3, which expresses 3×105 HER-2 surface antigens per cell. The drug conjugate achieved a degree of cytotoxicity similar to the free maytansinoid drug, which could be increased by increasing the number of maytansinoid molecules per antibody molecule. The A7-maytansinoid conjugate showed low systemic cytotoxicity in mice.

Antibody-maytansinoid conjugates are prepared by chemically linking an antibody to a maytansinoid molecule without significantly diminishing the biological activity of either the antibody or the maytansinoid molecule. See, e.g., U.S. Pat. No. 5,208,020 (the disclosure of which is hereby expressly incorporated by reference). An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B1, Chari et al., Cancer Research 52:127-131 (1992), and U.S. patent application Ser. No. 10/960,602, filed Oct. 8, 2004, the disclosures of which are hereby expressly incorporated by reference. Antibody-maytansinoid conjugates comprising the linker component SMCC may be prepared as disclosed in U.S. patent application Ser. No. 10/960,602, filed Oct. 8, 2004. The linking groups include disulfide groups, thioether groups, acid labile groups, photolabile groups, peptidase labile groups, or esterase labile groups, as disclosed in the above-identified patents, disulfide and thioether groups being preferred. Additional linking groups are described and exemplified herein.

Conjugates of the antibody and maytansinoid may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particularly preferred coupling agents include N-succinimidyl- 3-(2-pyridyldithio) propionate (SPDP) (Carlsson et al., Biochem. J. 173:723-737 (1978)) and N-succinimidyl-4-(2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. In a preferred embodiment, the linkage is formed at the C-3 position of maytansinol or a maytansinol analogue.

Auristatins and Dolastatins

In some embodiments, the immunoconjugate comprises an antibody conjugated to dolastatins or dolostatin peptidic analogs and derivatives, the auristatins (U.S. Pat. Nos. 5,635,483; 5,780,588). Dolastatins and auristatins have been shown to interfere with microtubule dynamics, GTP hydrolysis, and nuclear and cellular division (Woyke et al (2001) Antimicrob. Agents and Chemother. 45(12):3580-3584) and have anticancer (U.S. Pat. No. 5,663,149) and antifungal activity (Pettit et al (1998) Antimicrob. Agents Chemother. 42:2961-2965). The dolastatin or auristatin drug moiety may be attached to the antibody through the N (amino) terminus or the C (carboxyl) terminus of the peptidic drug moiety (WO 02/088172).

Exemplary auristatin embodiments include the N-terminus linked monomethylauristatin drug moieties DE and DF, disclosed in "Monomethylvaline Compounds Capable of Conjugation to Ligands", U.S. Ser. No. 10/983,340, filed Nov. 5, 2004, the disclosure of which is expressly incorporated by reference in its entirety.

Typically, peptide-based drug moieties can be prepared by forming a peptide bond between two or more amino acids and/or peptide fragments. Such peptide bonds can be prepared, for example, according to the liquid phase synthesis method (see E. Schröder and K. Lüibke, "The Peptides", volume 1, pp 76-136, 1965, Academic Press) that is well known in the field of peptide chemistry. The auristatin/dolastatin drug moieties may be prepared according to the methods of: U.S. Pat. No. 5,635,483; U.S. Pat. No. 5,780,588; Pettit et al (1989) J. Am. Chem. Soc. 111:5463-5465; Pettit et al (1998) Anti-Cancer Drug Design 13:243-277; Pettit, G. R., et al. Synthesis, 1996, 719-725; and Pettit et al (1996) J. Chem. Soc. Perkin Trans. 1 5:859-863. See also Doronina (2003) Nat Biotechnol 21(7):778-784; "Monomethylvaline Compounds Capable of Conjugation to Ligands", U.S. Ser. No. 10/983,340, filed Nov. 5, 2004, hereby incorporated by reference in its entirety (disclosing, e.g., linkers and methods of preparing monomethylvaline compounds such as MMAE and MMAF conjugated to linkers).

Calicheamicin

In other embodiments, the immunoconjugate comprises an antibody conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, γ1I, α2I, α3I, N-acetyl-γ1I, PSAG and θI1 (Hinman et al., Cancer Research 53:3336-3342 (1993), Lode et al., Cancer Research 58:2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

Other Cytotoxic Agents

Other antitumor agents that can be conjugated to the antibodies include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radioconjugated antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $tc^{99}m$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al (1978) Biochem. Biophys. Res. Commun. 80: 49-57) can be used to incorporate iodine-123. "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as his (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., Cancer Research 52:127-131 (1992); U.S. Pat. No. 5,208,020) may be used.

The compounds expressly contemplate, but are not limited to, ADC prepared with cross-linker reagents: BMPS, EMCS, GMBS, HBVS, LC-SMCC, MBS, MPBH, SBAP, SIA, STAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A). See pages 467-498, 2003-2004 Applications Handbook and Catalog.

Preparation of Antibody Drug Conjugates

In the antibody drug conjugates (ADC), an antibody (Ab) is conjugated to one or more drug moieties (D), e.g. about 1 to about 20 drug moieties per antibody, through a linker (L). The ADC of Formula I may be prepared by several routes, employing organic chemistry reactions, conditions, and reagents known to those skilled in the art, including: (1) reaction of a nucleophilic group of an antibody with a bivalent linker reagent, to form Ab-L, via a covalent bond, followed by reaction with a drug moiety D; and (2) reaction of a nucleophilic group of a drug moiety with a bivalent linker reagent, to form D-L, via a covalent bond, followed by reaction with the nucleophilic group of an antibody. Additional methods for preparing ADC are described herein.

$$Ab\text{-}(L\text{-}D)_p \qquad I$$

The linker may be composed of one or more linker components. Exemplary linker components include 6-maleimidocaproyl ("MC"), maleimidopropanoyl ("MP"), valine-citrulline ("val-cit"), alanine-phenylalanine ("ala-phe"), p-aminobenzyloxycarbonyl ("PAB"), N-Succinimidyl 4-(2-pyridylthio) pentanoate ("SPP"), N-Succinimidyl 4-(N-maleimidomethyl)cyclohexane-1 carboxylate ("SMCC"), and N-Succinimidyl (4-iodo-acetyl) aminobenzoate ("SIAB"). Additional linker components are known in the art and some are described herein. See also "Monomethylvaline Compounds Capable of Conjugation to Ligands", U.S. Ser. No. 10/983,340, filed Nov. 5, 2004, the contents of which are hereby incorporated by reference in its entirety.

In some embodiments, the linker may comprise amino acid residues. Exemplary amino acid linker components include a dipeptide, a tripeptide, a tetrapeptide or a pentapeptide. Exemplary dipeptides include: valine-citrulline (vc or val-cit), alanine-phenylalanine (af or ala-phe). Exemplary tripeptides include: glycine-valine-citrulline (gly-val-cit) and glycine-glycine-glycine (gly-gly-gly). Amino acid residues which comprise an amino acid linker component include those occurring naturally, as well as minor amino acids and non-naturally occurring amino acid analogs, such as citrulline. Amino acid linker components can be designed and optimized in their selectivity for enzymatic cleavage by a particular enzymes, for example, a tumor-associated protease, cathepsin B, C and D, or a plasmin protease.

Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by introducing one, two, three, four, or more cysteine residues (e.g., preparing mutant antibodies comprising one or more non-native cysteine amino acid residues).

Antibody drug conjugates may also be produced by modification of the antibody to introduce electrophilic moieties, which can react with nucleophilic substituents on the linker reagent or drug. The sugars of glycosylated antibodies may be oxidized, e.g. with periodate oxidizing reagents, to form aldehyde or ketone groups which may react with the amine group of linker reagents or drug moieties. The resulting imine Schiff base groups may form a stable linkage, or may be reduced, e.g. by borohydride reagents to form stable amine linkages. In one embodiment, reaction of the carbohydrate portion of a glycosylated antibody with either glactose oxidase or sodium meta-periodate may yield carbonyl (aldehyde and ketone) groups in the protein that can react with appropriate groups on the drug (Hermanson, Bioconjugate Techniques). In another embodiment, proteins containing N-terminal serine or threonine residues can react with sodium meta-periodate, resulting in production of an aldehyde in place of the first amino acid (Geoghegan & Stroh, (1992) Bioconjugate Chem. 3:138-146; U.S. Pat. No. 5,362,852). Such aldehyde can be reacted with a drug moiety or linker nucleophile.

Likewise, nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters; HOBt esters, haloformates, and acid halides; (ii) alkyl and benzyl halides such as haloacetamides; (iii) aldehydes, ketones, carboxyl, and maleimide groups.

Alternatively, a fusion protein comprising the antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

In yet another embodiment, the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

Covalent Modifications to ALK-1 Polypeptides

Covalent modifications of the polypeptide antagonists of the invention (e.g., a polypeptide antagonist fragment, an ALK-1 fusion molecule, such as an ALK-1 immunoadhesin, or an anti-ALK-1 antibody), are included within the scope of this invention. They may be made by chemical synthesis or by enzymatic or chemical cleavage of the polypeptide, if applicable. Other types of covalent modifications of the polypeptide are introduced into the molecule by reacting targeted amino acid residues of the polypeptide with an organic derivatizing agent that is capable of reacting with selected side chains or the N- or C-terminal residues, or by incorporating a modified amino acid or unnatural amino acid into the growing polypeptide chain, e.g., Ellman et al. *Meth. Enzym.* 202:301-336 (1991); Noren et al. *Science* 244:182 (1989); and, & US Patent application publications 20030108885 and 20030082575.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is typically performed in 0.1 M sodium cacodylate at pH 6.0.

Lysinyl and amino-terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate, pyridoxal phosphate, pyridoxal, chloroborohydride, trinitrobenzenesulfonic acid, O-methylisourea, 2,4-pentanedione, and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay.

Carboxyl side groups (aspartyl or glutamyl) are selectively modified by reaction with carbodiimides (R—N=C=N—R'), where R and R' are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues, respectively. These residues are deamidated under neutral or basic conditions. The deamidated form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T.E. Creighton, *Proteins: Structure and Molecular Properties*, W.H. Freeman & Co., San Francisco, pp. 79-86 (1983)), acetylation of the N-terminal amine, and amidation of any C-terminal carboxyl group.

Another type of covalent modification involves chemically or enzymatically coupling glycosides to a polypeptide of the invention. These procedures are advantageous in that they do not require production of the polypeptide in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 published 11 Sep. 1987, and in Aplin and Wriston, *CRC Crit. Rev. Biochem.*, pp. 259-306 (1981).

Removal of any carbohydrate moieties present on a polypeptide of the invention may be accomplished chemically or enzymatically. Chemical deglycosylation requires exposure of the polypeptide to the compound trifluoromethanesulfonic acid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin, et al. *Arch. Biochem. Biophys:* 259:52 (1987) and by Edge et al. *Anal. Biochem.*, 118:131 (1981). Enzymatic cleavage of carbohydrate moieties, e.g., on antibodies, can be achieved by the use of a variety of endo- and exo-glycosidases as described by Thotakura et al. *Meth. Enzymol.* 138:350 (1987).

Another type of covalent modification of a polypeptide of the invention comprises linking the polypeptide to one of a variety of nonproteinaceous polymers, e.g., polyethylene glycol, polypropylene glycol, or polyoxyalkylenes, in the manner set forth in U.S. Pat. No. 4,640,835; 4,496,689; 4,301,144; 4,670,417; 4,791,192 or 4,179,337.

Pharmaceutical Formulations

Therapeutic formulations comprising an antibody or immunoadhesin of the invention are prepared for storage by mixing the antibody having the desired degree of purity with optional physiologically acceptable carriers, excipients or stabilizers (Remington: The Science and Practice of Pharmacy 20th edition (2000)), in the form of aqueous solutions, lyophilized or other dried formulations. Acceptable carriers, excipients, or stabilizers are nontoxic to recipients at the dosages and concentrations employed, and include buffers such as phosphate, citrate, histidine and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEENT™, PLURONICS™ or polyethylene glycol (PEG).

The formulation herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington: The Science and Practice of Pharmacy 20th edition (2000).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the immunoglobulin, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate; non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated immunoglobulins remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

It is further contemplated that an agent useful in the invention can be introduced to a subject by gene therapy. Gene therapy refers to therapy performed by the administration of a nucleic acid to a subject. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs or siRNA can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., Proc. Natl. Acad. Sci. USA 83:4143-4146 (1986)). The oligonucleotides can be modified to enhance their uptake, e.g. by substituting their negatively charged phosphodiester groups by uncharged groups. For general reviews of the methods of gene therapy, see, for example, Goldspiel et al. Clinical Pharmacy 12:488-505 (1993); Wu and Wu Biotherapy 3:87-95 (1991); Tolstoshev Ann. Rev. Pharmacol. Toxicol. 32:573-596 (1993); Mulligan Science 260:926-932 (1993); Morgan and Anderson Ann. Rev. Biochem. 62:191-217 (1993); and May TIBTECH 11:155-215 (1993). Methods commonly known in the art of recombinant DNA technology which can be used are described in Ausubel et al. eds. (1993) Current Protocols in Molecular Biology, John Wiley & Sons, NY; and Kriegler (1990) Gene Transfer and Expression, A Laboratory Manual, Stockton Press, NY.

Dosage and Administration

The molecules are administered to a human patient, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes, and/or subcutaneous administration.

In certain embodiments, the treatment of the invention involves the combined administration of an ALK-1 antagonist and one or more anti-cancer agents, e.g., anti-angiogenesis agents or anti-lymphangiogenesis agents. In one embodiment, additional anti-cancer agents are present, e.g., one or more different anti-angiogenesis agents, one or more chemotherapeutic agents, etc. The invention also contemplates administration of multiple inhibitors, e.g., multiple antibodies to the same antigen or multiple antibodies to different cancer active molecules. In one embodiment, a cocktail of different chemotherapeutic agents is administered with the ALK-1 antagonist and/or one or more anti-angiogenesis agents. The combined administration includes coadministration, using separate formulations or a single pharmaceutical formulation, and/or consecutive administration in either order. For example, a ALK-1 antagonist may precede, follow, alternate with administration of the anti-cancer agents, or may be given simultaneously therewith. In one embodiment, there is a time period while both (or all) active agents simultaneously exert their biological activities.

For the prevention or treatment of disease, the appropriate dosage of ALK-1 antagonist will depend on the type of disease to be treated, as defined above, the severity and course of the disease, whether the inhibitor is administered for preventive or therapeutic purposes, previous therapy, the patient's clinical history and response to the inhibitor, and the discretion of the attending physician. The inhibitor is suitably administered to the patient at one time or over a series of treatments. In a combination therapy regimen, the compositions of the invention are administered in a therapeutically effective amount or a therapeutically synergistic amount. As used herein, a therapeutically effective amount is such that administration of a composition of the invention and/or co-administration of ALK-1 antagonist and one or more other therapeutic agents, results in reduction or inhibition of the targeting disease or condition. The effect of the administration of a combination of agents can be additive. In one embodiment, the result of the administration is a synergistic effect. A therapeutically synergistic amount is that amount of ALK-1 antagonist and one or more other therapeutic agents, e.g., an angiogenesis inhibitor, necessary to synergistically or significantly reduce or eliminate conditions or symptoms associated with a particular disease.

Depending on the type and severity of the disease, about 1 μg/kg to 50 mg/kg (e.g. 0.1-20 mg/kg) of ALK-1 antagonist or angiogenesis inhibitor is an initial candidate dosage for administration to the patient, whether, for example, by one or more separate administrations, or by continuous infusion. A typical daily dosage might range from about 1 μg/kg to about 100 mg/kg or more, depending on the factors mentioned above. For repeated administrations over several days or longer, depending on the condition, the treatment is sustained until a desired suppression of disease symptoms occurs. However, other dosage regimens may be useful. Typically, the clinician will administered a molecule(s) until a dosage(s) is reached that provides the required biological effect. The progress of the therapy of the invention is easily monitored by conventional techniques and assays.

For example, preparation and dosing schedules for angiogenesis inhibitors, e.g., anti-VEGF antibodies, such as AVASTIN® (Genentech), may be used according to manufacturers' instructions or determined empirically by the skilled practitioner. Depending on the type and severity of the disease, about 1 µg/kg to 100 mg/kg (e.g., 0.1-20 mg/kg) of VEGF-specific antagonist is an initial candidate dosage for administration to the patient, whether, for example, by one or more separate administrations, or by continuous infusion. A typical daily dosage might range from about 1 µg/kg to about 100 mg/kg or more, depending on the factors mentioned above. In some embodiments, particularly desirable dosages include, for example, 5 mg/kg, 7.5 mg/kg, 10 mg/kg, and 15 mg/kg. For repeated administrations over several days or longer, depending on the condition, the treatment is sustained until the cancer is treated, as measured by the methods described above or known in the art. However, other dosage regimens may be useful. In one example, if the VEGF-specific antagonist is an antibody, the antibody of the invention is administered once every week, every two weeks, or every three weeks, at a dose range from about 5 mg/kg to about 15 mg/kg, including but not limited to 7.5 mg/kg or 10 mg/kg. The progress of the therapy of the invention is easily monitored by conventional techniques and assays.

In one example, bevacizumab is the VEGF-specific antagonist. Bevacizumab is supplied for therapeutic uses in 100 mg and 400 mg preservative-free, single-use vials to deliver 4 ml or 16 ml of bevacizumab (25 mg/ml). The 100 mg product is formulated in 240 mg α,α-trehalose dehydrate, 23.2 mg sodium phosphate (monobasic, monohydrate), 4.8 mg sodium phosphate (dibasic, anhydrous), 1.6 mg polysorbate 20, and Water for Injection, USP. The 400 mg product is formulated in 960 mg α,α-trehalose dehydrate, 92.8 mg sodium phosphate (monobasic, monohydrate), 19.2 mg sodium phosphate (dibasic, anhydrous), 6.4 mg polysorbate 20, and Water for Injection, USP.

In another example, preparation and dosing schedules for such chemotherapeutic agents may be used according to manufacturers' instructions or as determined empirically by the skilled practitioner. Preparation and dosing schedules for chemotherapy are also described in Chemotherapy Service Ed., M.C. Perry, Williams & Wilkins, Baltimore, Md. (1992).

Efficacy of the Treatment

The efficacy of the treatment of the invention can be measured by various endpoints commonly used in evaluating neoplastic or non-neoplastic disorders. For example, cancer treatments can be evaluated by, e.g., but not limited to, tumor regression, tumor weight or size shrinkage, time to progression, duration of survival, progression free survival, overall response rate, duration of response, and quality of life. Because the anti-angiogenesis agents described herein target the tumor vasculature and not necessarily the neoplastic cells themselves, they represent a unique class of anticancer drugs, and therefore can require unique measures and definitions of clinical responses to drugs. For example, tumor shrinkage of greater than 50% in a 2-dimensional analysis is the standard cut-off for declaring a response. However, the inhibitors may cause inhibition of metastatic spread without shrinkage of the primary tumor, or may simply exert a tumouristatic effect. Accordingly, approaches to determining efficacy of the therapy can be employed, including for example, measurement of plasma or urinary markers of angiogenesis and measurement of response through radiological imaging.

The following examples are provided for illustrative purposes only and are not to be construed as limiting upon the teachings herein.

EXAMPLES

Example 1

Generation of an ALK1.Fc Molecule

Using standard molecular biology techniques, an ALK1.Fc molecule was generated by attaching the extracellular domain of ALK-1 (amino acid residues 1-118 of human ALK-1) to the Fc region of human IgG$_1$ via a polypeptide linker. Briefly, an extracellular fragment of human ALK-1 (amino acid 1-118) was subcloned into a pRK5 vector that had been engineered for the expression of fusion protein with a C-terminal Fc of human IgG1 ALK1.Fc was purified with Protein-A affinity chromatography from conditioned medium harvested from serum-free culture of CHO cells transiently transfected with the expression plasmid. The ALK1.Fc molecule had the following cDNA and amino acid sequences:

ALK1.Fc cDNA sequence:
(SEQ ID NO: 1)
ATGACCTTGGGCTCCCCCAGGAAAGGCCTTCTGATGCTGCTGATGGCCT

TGGTGACCCAGGGAGACCCTGTGAAGCCGTCTCGGGGCCCGCTGGTGAC

CTGCACGTGTGAGAGCCCACATTGCAAGGGGCCTACCTGCCGGGGGCC

TGGTGCACAGTAGTGCTGGTGCGGGAGGAGGGGAGGCACCCCCAGGAAC

ATCGGGGCTGCGGGAACTTGCACAGGGAGCTCTGCAGGGGGCGCCCCAC

CGAGTTCGTCAACCACTACTGCTGCGACAGCCACCTCTGCAACCACAAC

GTGTCCCTGGTGCTGGAGGCCACCCAACCTCCTTCGGAGCAGCCGGGAA

CAGATGGCCAGACCGGTGTCACCGACAAAGCTGCGCACTATACTCTGTG

CCCACCGTGCCCAGCACCTGAACTCCTGGGGGGACCGTCAGTCTTCCTC

TTCCCCCCAAAACCCAAGGACACCCTCATGATCTCCCGGACCCCTGAGG

TCACATGCGTGGTGGTGGCCGTGAGCCACGAAGACCCTGAGGTCAAGTT

CAACTGGTACGTGGACGGCGTGGAGGTGCATAATGCCAAGACAAAGCCG

CGGGAGGAGCAGTACAACAGCACGTACCGTGTGGTCAGCGTCCTCACCG

TCCTGCACCAGGACTGGCTGAATGGCAAGGAGTACAAGTGCAAGGTCTC

CAACAAAGCCCTCCCAGCCCCCATCGAGAAAACCATCTCCAAAGCCAAA

GGGCAGCCCCGAGAACCACAGGTGTACACCCTGCCCCCATCCCGGGAAG

AGATGACCAAGAACCAGGTCAGCCTGACCTGCCTGGTCAAAGGCTTCTA

TCCCAGCGACATCGCCGTGGAGTGGGAGAGCAATGGGCAGCCGGAGAAC

AACTACAAGACCACGCCTCCCGTGCTGGACTCCGACGGCTCCTTCTTCC

TCTACAGCAAGCTCACCGTGGACAAGAGCAGGTGGCAGCAGGGGAACGT

CTTCTCATGCTCCGTGATGCATGAGGCTCTGCACAACCACTACACGCAG

AAGAGCCTCTCCCTGTCTCCGGGTAAATGA

ALK1.Fc protein sequence:
(SEQ ID NO: 2)
MTLGSPRKGLLMLLMALVTQGDPVKPSRGPLVTCTCESPHCKGPTCRGA

WCTVVLVREEGRHPQEHRGCGNLHRELCRGRPTEFVNHYCCDSHLCNHN

-continued

VSLVLEATQPPSEQPGTDGQTGVTDKAAHYTLCPPCPAPELLGGPSVFL

FPPKPKDTLMISRTPEVTCVVVAVSHEDPEVKFNWYVDGVEVHNAKTKP

REEQYNSTYRVVSVLTVLHQDWLNGKEYKCKVSNKALPAPIEKTISKAK

GQPREPQVYTLPPSREEMTKNQVSLTCLVKGFYPSDIAVEWESNGQPEN

NYKTTPPVLDSDGSFFLYSKLTVDKSRWQQGNVFSCSVMHEALHNHYTQ

KSLSLSPGK

Example 2

Treatment with ALK1.Fc Enhances Endothelial Cell Sprouting In Vitro

The effect of inhibiting ALK-1 signalling on endothelial cell growth was explored using the HUVEC fibrin gel bead assay. Details of the HUVEC fibrin gel bead assay have been previously described (Nakatsu, M N, Microvascular Research 44:102-112 (2003)). Briefly, Cytodex 3 beads (Amersham Pharmacia Biotech) were coated with 350-400 human umbilical vein endothelia cells (HUVECs) per bead in 2 ml EGM-2 medium (Clonetics). About 200 HUVECs-coated beads were imbedded in fibrin clot in one well of 12-well tissue culture plate. $80 \times 10^3$ D551 human fibroblast cells were plated on top of the clot and medium was changed every 2 days. ALK1.Fc was added to the culture medium at 5 ug/ml. Phase-contrast microscopy images were taken on day 9.

HUVECs growing in fibrin gels in the presence of co-cultured human fibroblast cells generate sprouts with a distinct lumen-like structure (Nakatsu, M. N. et al. Microvasc Res 66, 102-12 (2003)). Addition of ALK1.Fc greatly increased the length of the sprouts (FIG. 1), suggesting that blocking ALK-1 signaling allowed the endothelial cells to adapt a more exploratory behavior. These results indicated that ALK1.Fc was able to affect endothelial cells by sequestering ALK-1 ligand and preventing the activation of endogenous ALK-1.

Example 3

Treatment with ALK1-Fc Affects Retinal Vascular Development In Vivo

Neonatal SD rats from the same litters were used to study the effect of ALK1.Fc on retinal vascular development. Rats were injected i.p. with ALK1.Fc (10 mg/kg body weight) on postnatal day 4 (P4), P6 and P9. On P11, rats were anesthetized with Isoflurane. FITC-labeled *Lycopersicon Esculentum* Lectin (150 µg in 150 µl of 0.9% NaCl; Vector Laboratories) was injected intracardially and allowed to circulate for 3 min. Eyes were collected and fixed with 4% PFA in PBS overnight, followed by PBS washes. The dissected retinas were blocked with 10% goat serum in PBST (PBS, 0.5% Triton X-100) for 3 hrs, then incubated overnight with biotinylated isolectin B4 (1:100, *Bandeiraea simplicifolia*; Molecular Probe) or Cy3-conjugated anti-alpha smooth muscle actin (ASMA, 1:200, Sigma-Aldrich), with 10% goat serum in PBST. To visualize the biotinylated isolectin B4, retinas were then washed 4 times in PBST, and incubated overnight with Cy3-streptavidin (1:200, Sigma-Aldrich). After staining was completed, retinas were washed 4 times in PBST. All overnight incubations were done at 4° C. Images of flat mounted retinas were captured by confocal fluorescence microscopy.

Early postnatal rat retina develops a stereotypic vascular pattern in a well-defined sequence of events. The superficial retinal vasculature develops as an expanding network from the optic nerve head, with active sprouting at the periphery and extensive remodeling at the center. Different aspects of vessel development, e.g. vessel sprouting, remodeling, maturation and arterial-venous specification can be readily followed. In ALK1.Fc treated retinas, the characteristic pattern of radially alternating arteries and veins was mostly unaffected. There was, however, a clear increase of the vascular density, especially the microvessels near the veins (Isolectin-Cy3; FIG. 2). In addition there was a dramatic reduction of blood perfusion in the microvessels and veins (Lectin-FITC; FIGS. 3 & 4). Interestingly, the retinal arteries were apparently enlarged, which was reminiscent of the vascular defect observed in Alk1 deficient embryos. Furthermore, the enlarged retinal arteries have disorganized vascular smoother muscle cell coverage (ASMA; FIGS. 3 & 4). These results indicate that ALK1.Fc treatment wag able to affect vascular development in neonatal rat retina by interfering with ALK-1 signaling in vivo.

Example 4

Treatment with ALK1-Fc Inhibits Tumor Growth In Vivo

To explore whether ALK-1 signaling is directly involved in tumor growth, we tested the effect of ALK1.Fc on tumor angiogenesis and tumor growth in nude mice bearing subcutaneous human tumor xenografts. Beige nude mice (Charles River Laboratories, Hollister, Calif.) were maintained in accordance with the guide for the care and use of laboratory animals. Six- to eight-week-old female mice were used in each study. To obtain subcutaneous tumors, mice were injected with 0.1 ml tumor cell suspension containing 50% matrigel (BD Bioscience) into the right posterior flank. $5 \times 10^6$ human colon cancer HM7 cells, $10 \times 10^6$ human lung carcinoma MV-522 cells, $1 \times 10^6$ rat glioblastoma C6 cells or $10 \times 10^6$ human lung carcinoma Calu6 cells were injected into each mouse. ALK1.Fc (10 mg/kg) was administered via i.p., as follows: for HM7 ALK1.Fc treatment (q/2d) was initiated 3 days after tumor inoculation, for MV-522 ALK1.Fc treatment (q/2d) was initiated 16 days after tumor inoculation, for C6 ALK1.Fc treatment (2×/w) was initiated 3 days after tumor inoculation, for Calu6 ALK1.Fc treatment (q/2d) was initated 22 days after tumor inoculation. Tumor growth was quantitated by caliper measurements. Tumor volume ($mm^3$) was determined by measuring the length (l) and width (w) and calculating the volume ($V=lw^2/2$). 10 to 15 animals were included in each group.

Figure 5B:
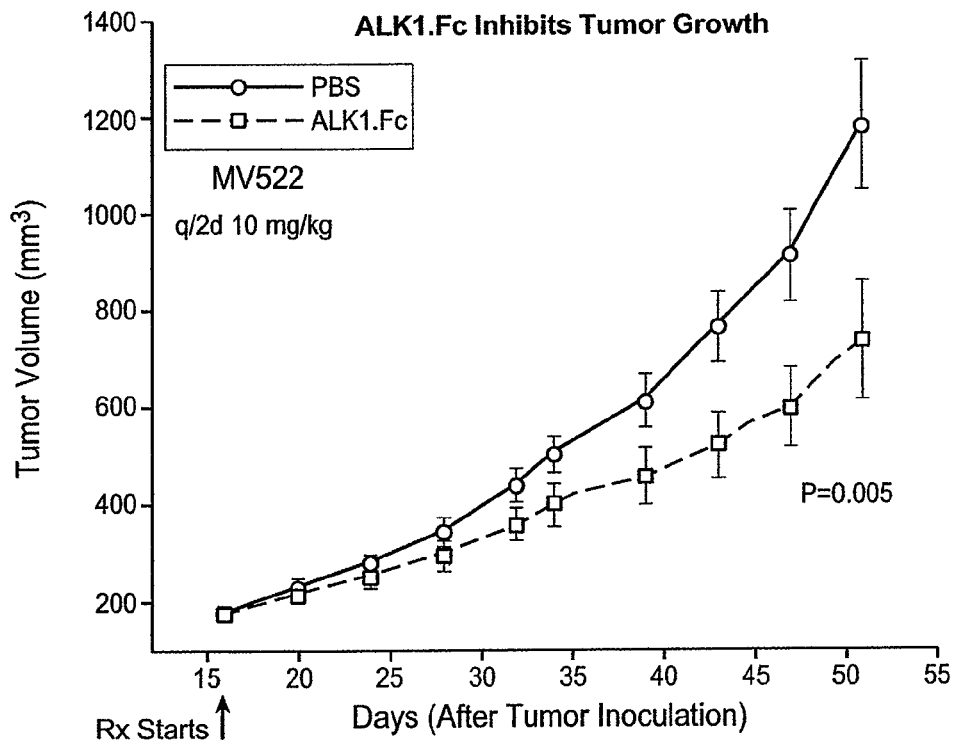
Figure 6A:
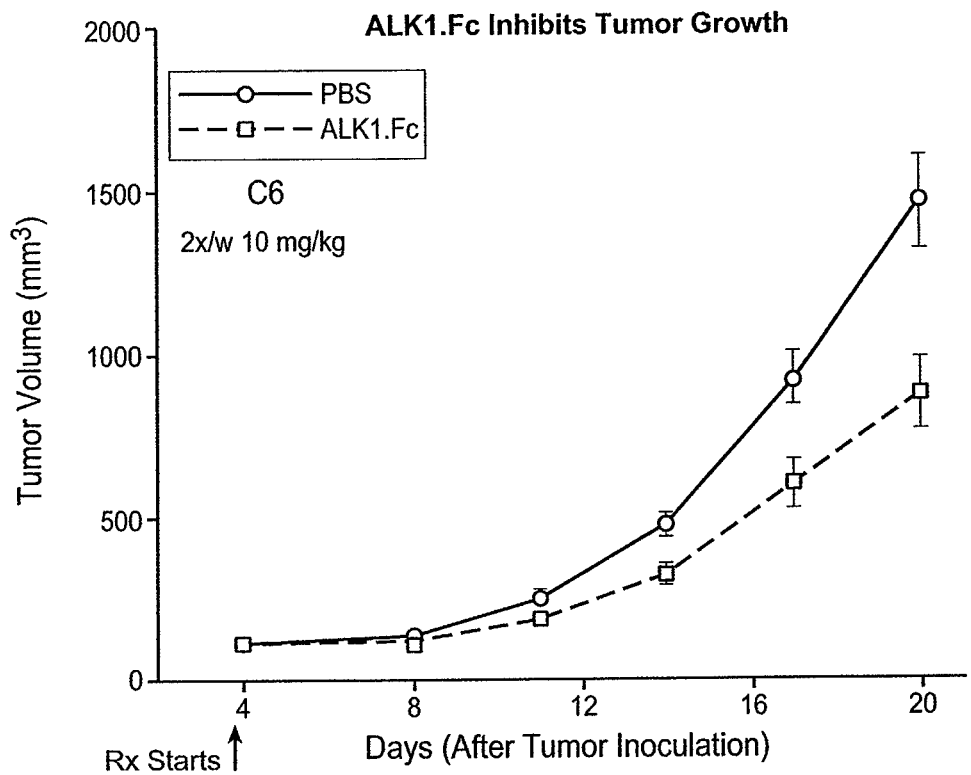
FIGS. 6A-6B are graphs showing that ALK1.Fc (10 mg/kg) inhibits tumor growth in C6 (FIG. 6A) and Calu6 (FIG. 6B) xenografts. Mean tumor volumes with SEs are presented.
Figure 6B:
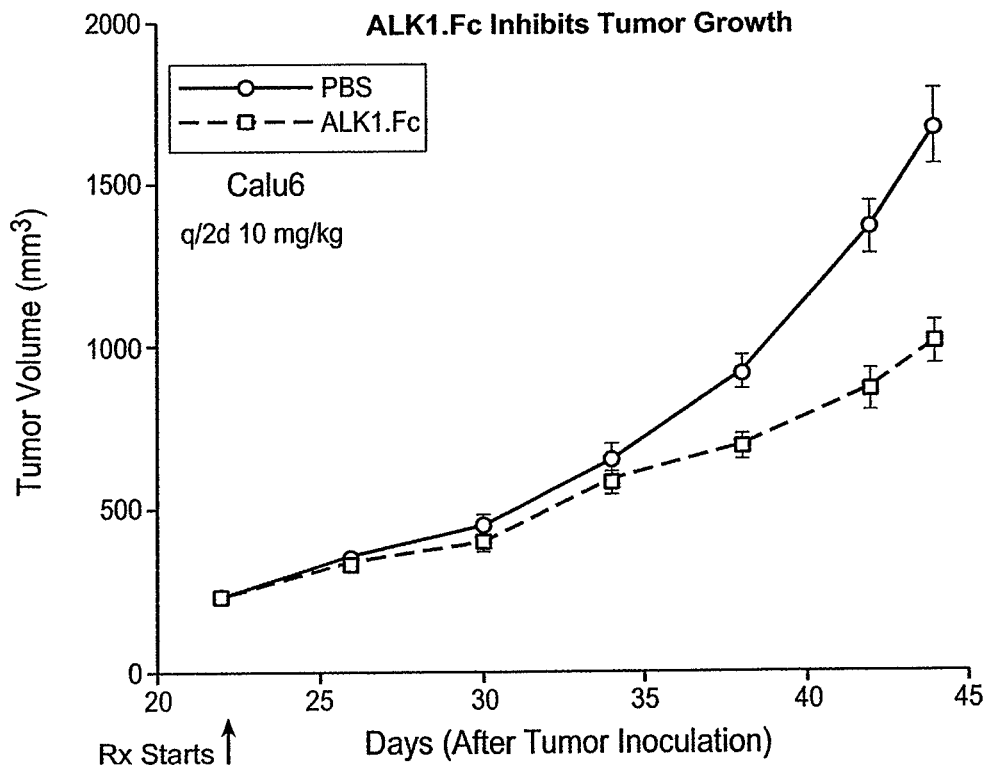

ALK1.Fc treatment significantly inhibited tumor growth as compared to vehicle treatment (FIGS. 5 & 6). The effect on tumor growth was observed in all the xenograft tumor models tested indicating that the observed anti-tumor effects were not tumor type specific.

Example 5

Combination of ALK1-Fc and Anti-VEGF

Figure 7:
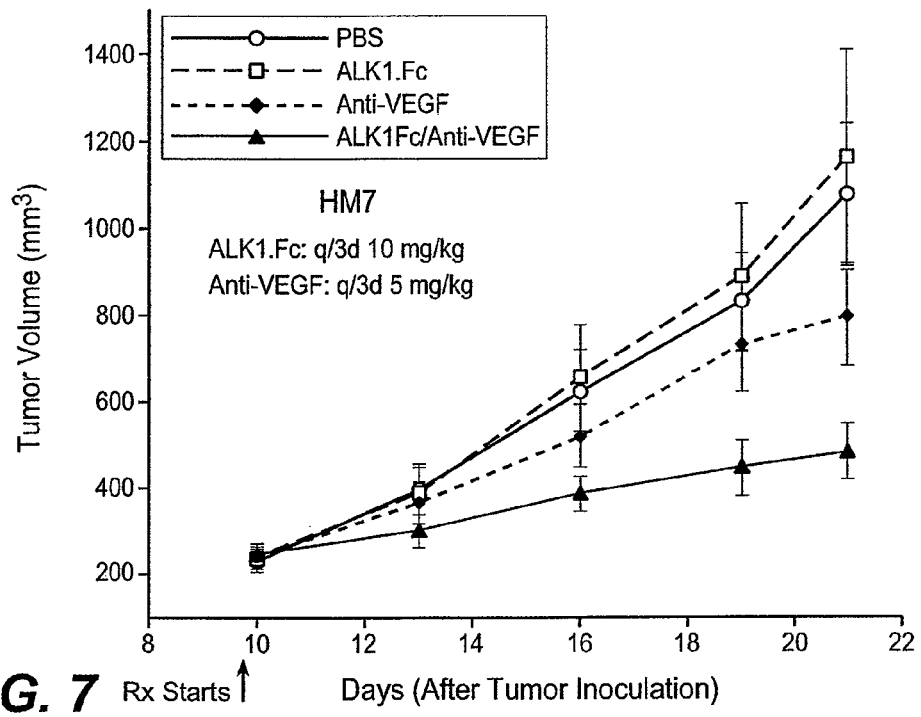
FIG. 7 is a graph showing that ALK1.Fc has additive anti-tumor activity when combined with anti-VEGF in HM7 xenografts.
Figure 8:
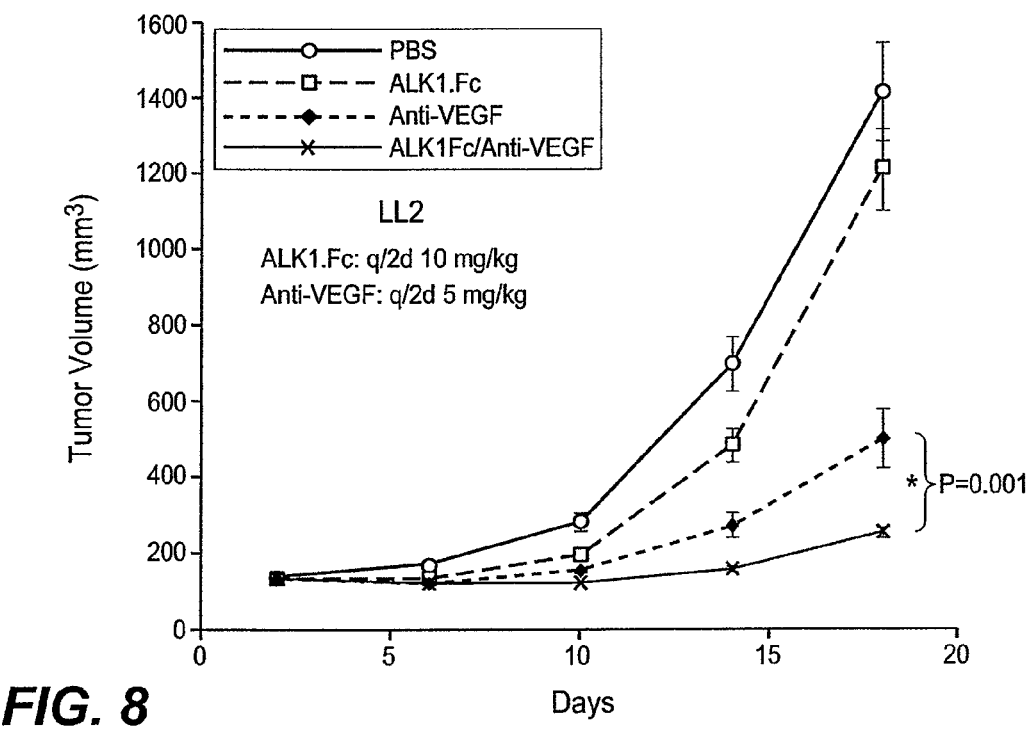
FIG. 8 is a graph showing that ALK1.Fc has additive anti-tumor activity when combined with anti-VEGF in LL2 xenografts.
Figure 9A:
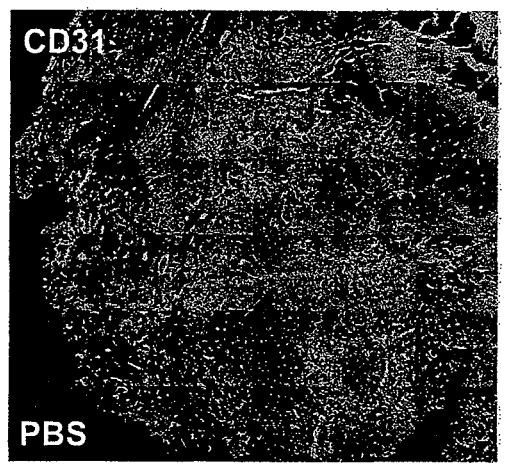
FIGS. 9A-9D are confocal images showing tumor vascular density in LL2 tumor model mice treated with PBS (FIG. 9A), ALK1.Fc (FIG. 9B), Anti-VEGF antibody (B20-4.1, 5 mg/kg) (FIG. 9C) or anti-VEGF antibody and ALK1.Fc (FIG. 9D).
Figure 9B:
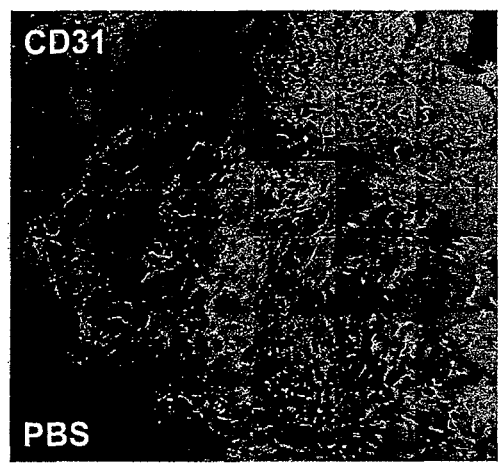
Figure 9C:
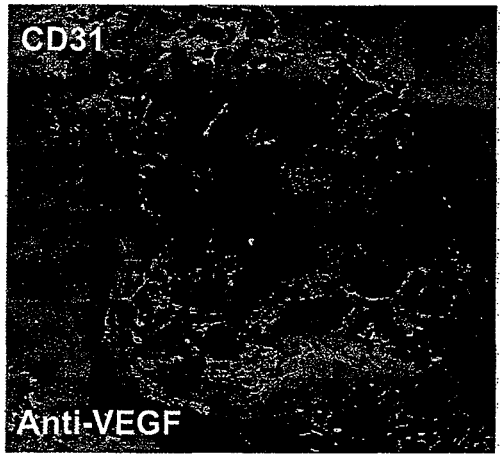
Figure 9D:
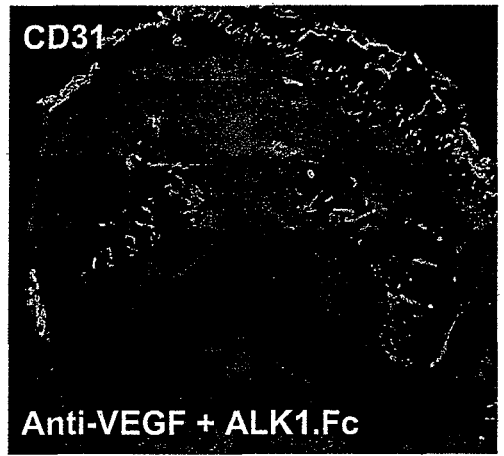

In the HM7 tumor study described above in Example 4, ALK1.Fc treatment began three day after the tumor cells were injected. The tumor growth inhibition activity of ALK1.Fc was reduced when treatment (10 mg/kg at q/3d) was initiated nine days after tumor cell inoculation (FIG. 7). In this model treatment with anti-VEGF antibody (B20-4.1, 5 mg/kg at q/3d) was also less effective when treatment was delayed. However, significant additive effect was observed when both agents were used in combination (FIG. 7). The combined effect of anti-VEGF antibody and ALK1.Fc was also studied in the LL2 xenograft model. 5×10⁶ mouse lewis lung carcinoma LL2 cells were injected into each mouse and treatment with ALK1.Fc (10 mg/kg at q/2d) and anti-VEGF antibody (5 mg/kg at q/2d) was initiated 2 days after tumor inoculation. The results show that combination therapy in the LL2 tumor model resulted in much greater anti-tumor efficacy in comparison to mono-therapy (FIG. 8).

The effect of anti-VEGF antibody and ALK1.Fc on tumor vascular density, as assessed by CD31 staining, was examined in the LL2 tumor model. On day 18 after tumor cell inoculation, tumors were removed and fixed by immersion in 1% paraformaldehyde (PFA) in PBS for 2 hr, followed by incubation in 30% sucrose overnight for cryoprotection. Samples were embedded in OCT and sections of 40 µm thickness were prepared and stained with anti-mouse CD31 (1:50, BD Pharmingen), followed by FITC-conjugated goated anti-rat IgG. As expected, treatment with anti-VEGF antibody alone significantly reduced vascular density in treated tumors. Treatment with ALK1.Fc, however, had a marginal effect on tumor vascular density. Strikingly, treatment with both agents resulted in an even more dramatic reduction of tumor vessel density (FIG. 9), consistent with the additive anti-tumor effect. Together, these results demonstrated that blocking of Alk1 signaling with ALK1.Fc could have broad anti-tumor efficacy, especially when combined with anti-VEGF.

Example 6

Treatment with ALK1-Fc Affects Lymphatic Vasculature Development In Vivo

Neonatal CD1 mice from the same litters were used to study the effect of ALK1.Fc on lymphangiogenesis. Mice were injected i.p. with ALK1.Fc ((10 mg/kg body weight) on postnatal day 1 (P1), P3 and P6, and tissue was harvested on P9. Small intestines were removed en bloc and rinsed with PBS. For tail skin, the dermis was separated from the epidermis, washed with PBS and used in subsequent staining. Tissues were fixed for 2 hrs with 4% PFA in PBS at room temperature. After blocking with PHT1 (5% goat serum, 0.2% BSA, 0.5% Triton X-100, NaN₃ in PBS) for 2 hrs at room temperature, tissues were incubated overnight with rat anti-CD31 (1:50, BD Pharmingen) and rabbit polyclonal anti-LYVE-1 (1:500, Upstate), in PHT1. Secondary AlexaFluor 488-conjugated goat anti-rat (1:400, Molecular Probes) and AlexaFluor594-conjugated goat anti-rabbit (1:400, Molecular Probes) in PHT2 (2% BSA, 0.5% Triton X-100, in PBS) were used to visualize antigen-antibody complexes. After staining was completed, tissues were washed 4 times in PBST (PBS, 0.5% Triton X-100), post fixed with 4% PFA in PBS for 5-10 min at room temperature, followed by another 4 washes in PBS. All overnight incubations were carried out at 4° C. Images of flat mounted tissues were captured by confocal fluorescence microscopy.

In the small intestines of ALK1.Fc treated neonatal mice, the capillary blood vessels (CD31 staining) in the villi appeared to be normal although the villi were moderately shorter than the control (FIGS. 10 & 11). In contrast, the lymphatic capillaries (LYVE-1 staining) were severely affected. They failed to extend fully into the villi and were mostly stalled at the base of villi.

The lymphatic vascular network within the neonatal mouse tail skin was also dramatically altered after ALK1.Fc treatment (FIG. 12). The characteristic honeycomb-like pattern was mostly disrupted, with only fragmented and disorganized lymphatic vessels. These results indicate that, in addition to its critical role in regulating blood vessel formation, Alk1 signaling is also essential for postnatal development of lymphatic vasculature.

Example 7

Treatment with ALK1-Fc Affects Pericyte Organization

Figures 13A, 13B:
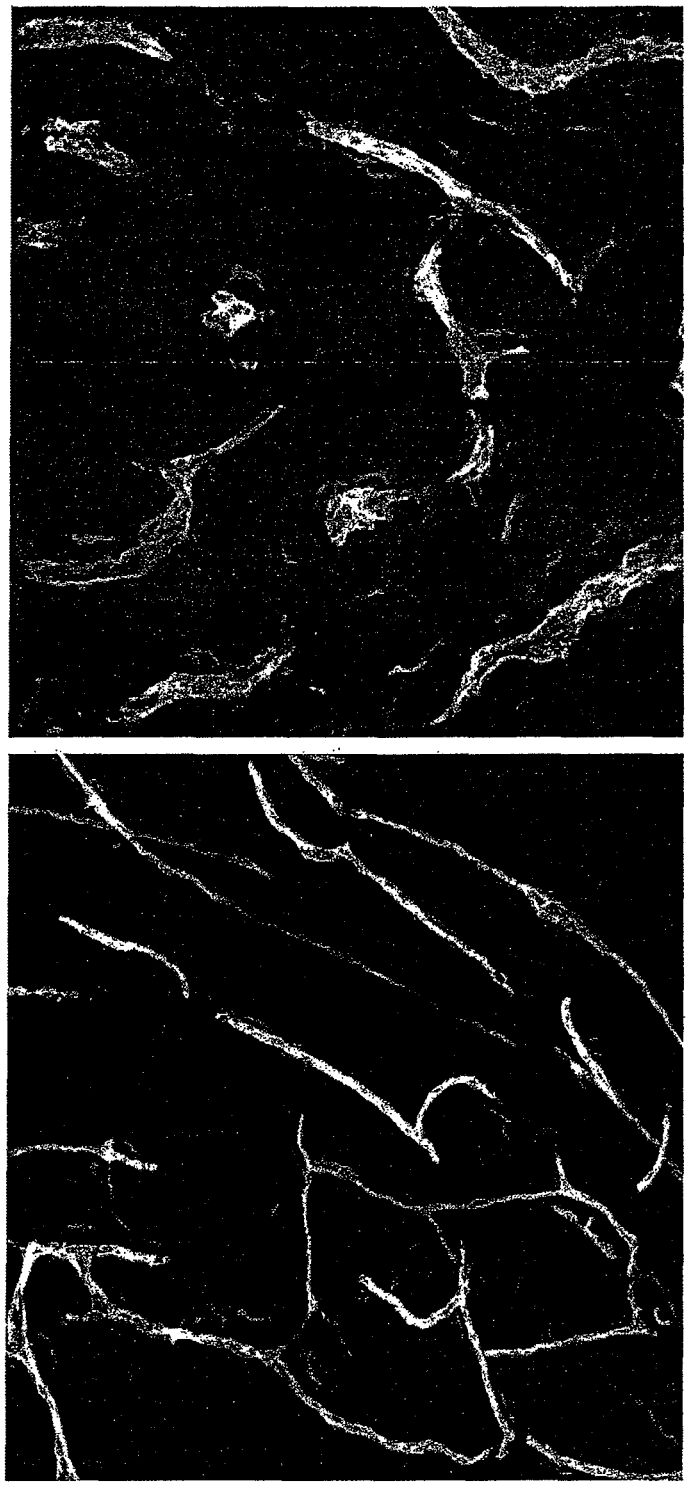
FIGS. 13A-B are confocal images showing pericyte organization in TIB68 tumor model mice treated with PBS (FIG. 13A) or ALK1.Fc (FIG. 13B)

The effect of treatment with ALK1.Fc on pericyte organization in tumor vessels was examined. Beige nude mice were injected with 0.1 ml tumor cell suspension containing 50% matrigel (BD Bioscience) into the right posterior flank. 5×10⁶ mouse monocytic leukemia TIB68 cells (BALB/c-derived and thought to represent an early stage in monocyte-myelocyte differentiation) were injected into each mouse to establish subcutaneous tumors. Alk1.Fc (10 mg/kg) or control vehicle (PBS) was administered via i.p. every three days. Treatments were initiated the next day after cell inoculation and ended 16 days after the first dose. Tumors were fixed for 2 hours in 4% paraformaldehyde (PFA) at room temperature (RT), rinsed in PBS, transferred to 30% sucrose at 4° C. overnight, and embedded in OCT. 80 µm sections of the tumor tissue were washed in PBS, blocked with PHT1 (PBS/10% goat serum/0.5% Triton X-100) at RT for 2 hours, and incubated with primary antibodies diluted in PHT2 (PBS/2% goat serum/0.5% Triton X-100) at 4° C. overnight (rat anti-mouse CD31, 1:50, BD Pharmingen; rabbit anti-Desmin, 1:400, GeneTex). After four washes in PBS/0.2% Triton X-100, the sections were incubated with secondary antibodies (goat-anti rat Alexa 488; goat anti-rabbit Alexa 594, 1:400, Molecular Probes) at RT for 2 h. Sections were washed in PBS/0.2% Triton X-100 followed by PBS, fixed with 4% PFA at RT for 5 min and finally washed with PBS. These results show that ALK1.Fc treated tumor vessels have poorly organized and detached pericytes (FIG. 13).

Example 8

Generation of Additional ALK1 Immunoadhesin Molecules

Standard molecular biology techniques were used to generate the following additional molecules:

```
ALK1.Fc.2 cDNA sequence:
                                           (SEQ ID NO: 3)
ATGACCTTGGGCTCCCCCAGGAAAGGCCTTCTGATGCTGCTGATGGCCT

TGGTGACCCAGGGAGACCCTGTGAAGCCGTCTCGGGGCCCGCTGGTGAC

CTGCACGTGTGAGAGCCCACATTGCAAGGGGCCTACCTGCCGGGGGGCC

TGGTGCACAGTAGTGCTGGTGCGGGAGGAGGGGAGGCACCCCCAGGAAC

ATCGGGGCTGCGGGAACTTGCACAGGGAGCTCTGCAGGGGGCGCCCCAC

CGAGTTCGTCAACCACTACTGCTGCGACAGCCACCTCTGCAACCACAAC

GTGTCCCTGGTGCTGGAGGCCACCCAACCTCCTTCGGAGCAGCCGGGAA

CAGATGGCCAGACCGGTGTCACCGACAAAACTCACACATGCCCACCGTG

CCCAGCACCTGAACTCCTGGGGGGACCGTCAGTCTTCCTCTTCCCCCCA
```

```
AAACCCAAGGACACCCTCATGATCTCCCGGACCCCTGAGGTCACATGCG
TGGTGGTGGACGTGAGCCACGAAGACCCTGAGGTCAAGTTCAACTGGTA
CGTGGACGGCGTGGAGGTGCATAATGCCAAGACAAAGCCGCGGGAGGAG
CAGTACAACAGCACGTACCGTGTGGTCAGCGTCCTCACCGTCCTGCACC
AGGACTGGCTGAATGGCAAGGAGTACAAGTGCAAGGTCTCCAACAAAGC
CCTCCCAGCCCCCATCGAGAAAACCATCTCCAAAGCCAAAGGGCAGCCC
CGAGAACCACAGGTGTACACCCTGCCCCCATCCCGGGAAGAGATGACCA
AGAACCAGGTCAGCCTGACCTGCCTGGTCAAAGGCTTCTATCCCAGCGA
CATCGCCGTGGAGTGGGAGAGCAATGGGCAGCCGGAGAACAACTACAAG
ACCACGCCTCCCGTGCTGGACTCCGACGGCTCCTTCTTCCTCTACAGCA
AGCTCACCGTGGACAAGAGCAGGTGGCAGCAGGGGAACGTCTTCTCATG
CTCCGTGATGCATGAGGCTCTGCACAACCACTACACGCAGAAGAGCCTC
TCCCTGTCTCCGGGTAAATGAG
```

ALK1.Fc.2 protein sequence:

(SEQ ID NO: 4)
```
MTLGSPRKGLLMLLMALVTQGDPVKPSRGPLVTCTCESPHCKGPTCRGA
WCTVVLVREEGRHPQEHRGCNLHRELCRGRPTEFVNHYCCDSHLCNHN
VSLVLEATQPPSEQPGTDGQTGVTDKTHTCPPCPAPELLGGPSVFLFPP
KPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQP
REPQVYTLPPSREEMTKNQVSLTCLVKGFYPSDIAVEWESNGQPENNYK
TTPPVLDSDGSFFLYSKLTVDKSRWQQGNVFSCSVMHEALHNHYTQKSL
SLSPGK
```

ALK1.Fc.3 cDNA sequence:

(SEQ ID NO: 5)
```
ATGACCTTGGGCTCCCCCAGGAAAGGCCTTCTGATGCTGCTGATGGCCT
TGGTGACCCAGGGAGACCCTGTGAAGCCGTCTCGGGGCCCGCTGGTGAC
CTGCACGTGTGAGAGCCCACATTGCAAGGGGCCTACCTGCCGGGGGGCC
TGGTGCACAGTAGTGCTGGTGCGGGAGGAGGGGAGGCACCCCCAGGAAC
ATCGGGGCTGCGGGAACTTGCACAGGGAGCTCTGCAGGGGGCGCCCCAC
CGAGTTCGTCAACCACTACTGCTGCGACAGCCACCTCTGCAACCACAAC
GTGTCCCTGGTGCTGGAGGCCACCCAACCTCCTTCGGAGCAGCCGGGAA
CAGATGGCCAGACCGGTGACAAAACTCACACATGCCCACCGTGCCCAGC
ACCTGAACTCCTGGGGGACCGTCAGTCTTCCTCTTCCCCCCAAAACCC
AAGGACACCCTCATGATCTCCCGGACCCCTGAGGTCACATGCGTGGTGG
TGGACGTGAGCCACGAAGACCCTGAGGTCAAGTTCAACTGGTACGTGGA
CGGCGTGGAGGTGCATAATGCCAAGACAAAGCCGCGGGAGGAGCAGTAC
AACAGCACGTACCGTGTGGTCAGCGTCCTCACCGTCCTGCACCAGGACT
GGCTGAATGGCAAGGAGTACAAGTGCAAGGTCTCCAACAAAGCCCTCCC
AGCCCCCATCGAGAAAACCATCTCCAAAGCCAAAGGGCAGCCCCGAGAA
CCACAGGTGTACACCCTGCCCCCATCCCGGGAAGAGATGACCAAGAACC
AGGTCAGCCTGACCTGCCTGGTCAAAGGCTTCTATCCCAGCGACATCGC
CGTGGAGTGGGAGAGCAATGGGCAGCCGGAGAACAACTACAAGACCACG
CCTCCCGTGCTGGACTCCGACGGCTCCTTCTTCCTCTACAGCAAGCTCA
CCGTGGACAAGAGCAGGTGGCAGCAGGGGAACGTCTTCTCATGCTCCGT
GATGCATGAGGCTCTGCACAACCACTACACGCAGAAGAGCCTCTCCCTG
TCTCCGGGTAAATGA
```

ALK1.Fc.3 protein sequence:

(SEQ ID NO: 6)
```
MTLGSPRKGLLMLLMALVTQGDPVKPSRGPLVTCTCESPHCKGPTCRGA
WCTVVLVREEGRHPQEHRGCNLHRELCRGRPTEFVNHYCCDSHLCNHN
VSLVLEATQPPSEQPGTDGQTGDKTHTCPPCPAPELLGGPSVFLFPPKP
KDTLMISRTPEVTCVVVAVSHEDPEVKFNWYVDGVEVHNAKTKPREEQY
NSTYRVVSVLTVLHQDWLNGKEYKCKVSNKALPAPIEKTISKAKGQPRE
PQVYTLPPSREEMTKNQVSLTCLVKGFYPSDIAVEWESNGQPENNYKTT
PPVLDSDGSFFLYSKLTVDKSRWQQGNVFSCSVMHEALHNHYTQKSLSL
SPGK
```

ALK1.Fc.4 cDNA sequence:

(SEQ ID NO: 7)
```
ATGACCTTGGGCTCCCCCAGGAAAGGCCTTCTGATGCTGCTGATGGCCT
TGGTGACCCAGGGAGACCCTGTGAAGCCGTCTCGGGGCCCGCTGGTGAC
CTGCACGTGTGAGAGCCCACATTGCAAGGGGCCTACCTGCCGGGGGGCC
TGGTGCACAGTAGTGCTGGTGCGGGAGGAGGGGAGGCACCCCCAGGAAC
ATCGGGGCTGCGGGAACTTGCACAGGGAGCTCTGCAGGGGGCGCCCCAC
CGAGTTCGTCAACCACTACTGCTGCGACAGCCACCTCTGCAACCACAAC
GTGTCCCTGGTGCTGGAGGCCACCCAACCTCCTTCGGAGCAGCCGGGAA
CAGATGGCCAGGAGCCCAAATCTTGTGACAAAACTCACACATGCCCACC
GTGCCCAGCACCTGAACTCCTGGGGGACCGTCAGTCTTCCTCTTCCCC
CCAAAACCCAAGGACACCCTCATGATCTCCCGGACCCCTGAGGTCACAT
GCGTGGTGGTGGACGTGAGCCACGAAGACCCTGAGGTCAAGTTCAACTG
GTACGTGGACGGCGTGGAGGTGCATAATGCCAAGACAAAGCCGCGGGAG
GAGCAGTACAACAGCACGTACCGTGTGGTCAGCGTCCTCACCGTCCTGC
ACCAGGACTGGCTGAATGGCAAGGAGTACAAGTGCAAGGTCTCCAACAA
AGCCCTCCCAGCCCCCATCGAGAAAACCATCTCCAAAGCCAAAGGGCAG
CCCCGAGAACCACAGGTGTACACCCTGCCCCCATCCCGGGAAGAGATGA
CCAAGAACCAGGTCAGCCTGACCTGCCTGGTCAAAGGCTTCTATCCCAG
CGACATCGCCGTGGAGTGGGAGAGCAATGGGCAGCCGGAGAACAACTAC
AAGACCACGCCTCCCGTGCTGGACTCCGACGGCTCCTTCTTCCTCTACA
GCAAGCTCACCGTGGACAAGAGCAGGTGGCAGCAGGGGAACGTCTTCTC
ATGCTCCGTGATGCATGAGGCTCTGCACAACCACTACACGCAGAAGAGC
CTCTCCCTGTCTCCGGGTAAATGA
```

ALK1.Fc.4 protein sequence:

(SEQ ID NO: 8)
```
MTLGSPRKGLLMLLMALVTQGDPVKPSRGPLVTCTCESPHCKGPTCRGA
WCTVVLVREEGRHPQEHRGCNLHRELCRGRPTEFVNHYCCDSHLCNHN
VSLVLEATQPPSEQPGTDGQEPKSCDKTHTCPPCPAPELLGGPSVFLFP
PKPKDTLMISRTPEVTCVVVDVSHEDPEVKFNWYVDGVEVHNAKTKPRE
```

EQYNSTYRVVSVLTVLHQDWLNGKEYKCKVSNKALPAPIEKTISKAKGQ

PREPQVYTLPPSREEMTKNQVSLTCLVKGFYPSDIAVEWESNGQPENNY

KTTPPVLDSDGSFFLYSKLTVDKSRWQQGNVFSCSVMHEALHNHYTQKS

LSLSPGK

ALK1.Fc.5 cDNA sequence:
(SEQ ID NO: 9)
ATGACCTTGGGCTCCCCCAGGAAAGGCCTTCTGATGCTGCTGATGGCCT

TGGTGACCCAGGGAGACCCTGTGAAGCCGTCTCGGGGCCCGCTGGTGAC

CTGCACGTGTGAGAGCCCACATTGCAAGGGGCCTACCTGCCGGGGGGCC

TGGTGCACAGTAGTGCTGGTGCGGGAGGAGGGGAGGCACCCCCAGGAAC

ATCGGGGCTGCGGGAACTTGCACAGGGAGCTCTGCAGGGGGCGCCCCAC

CGAGTTCGTCAACCACTACTGCTGCGACAGCCACCTCTGCAACCACAAC

GTGTCCCTGGTGCTGGAGGCCACCCAACCTCCTTCGGAGCAGCCGGGAA

CAGATGGCCAGGAGCCCAAATCTTCTGACAAAACTCACACATGCCCACC

GTGCCCAGCACCTGAACTCCTGGGGGGACCGTCAGTCTTCCTCTTCCCC

CCAAAACCCAAGGACACCCTCATGATCTCCCGGACCCCTGAGGTCACAT

GCGTGGTGGTGGACGTGAGCCACGAAGACCCTGAGGTCAAGTTCAACTG

GTACGTGGACGGCGTGGAGGTGCATAATGCCAAGACAAAGCCGCGGGAG

GAGCAGTACAACAGCACGTACCGTGTGGTCAGCGTCCTCACCGTCCTGC

ACCAGGACTGGCTGAATGGCAAGGAGTACAAGTGCAAGGTCTCCAACAA

AGCCCTCCCAGCCCCCATCGAGAAAACCATCTCCAAAGCCAAAGGGCAG

CCCCGAGAACCACAGGTGTACACCCTGCCCCCATCCCGGGAAGAGATGA

CCAAGAACCAGGTCAGCCTGACCTGCCTGGTCAAAGGCTTCTATCCCAG

CGACATCGCCGTGGAGTGGGAGAGCAATGGGCAGCCGGAGAACAACTAC

AAGACCACGCCTCCCGTGCTGGACTCCGACGGCTCCTTCTTCCTCTACA

GCAAGCTCACCGTGGACAAGAGCAGGTGGCAGCAGGGGAACGTCTTCTC

ATGCTCCGTGATGCATGAGGCTCTGCACAACCACTACACGCAGAAGAGC

CTCTCCCTGTCTCCGGGTAAATGAG

ALK1.Fc.5 protein sequence:
(SEQ ID NO: 10)
MTLGSPRKGLLMLLMALVTQGDPVKPSRGPLVTCTCESPHCKGPTCRGA

WCTVVLVREEGRHPQEHRGCGNLHRELCRGRPTEFVNHYCCDSHLCNHN

VSLVLEATQPPSEQPGTDGQEPKSSDKTHTCPPCPAPELLGGPSVFLFP

PKPKDTLMISRTPEVTCVVVDVSHEDPEVKFNWYVDGVEVHNAKTKPRE

EQYNSTYRVVSVLTVLHQDWLNGKEYKCKVSNKALPAPIEKTISKAKGQ

PREPQVYTLPPSREEMTKNQVSLTCLVKGFYPSDIAVEWESNGQPENNY

KTTPPVLDSDGSFFLYSKLTVDKSRWQQGNVFSCSVMHEALHNHYTQKS

LSLSPGK

Example 9

Treatment with ALK1 Immunoadhesins Affects Retinal Vascular Development In Vivo

Mice were injected i.p. with ALK1.Fc, ALK1.Fc.2, ALK1.Fc.4 or ALK1.Fc.5 (10 mg/kg body weight) on postnatal day 4 (P4) and P6. On P8, mice were anesthetized. Eyes were collected and fixed with 4% PFA in PBS overnight, followed by PBS washes. The dissected retinas were blocked with 10% goat serum in PBST (PBS, 0.5% Triton X-100) for 3 hrs, then incubated overnight with rat anti-CD31 (1:50, BD Pharmingen) in PBST. To visualize the anti-CD31, retinas were incubated with AlexaFluor 488-conjugated goat anti-rat (1:400, Molecular Probes) in PBST. After staining was completed, retinas were washed 4 times in PBST. All overnight incubations were done at 4° C. Images of flat mounted retinas were captured by confocal fluorescence microscopy.

Figure 14:
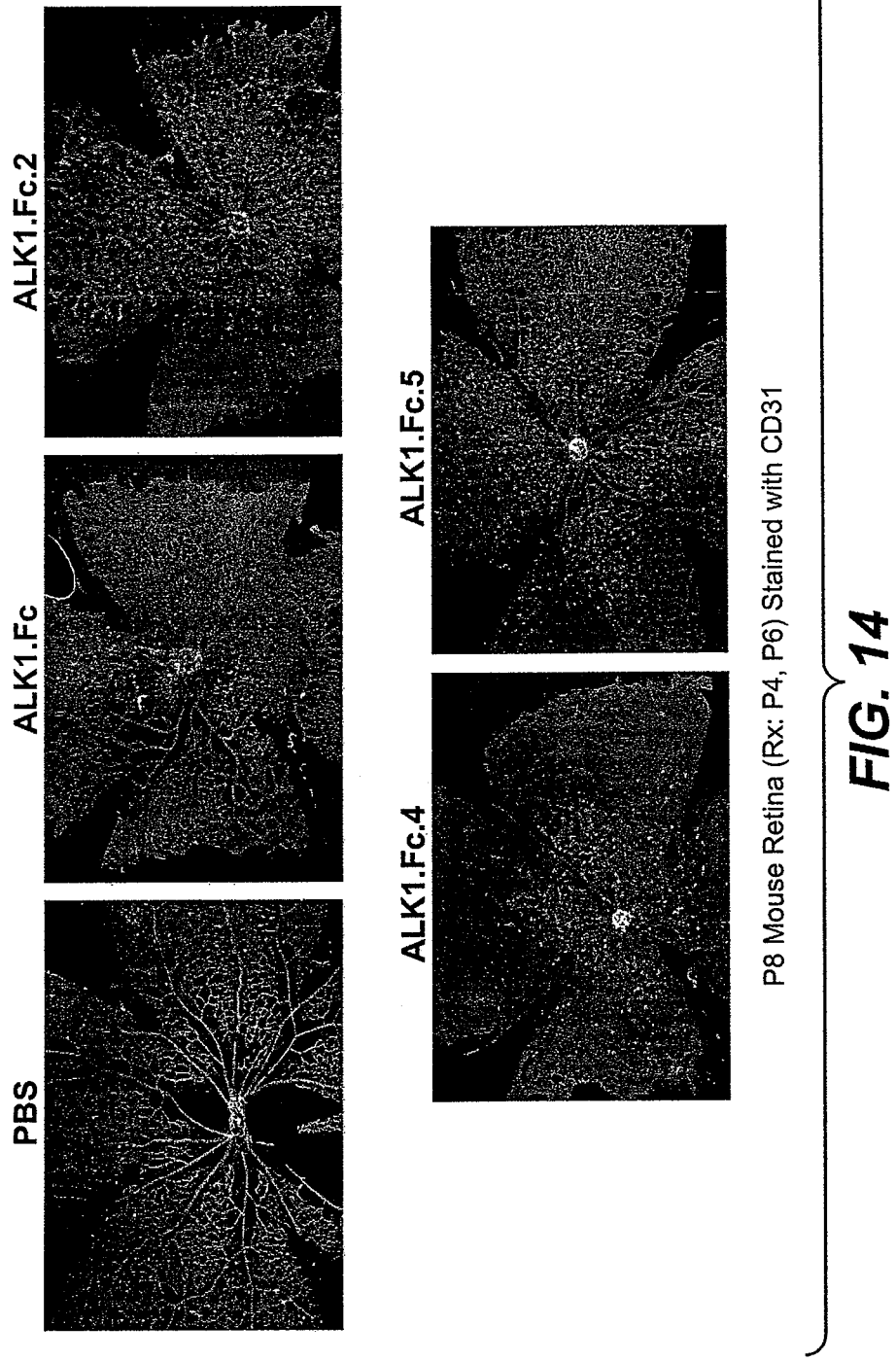
FIG. 14 shows confocal images from mouse retinas collected on P8 and stained with anti-CD31. Mice were injected i.p. with PBS, ALK1.Fc, ALK1.Fc.2, ALK1.Fc.4 or ALK1.Fc.5 on P4 and P6.

Early postnatal mouse retina develops a stereotypic vascular pattern in a well-defined sequence of events. The superficial retinal vasculature develops as an expanding network from the optic nerve head, with active sprouting at the periphery and extensive remodeling at the center. Different aspects of vessel development, e.g. vessel sprouting, remodeling, maturation and arterial-venous specification can be readily followed. In ALK1 immunoadhesin (ALK1.Fc, ALK1.Fc.2, ALK1.Fc.4 and ALK1.Fc.5) treated retinas, the characteristic pattern of radially alternating arteries and veins was mostly unaffected. There was, however, a clear increase of the vascular density, especially the microvessels near the veins (FIG. 14). These results indicate that the effects of treatment with the additional ALK1 immunoadhesins (ALK1.Fc.2, ALK1.Fc.4 and ALK1.Fc.5) on vascular development in neonatal mouse retina are similar to treatment with ALK1.Fc.

What is claimed is:

1. A method of inhibiting lymphangiogenesis comprising administering to a subject in need of inhibition of lymphangiogenesis an effective amount of an ALK-1 immunoadhesin, whereby the lymphangiogenesis is inhibited, wherein the ALK-1 immunoadhesin comprises amino acid residues 22-352 of SEQ ID NO: 2, and wherein the subject suffers from a tumor.

2. The method of claim 1, wherein the tumor is carcinoma, lymphoma, blastoma, sarcoma, or leukemia.

3. A method for treating a pathological condition associated with lymphangiogenesis in a subject comprising administering to the subject an effective amount of an ALK-1 immunoadhesin, whereby the pathological condition associated with lymphangiogenesis is treated, wherein the ALK-1 immunoadhesin comprises amino acid residues 22-352 of SEQ ID NO: 2, and whereby the pathological condition associated with lymphangiogenesis is a tumor.

4. A method of inhibiting tumoral lymphangiogenesis in a subject comprising administering to the subject an effective amount of an ALK-1 immunoadhesin, whereby the tumoral lymphangiogenesis is inhibited, wherein the ALK-1 immunoadhesin comprises amino acid residues 22-352 of SEQ ID NO: 2.

5. A method of disrupting pericyte organization in a subject comprising administering to the subject an effective amount of an ALK-1 immunoadhesin, whereby the pericyte organization is disrupted, wherein the ALK-1 immunoadhesin comprises amino acid residues 22-352 of SEQ ID NO: 2, and wherein the subject suffers from a tumor.

6. A method of inhibiting tumor growth in a subject comprising administering to the subject an effective amount of an ALK-1 immunoadhesin, whereby the tumor growth is inhibited, wherein the ALK-1 immunoadhesin comprises amino acid residues 22-352 of SEQ ID NO: 2.

7. A method of treating a tumor in a subject comprising administering to the subject an effective amount of an ALK-1 immunoadhesin, whereby the tumor is treated, wherein the ALK-1 immunoadhesin comprises amino acid residues 22-352 of SEQ ID NO: 2.

8. The method of claim 7, wherein the tumor is carcinoma, lymphoma, blastoma, sarcoma, or leukemia.

9. The method of claim 7, further comprising administering to the subject an effective amount of an anti-angiogenesis agent.

10. The method of claim 9, wherein the anti-angiogenesis agent is an antagonist of vascular endothelial growth factor (VEGF).

11. The method of claim 10, wherein the antagonist of VEGF is an anti-VEGF antibody.

12. The method of claim 11, wherein the anti-VEGF antibody is bevacizumab.

* * * * *